(12) United States Patent
Zhou

(10) Patent No.: US 8,513,181 B2
(45) Date of Patent: Aug. 20, 2013

(54) SUBSTANCES AND COMPOSITIONS FOR ENHANCING DNA REPAIR AND METHODS OF USE

(75) Inventor: Pengbo Zhou, Princeton Junction, NJ (US)

(73) Assignee: Cornell University, Ithaca, NY (US)

(*) Notice: Subject to any disclaimer, the term of this patent is extended or adjusted under 35 U.S.C. 154(b) by 0 days.

(21) Appl. No.: 12/990,373

(22) PCT Filed: Apr. 29, 2009

(86) PCT No.: PCT/US2009/042108
§ 371 (c)(1),
(2), (4) Date: Oct. 29, 2010

(87) PCT Pub. No.: WO2009/134883
PCT Pub. Date: Nov. 5, 2009

(65) Prior Publication Data
US 2011/0044921 A1  Feb. 24, 2011

Related U.S. Application Data

(60) Provisional application No. 61/048,868, filed on Apr. 29, 2008.

(51) Int. Cl.
*A61K 31/00* (2006.01)
*A61K 38/00* (2006.01)
*C12N 15/113* (2010.01)

(52) U.S. Cl.
USPC .............................. 514/1; 514/1.1; 514/44 A

(58) Field of Classification Search
None
See application file for complete search history.

(56) References Cited

U.S. PATENT DOCUMENTS

| | | | |
|---|---|---|---|
| 6,713,267 B2 | 3/2004 | Deshaies et al. | |
| 2006/0105409 A1 | 5/2006 | Issakani et al. | |

FOREIGN PATENT DOCUMENTS

| | | | |
|---|---|---|---|
| WO | WO 2005/114188 A2 | 12/2005 | |
| WO | WO 2007026240 A1 | * 3/2007 | |

OTHER PUBLICATIONS

Aboussekhra et al., *Cell*, 80: 859-868 (1995).
Alekseev et al., *Cancer Research*, 65: 10298-10306 (2005).
Angers et al., *Nature*, 443: 590-593 (2006).
Araujo et al., *Genes Dev.*, 14: 349-359 (2000).
Banks et al., *Cell Cycle*, 5(15): 1719-1729 (2006).
Batty et al., *J. Mol. Biol.*, 300: 275-290 (2000).
Brooks et al., *J. Biol. Chem.* 275(29): 22355-22362 (2000).
Brooks, P.J., *Neuroscience*, 145: 1407-1417 (2007).
Bruncko et al., *J. Med.Chem.*, 50: 641-662 (2007).
Cafardi et al., *Expert Opin. Biol. Ther.*, 8(6): 829-838 (2008).
Cang et al., *Cell*, 127: 929-940 (2006).
Chen et al., *Cancer Research*, 58: 3677-3683 (1998).
Chen et al., *J. Biol. Chem.*, 276: 48175-48182 (2001).
Chen et al., *Mol. Cell*, 22: 489-499 (2006).
Chorev et al., *Trends Biotechnol.*, 13: 438-445 (1995).
Dai et al., *Cell Division*, 1(1): 14 (Jul. 10, 2006).
El-Mahdy et al., *J. Biol. Chem.*, 281(19): 13404-13411 (2006).
Fitch et al., *DNA Repair (Amst)*, 2: 819-826 (2003).
Fitch et al., *J. Biol. Chem.*, 278: 46906-46910 (2003).
Gitig et al., *Methods Mol. Biol.*, 142: 109-123 (2000).
Goudreau et al., *Bioorg. Med. Chem.*, 15: 2690-2700 (2007).
Groisman et al., *Cell*, 113: 357-367 (2003).
Hanawalt, *Oncogene*, 21: 8949-8956 (2002).
Hasty et al., *Science*, 299: 1355-1359 (2003).
He et al., *Genes Development*, 20: 2949-2954 (2006).
He et al., *Science*, 310: 1022-1025 (2005).
Higa et al, *Nat. Cell Biol.*, 8: 1277-1283 (2006).
Higa et al., *Nat. Cell Biol.*, 5: 1008-1015 (2003).
Higa et al., *Cell Division*, 2(1): 5 (Feb. 6, 2007).
Higa et al., *Cell Cycle*, 5(15) 1675-1680 (2006).
Hofmann et al., *Trends Biochem. Sci.*, 23: 204-205 (1998).
Hu et al., *Nat. Cell Biol.*, 6(10): 1003-1009 (2004).
Itoh et al., *J. Investig. Dermatol.*, 114: 1022-1029 (2000).
Itoh et al., *Proc. Natl. Acad. Sci. U.S.A.*, 101: 2052-2057 (2004).
Jin et al., *Mol. Cell*, 23: 709-721 (2006).
Kansy et al., *J. Med. Chem.*, 41: 1007-1010 (1998).
Keeney et al., *Proc. Natl. Acad. Sci. U.S.A.*, 91: 4053-4056 (1994).
Kelley et al., *Anticancer Agents Med. Chem.*, 8(4): 417-425 (2008).
Lakso et al., *Proc. Natl. Acad. Sci. U.S.A.*, 93: 5860-5865 (1996).
Lee et al., *Mol. Cell*, 26: 775-780 (2007).
Li et al., *Cell*, 124: 105-117 (2006).
Li et al., *Mol. Cell Biol.*, 22: 4997-5005 (2002).
Li et al., *Cancer Research*, 66(17): 8590-8597 (2006).
Liu et al., *Molecular Cell*, 34(14): 451-460 (2009).
Lo et al., *BMC Cancer*, 5: 135 (Oct. 19, 2005).
Luch, Andreas, *Nature Rev. Cancer*, 5: 113-125 (2005).
Matsunaga et al., *Photochem. Photobiol.*, 57: 934-940 (1993).
Mu et al., *J. Biol. Chem.*, 270: 2415-2418 (1995).
Mu et al., *J. Biol. Chem.*, 271: 8285-8294 (1996).
Nag et al., *Mol. Cell Biol.*, 21: 6738-6747 (2001).
Nagahara et al., *Nat. Med.*, 4: 1449-1452 (1998).
Nishitani et al., *J. Biol. Chem.*, 283: 29045-29052 (2008).
Ohtake et al., *Nature*, 446: 562-566 (2007).
Otoshi et al., *Cancer Research*, 60: 1729-1735 (2000).
Pan et al., *Oncogene*, 23: 1985-1997 (2004).
Parks et al., *Bioorg. Med. Chem. Lett.*, 15: 765-770 (2005).
Petroski et al., *Nat. Rev. Mol. Cell. Biol.*, 6: 9-20 (2005).
Raimundo et al., *J. Med. Chem.*, 47: 3111-3130 (2004).

(Continued)

*Primary Examiner* — Tracy Vivlemore
(74) *Attorney, Agent, or Firm* — Leydig, Voit & Mayer, Ltd.

(57) ABSTRACT

The invention provides methods of preventing or treating a condition associated with DNA damage in an animal comprising the administration of a substance that interferes with the activity of the CUL4A ubiquitin ligase. The invention also provides a substance that interferes with the activity of CUL4A, as well as compositions comprising the interfering substance and a carrier. The substance of the invention preferably enhances nucleotide excision repair activity in an animal. The invention further provides methods of identifying substances that negatively or positively modulate the expression and/or activity of CUL4A.

23 Claims, 14 Drawing Sheets

(56) References Cited

OTHER PUBLICATIONS

Rapic-Otrin et al., *Nucleic Acids Research*, 30: 2588-2598 (2002).
Reardon et al., *Proc. Natl. Acad. Sci. USA*, 94: 9463-9468 (1997).
Rush et al., *J. Med. Chem.*, 48: 1489-1495 (2005).
Salmon et al., *Am. J. Physiol. Endocrinol. Metab.*, 289: E23-E29 (2005).
Sancar, A., *Annu Rev. Biochem.*, 65: 43-81 (1996).
Shiyanov et al., *J. Biol. Chem.*, 274: 35309-35312 (1999).
Sugasawa et al., *Cell*, 121: 387-400 (2005).
Sui et al., *Methods Mol. Biol.*, 309: 205-218 (2005).
Tan et al., *Journal of Virology*, 81(19): 10822-10830 (2007).
Tang et al., *DNA Repair (Amst)*, 1: 601-616 (2002).
Tarpey et al., *Am. J. Hum. Genet.*, 80: 345-352 (2007).
Thanos et al., *J. Am. Chem. Soc.*, 125: 15280-15281 (2003).
Thoma et al., *Mol. Carcinog.*, 38: 1-13 (2003).
Van Hoffen et al., *Nucleic Acids Research*, 27(14): 2898-2904 (1999).
Van Regenmortel et al., *Curr. Opin. Biotechnol.*, 9: 377-382 (1998).
Vasioukhin et al., *Proc. Natl. Acad. Sci. U.S.A.*, 96: 8551-8556 (1999).
Vassilev et al., *Science*, 303: 844-848 (2004).
Wakasugi et al., *J. Biol. Chem.*, 276(8): 15434-15440 (2001).
Wakasugi et al., *J. Biol. Chem.*, 277(3): 1637-1640 (2002).
Wang et al., *J. Biol. Chem.*, 279(8): 6976-6985 (2004).
Wang et al., *DNA Repair*, 2: 483-499 (2003).
Wang et al., *Mol. Cell*, 22(3): 383-394 (2006).
Wittschieben et al., *DNA Repair*, 2: 1065-1069 (2003).
Wood et al., *Science*, 291: 1284-1289 (2001).
Yasui et al., *Hepatology*, 35: 1476-1484 (2002).
Yoon et al., *Oncogene*, 24: 469-478 (2004).
Zhang et al., *Journal Biomol. Screen*, 4(2): 67-73 (1999).
Zou et al., *Am. J. Hum. Genet.*, 80: 561-566 (2007).
European Patent Office, International Search Report in International Patent Application No. PCT/US2009/042108 (Oct. 19, 2009).
European Patent Office, Written Opinion in International Patent Application No. PCT/US2009/042108 (Oct. 19, 2009).
European Patent Office, International Preliminary Report on Patentability in International Patent Application No. PCT/US2009/042108 (Nov. 2, 2010).
Emanuele et al., "Global Identification of Modular Cullin-RING Ligase Substrates," *Cell*, 147: 459-474 (2011).
Kapetanaki et al., "The DDB1-CUL4A$^{DDB2}$ ubiquitin ligase is deficient in xeroderma pigmentosum group E and targets histone H2A at UV-damaged DNA sites," *PNAS*, 103(8): 2588-2593 (2006).
Kulaksiz et al., "Xeroderma Pigmentosum Complementation Group E Protein (XPE/DDB2): Purification of Various Complexes of XPE and Analyses of Their Damaged DNA Binding and Putative DNA Repair Properties," *Molecular and Cellular Biology*, 25(22): 9784-9792 (2005).
Reardon et al., "Recognition and repair of the cyclobutane thymine dimer, a major cause of skin cancers, by the human excision nuclease," *Genes & Development*, 17: 2539-2551 (2003).

\* cited by examiner

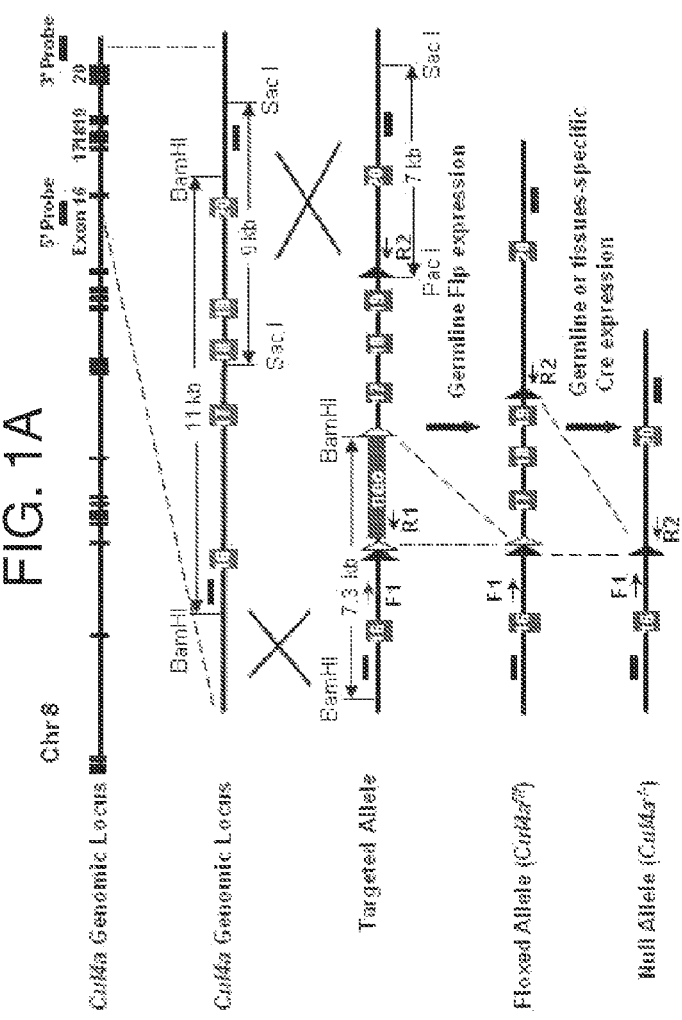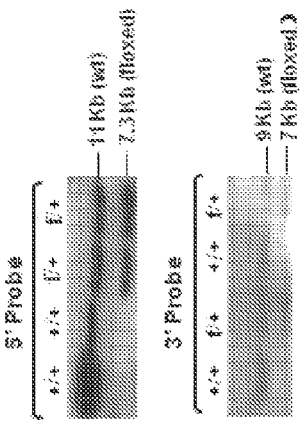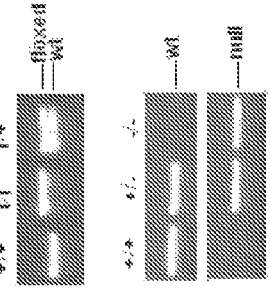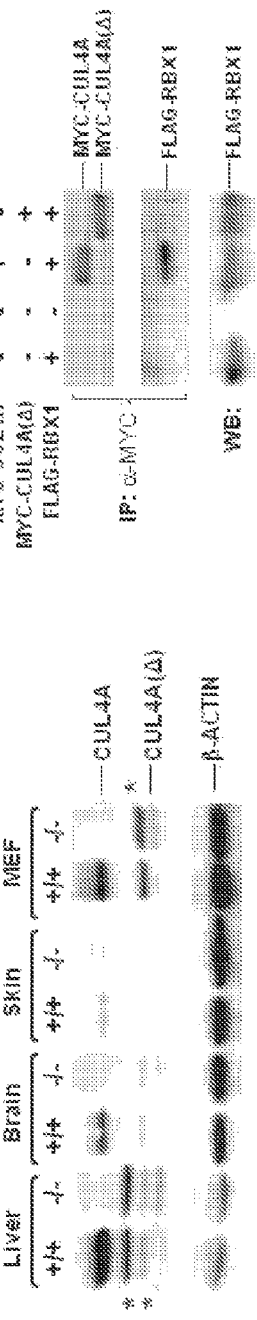

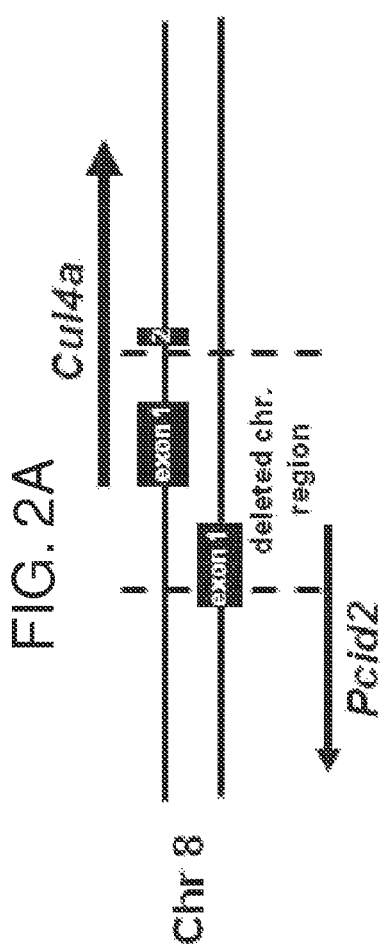
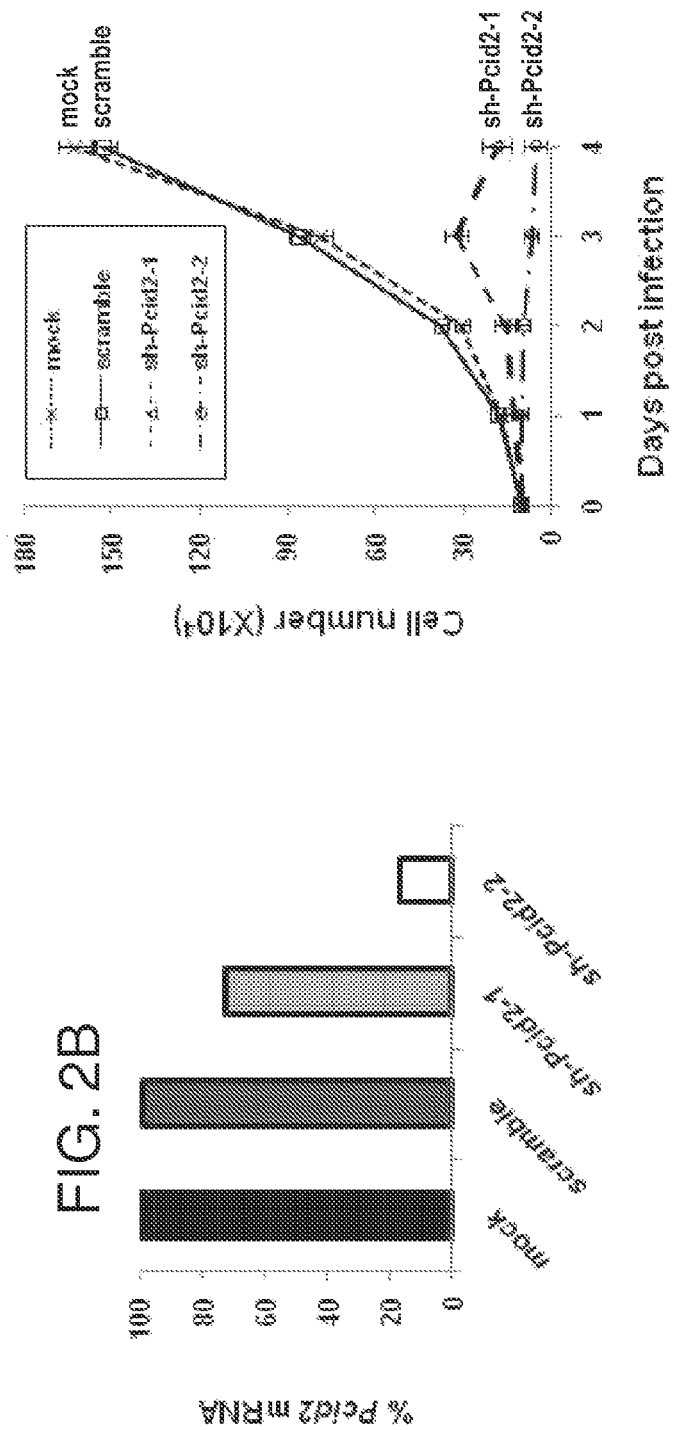

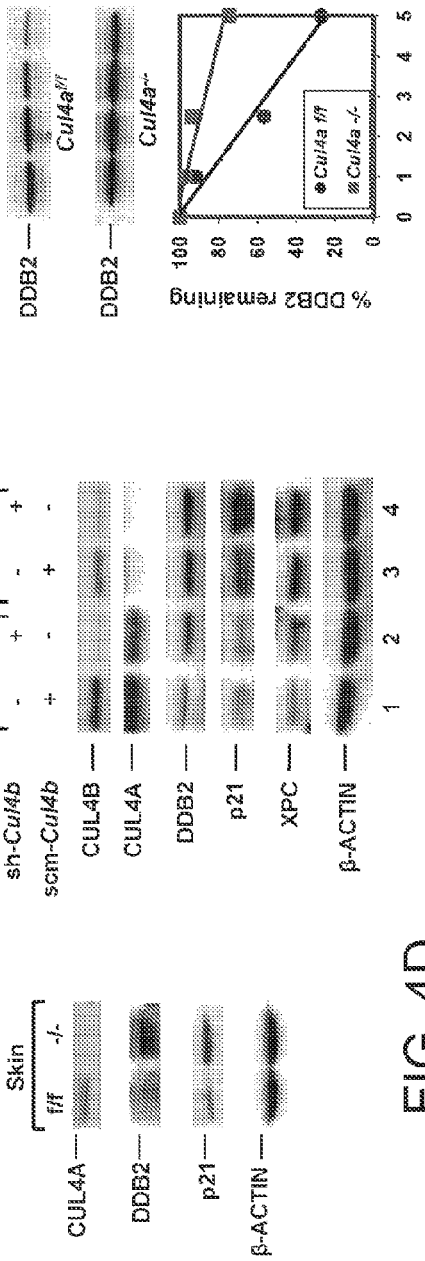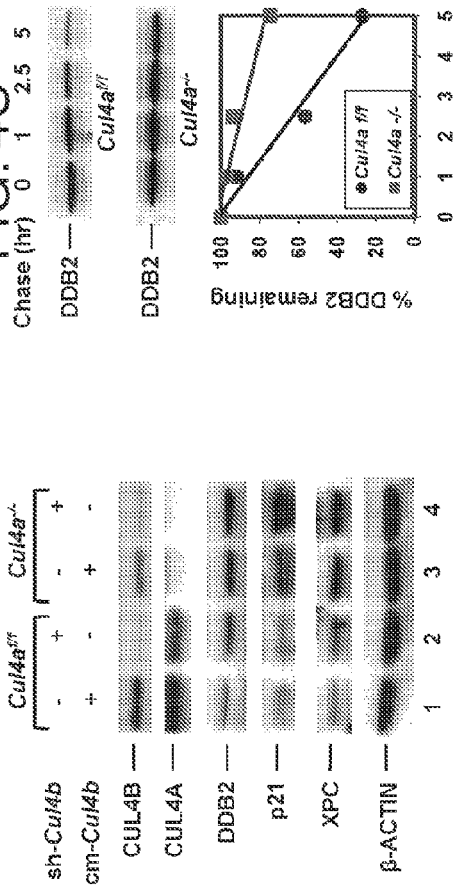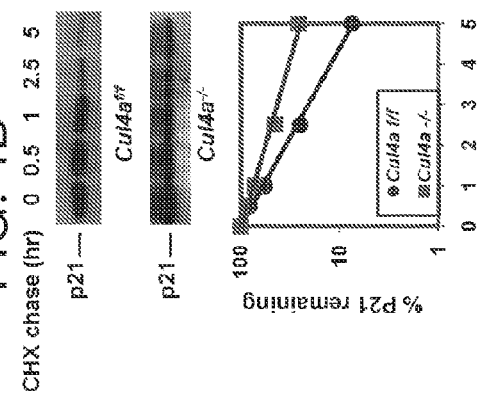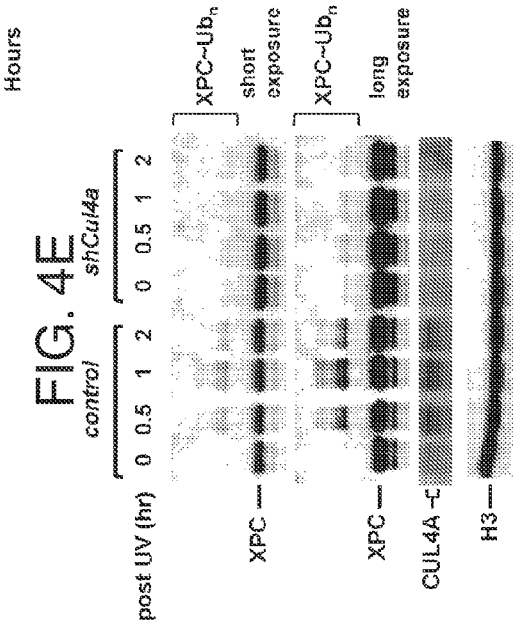

SUBSTANCES AND COMPOSITIONS FOR ENHANCING DNA REPAIR AND METHODS OF USE

CROSS-REFERENCE TO RELATED APPLICATIONS

This patent application is the U.S. national phase of International Patent Application No. PCT/US2009/042108, filed Apr. 29, 2009, which claims the benefit of U.S. Provisional Patent Application No. 61/048,868, filed Apr. 29, 2008, each of which is incorporated by reference in its entirety.

STATEMENT REGARDING FEDERALLY SPONSORED RESEARCH AND DEVELOPMENT

This invention was made with Government support under Grant Number 5R01CA098210 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 45,854 Byte ASCII (Text) file named "707049SequenceListing.txt," created on Oct. 28, 2010.

BACKGROUND OF THE INVENTION

Cells are continually exposed to factors, such as intracellular reactive species and environmental agents, which are capable of causing DNA damage. The potentially mutagenic consequences of DNA damage are minimized by DNA repair pathways, which are broadly characterized into three forms: base excision repair (BER), mismatch repair (MMR), and nucleotide excision repair (NER) (Wood et al., *Science*, 291: 1284-1289 (2001)). Deficiencies in DNA damage repair underlie the pathogenesis of cancer as well as many genetic disorders, such as Xeroderma pigmentosum, Cockayne syndrome, and Ataxia-telangiectasia.

Exposure to ultraviolet light (UV) irradiation or chemical mutagens leads to the accumulation of damaged DNA, which in turn, results in mutations that contribute to the development of cancer. Eukaryotic cells respond to UV irradiation by induction of the NER pathway, which identifies and removes damaged DNA, and by activation of the DNA damage checkpoint to halt cell cycle progression, thereby allowing time for NER action. NER is the major DNA repair pathway by which cells remove helix-distorting DNA damage caused by UV irradiation and chemical mutagens (Friedberg et al., DNA Repair and Mutagenesis, 2nd Edition, ASM Press, Washington, D.C. (2006)).

NER is a multistep process that employs over 30 proteins to carry out the distinct steps of recognizing DNA damage, incising the 5' and 3' ends of the lesion to remove damaged DNA, filling in the gap with DNA polymerase, and attaching the newly synthesized DNA to the parental DNA via DNA ligase activity (see, e.g., Friedberg et al., DNA Repair and Mutagenesis, 2nd Edition, ASM Press, Washington, D.C. (2006); Sancar, *Annu. Rev. Biochem.*, 65: 43-81 (1996)). NER consists of two pathways with distinct DNA strand specificities: the transcription-coupled repair pathway (TCR) which removes lesions from DNA strands transcribed by RNA polymerase II, and the global genomic repair pathway (GGR) which repairs damage on the non-transcribed strand of expressed genes as well as from inactive chromatin (reviewed in Hanawalt, *Oncogene*, 21: 8949-8956 (2002)). The NER process has been studied extensively, and the components essential to perform the excision and repair reactions have been defined by in vitro reconstitution using recombinant proteins and damaged DNA templates (Aboussekhra et al., *Cell*, 80: 859-868 (1995); Araujo et al., *Genes Dev.*, 14: 349-359 (2000); Mu et al., *J. Biol. Chem.*, 271: 8285-8294 (1996); Mu et al., *J. Biol. Chem.*, 270: 2415-2418 (1995)).

NER factors involved in the GGR pathway of DNA damage recognition include XPA-RPA, XPC-HR23B, and the heterodimeric, damage-specific DNA binding proteins consisting of DDB1 (p127) and DDB2 (p48) subunits. Among these DNA damage sensors, the heterodimeric DDB1-DDB2 exhibit the highest affinity (designated UV-DDB activity) for UV-induced cyclobutane pyrimidine dimers (CPDs) and 6-4 photoproducts (6-4PPs) (Batty et al., *J. Mol. Biol.*, 300: 275-290 (2000)). Mutations in DDB2 are responsible for xeroderma pigmentosum complementation group E (XP-E) cases, which are characterized by defects in GGR-mediated removal of damaged DNA and predisposition to skin cancer (Wittschieben and Wood, *DNA Repair (Amst)*, 2: 1065-1069 (2003). Following UV irradiation, DDB1 and DDB2 immediately accumulate on damaged DNA and are subsequently ubiquitinated and degraded by the CUL4A ubiquitin ligase (Chen et al., *Mol. Cell*, 22: 489-499 (2006); Fitch et al., *DNA Repair (Amst)*, 2: 819-826 (2003); Groisman et al., *Cell*, 113: 357-367 (2003); Rapic-Otrin et al., *Nucleic Acids Res.*, 30: 2588-2598 (2002)). CUL4A is also responsible for the turnover of DDB2 under normal growth conditions (Chen et al., *J. Biol. Chem.*, 276: 48175-48182 (2001); Nag et al., *Mol. Cell. Biol.*, 21: 6738-6747 (2001), which leads to an overall decrease in UV-DDB activity (Chen et al., *J. Biol. Chem.*, 276: 48175-48182 (2001)).

The CUL4A ubiquitin ligase functions as a component of a multimeric complex wherein the C-terminus of CUL4A interacts with the RING finger protein Rbx1/ROC1/Hrt1 (hereinafter referred to as Rbx1) to recruit the E2 ubiquitin-conjugating enzyme, and the N-terminus of CUL4A interacts with DDB1. DDB1, in turn, acts as an adaptor, binding to DDB1, CUL4A associated factors (DCAFs), which serve as specific substrate receptors (Angers et al., *Nature*, 443: 590-593 (2006); He et al., *Genes Dev.*, 20: 2949-2954 (2006); Higa et al., *Nat Cell Biol.*, 8: 1277-1283 (2006); Jin et al., *Mol. Cell*, 23: 709-721 (2006); Lee and Zhou, *Mol. Cell*, 26: 775-780 (2007)). CUL4B, the other CUL4 family member, has extensive sequence homology with CUL4A and shares some redundant functions with CUL4A, including maintaining cell growth and mediating the ubiquitination of certain CUL4 targets (Higa et al., *Nat. Cell Biol.*, 5: 1008-1015 (2003); Hu et al., *Nat. Cell Biol.*, 6: 1003-1009 (2004)). CUL4B containing ubiquitin ligase complexes have some unique features, such as the ability to degrade sex steroid hormone receptors (Ohtake et al., *Nature*, 446: 562-566 (2007)). Additionally, CUL4B mutations have been identified as the causal genetic defects underlying X-linked mental retardation (Tarpey et al., *Am. J. Hum. Genet.*, 80: 345-352 (2007); Zou et al., *Am. J. Hum. Genet.*, 80: 561-566 (2007)).

To date, most of the cancer therapies that target DNA repair pathways are substances that inhibit DNA repair in cancer cells in order to enhance the effects DNA-damaging chemotherapies and radiotherapies (Kelley and Fishel. *Anticancer Agents Med. Chem.*, 8(4): 417-25 (2008)).

Comparatively fewer attempts have been made to improve or accelerate DNA repair in order to reduce the consequences of DNA damage after it has occurred in order to prevent or treat disease, although compositions comprising T4 endonuclease V have been examined as a potential therapy for skin cancer (Cafardi and Elmets. *Expert Opin. Biol. Ther.*, 8(6): 829-38 (2008)).

Thus, there is a need for compositions and methods to enhance DNA repair in cells and in animals. This invention provides such compositions and methods, which may be useful for the prevention or treatment of diseases associated with DNA damage.

BRIEF SUMMARY OF THE INVENTION

The invention provides a method of preventing or treating a condition associated with DNA damage in an animal, which method comprises administering to an animal in need thereof an effective amount of a substance that interferes with the activity of CUL4A, thereby preventing or treating a condition associated with DNA damage in the animal.

The invention additionally provides a method of preventing or treating a condition associated with DNA damage in an animal, which method comprises administering to an animal in need thereof an effective amount of a substance that interferes with the activity of CUL4A, wherein the substance that interferes with the activity of CUL4A causes an increase in nucleotide excision repair activity, thereby preventing or treating a condition associated with DNA damage in the animal.

The invention also provides a substance that interferes with the activity of CUL4A in an animal, as well as a composition comprising such a substance and a carrier therefor. Such a substance can enhance nucleotide excision repair activity in an animal.

The invention further provides a method of identifying a substance that modulates CUL4A ubiquitin ligase activity, which method comprises (a) combining a CUL4A polypeptide, a damaged DNA binding protein 1 (DDB1) polypeptide, and a test substance, under conditions that favor the formation of a CUL4A-DDB1 complex, (b) measuring the amount of CUL4A-DDB1 complex formed under the conditions of (a), and (c) comparing the amount of CUL4A-DDB1 complex formed as measured in (b) in the presence of a test substance to the amount of CUL4A-DDB1 complex formed as measured in (b) in the absence of a test substance, whereby a difference is indicative of the ability of the test substance to modulate CUL4A ubiquitin ligase activity. Such an identified modulator can be a substance that interferes with CUL4A ubiquitin ligase activity.

BRIEF DESCRIPTION OF THE DRAWINGS

FIG. 1A is a set of diagrams of the murine Cul4a genomic locus before and after targeting with a LoxP cassette. FIG. 1B is a set of Southern blots comparing the Cul4a locus in wild-type and floxed heterozygous (f/+) embryonic stem cells. FIG. 1C is a set of agarose gels depicting Cul4a in PCR amplified tail DNA of wild-type (+/+), homozygous floxed (f/f), and heterozygous (f/+) mice (top) and the wild-type and the recombined (null) Cul4a alleles (bottom). FIG. 1D is a set of Western blots depicting CUL4A, CUL4A(Δ), and β-actin levels in tissues and embryonic fibroblasts (MEF) of wild-type (+/+) and knockout (−/−) mice. FIG. 1E is a set of Western blots depicting the interaction between Rbx1 and CUL4A or CUL4A (Δ).

FIG. 2A is a diagram of the Cul4a knockout allele described by Li et al. (*Mol. Cell. Biol.*, 22: 4997-5005 (2002)), indicating a deletion of part of Pcid2. FIG. 2B is a bar graph depicting Pcid2 mRNA expression evaluated by real-time quantitative RT-PCR in wild-type MEFs infected with empty lentivirus (mock), lentivirus encoding short hairpin RNA targeting Pcid2 (sh-Pcid2-1, sh-Pcid2-2), or scrambled sh-Pcid2. FIG. 2C is a graph depicting the growth of MEFs treated as in FIG. 2B.

FIG. 4A is a set of Western blots depicting CUL4A, DDB2, p21, and β-actin levels in control (f/f) and Cul4a knockout (−/−) skin. FIG. 4B is a set of Western blots depicting CUL4B, CUL4A, DDB2, p21, XPC, and β-actin levels in MEFs treated with the indicated lentivirus. FIG. 4C includes autoradiograms indicating DDB2 levels by pulse-chase analysis and a line graph which quantifies the DDB2 turnover. FIG. 4D includes autoradiograms indicating p21 levels by pulse-chase analysis and a line graph which quantifies the p21 turnover. FIG. 4E is a set of Western blots indicating the levels of XPC, ubiquitinated XPC (XPC~Ub$_n$), CUL4A, and histone 3 (H3) in chromatin extracts of UV-irradiated HCT116 cells treated with the indicated lentivirus.

DETAILED DESCRIPTION OF THE INVENTION

Figure 3A:
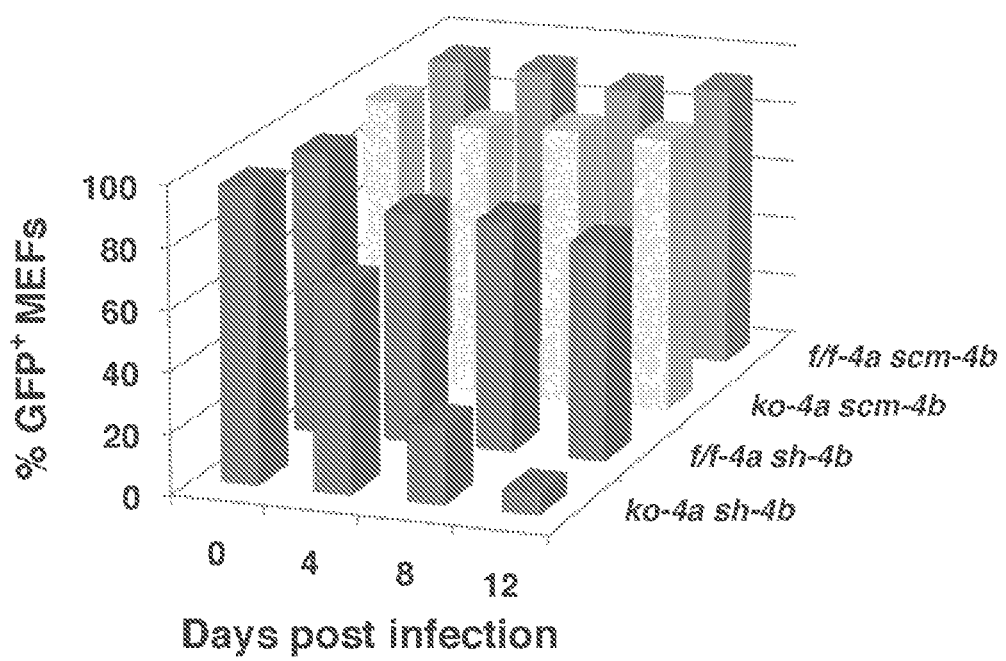
FIG. 3A is a bar graph depicting the percentage of control (f/f-4a) and Cul4a knockout (ko-4a) MEFs infected with a lentivirus encoding GFP and either short hairpin (sh)-4b or scrambled (scm)-4b, at the indicated time point, as determined by FACS.

The invention is based, at least in part, upon the discovery that the DDB1-CUL4A ubiquitin ligase complex is an important cellular target for disease prevention and intervention.

The invention provides a method of preventing or treating a condition associated with DNA damage in an animal, which method comprises administering to an animal in need thereof an effective amount of a substance that interferes with the activity of CUL4A, thereby preventing or treating a condition associated with DNA damage in the animal.

The terms "preventing or treating," "treating," "treatment," "therapy," and "therapeutic treatment" as used herein refer to curative therapy, prophylactic therapy, or preventative therapy. An example of "preventative therapy" is the prevention or lessening of the chance of acquiring a targeted disease (e.g., cancer or other proliferative disease) or related condition thereto. Those in need of treatment include those animals already with the disease or condition as well as those animals prone to have the disease or condition to be prevented. The terms "treating," "treatment," "therapy," and "therapeutic treatment" as used herein also describe the management and care of an animal for the purpose of combating a disease, or related condition, and includes the administration of a composition to alleviate the symptoms, side effects, or other complications of the disease or condition. The animal may be any animal, but preferably is a mammal. In one embodiment of the invention, the mammal is a mouse or other experimental mammal. In another embodiment, the mammal is a human.

The term "DNA damage" is known to one of ordinary skill in the art and refers to any alteration of a DNA molecule relative to its native state. Examples of DNA damage include but are not limited to base pairing mismatches, spontaneous alterations in the chemistry of DNA bases (e.g., tautomeric shifts and deamination), loss of bases (i.e., depurination and depyrimidination), oxygen radical- and ionizing radiation-induced lesions (e.g., thymine damage due to the attack of C-5=C-6 double bond and DNA strand breaks), UV radiation-induced lesions (e.g., cyclobutane pyrimidine dimers and pyrimidine-pyrimidone (6-4) photoproducts), and chemical-induced lesions (e.g., alkylation and inter- or intra-strand crosslinks) (Friedberg and Siede, DNA Repair and Mutagenesis, ASM Press, Washington, D.C. (1995)).

The terms "condition associated with DNA damage" or "disease associated with DNA damage" refer to any condition or disease wherein DNA damage is a causative or contributing factor. In one embodiment, the condition associated with DNA damage is cancer. The cancer may result from a tumor generally found in humans and other mammals or a tumor that arises as the result of inoculation, such as in experimental mammals. Tumors, as is known, include an abnormal mass of tissue that results from uncontrolled and progressive cell division, and is also typically known as a "neoplasm." Many types of cancer are encountered in the human and other animal condition, and there is no intention to limit the application of the methods of the invention to any particular cancer type or variety. The inventive methods are useful for tumor cells and associated stromal cells, solid tumors, and tumors associated with soft tissue, such as, soft tissue sarcoma, for example, in a human. The tumor or cancer can be located in the skin (e.g., melanoma), oral cavity, pharynx, respiratory system, digestive system, bones, joints (e.g., bony metastases), soft tissue, breast, genital system, urinary system, eye, orbit, brain (e.g., glioma), central nervous system, or endocrine system (e.g., thyroid) and is not necessarily the primary tumor or cancer. Tissues associated with the oral cavity include, but are not limited to, the tongue and tissues of the mouth. Cancer can arise in tissues of the digestive system including, for example, the esophagus, stomach, small intestine, colon, rectum, anus, liver, gall bladder, and pancreas. Cancers of the respiratory system can affect the larynx, lung, and bronchus and include, for example, non-small cell lung carcinoma. Tumors can arise in the uterine cervix, uterine corpus, ovary vulva, vagina, prostate, testis, and penis, which make up the male and female genital systems, and the urinary bladder, kidney, renal pelvis, and ureter, which comprise the urinary system. The tumor or cancer can be located in the head and/or neck (e.g., laryngeal cancer and parathyroid cancer). The tumor or cancer also can be located in the hematopoietic system or lymphoid system, and include, for example, lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). Preferably, the tumor or cancer is located in the skin, oral cavity, throat, lung, or liver. Most preferably, the tumor or cancer is located in the skin.

In another embodiment of the invention, the condition associated with DNA damage is a human hereditary disease or an experimental animal model of a human hereditary disease. Examples of human hereditary diseases that may be treated according to the methods provided herein include, but are not limited to, Xeroderma pigmentosum, Cockayne syndrome, Trichothiodystrophy, Fanconi anemia, Ataxia telangiectasia (Louis-Bar Syndrome), and Bloom syndrome. Preferably, the human hereditary disease is Xeroderma pigmentosum.

In yet another embodiment of the invention, the condition associated with DNA damage is aging. Aging includes the natural process of aging in an animal (e.g., a human) as well as accelerated aging which occurs in an animal (e.g., a human) having a heritable mutation in one or more genes that regulates the aging process. A main cause of the aging process in animals is somatic damage due to the effects of reactive oxygen species on cellular DNA. The reactive oxygen species are known to cause myriad DNA lesions such as base modifications, single- and double-strand DNA breaks and inter-strand crosslinks (Hasty et al., Science, 299: 1355-1359 (2003)). Accordingly, the invention provides methods and compositions to enhance DNA repair activity in an animal thereby preventing or treating aging.

In still another embodiment of the invention, the condition associated with DNA damage is prolonged exposure to UV radiation. As discussed above, it is well known that UV radiation induces cyclobutane pyrimidine dimers and pyrimidine-pyrimidone (6-4) photoproducts in DNA. Additional types of DNA damage caused by UV radiation include, without limitation, complex lesions involving purines (e.g., 8,8-adenine dehydrodimer), pyrimidine hydrates (e.g., 5,6-Dihydro-6-hydroxy-cytosine), thymine glycols, and strand breaks (Friedberg and Siede, DNA Repair and Mutagenesis, ASM Press, Washington, D.C. (1995)). Accordingly, the invention also provides methods and compositions to enhance DNA repair activity in an animal thereby preventing or treating a condition associated with prolonged exposure to UV radiation.

In yet another embodiment of the invention, the condition associated with DNA damage is exposure to a chemical carcinogen. As discussed above, chemical carcinogens are known to cause a variety of DNA lesions, including, without limitation, alkylation, inter- or intra-strand crosslinks, and adduct formation. One of ordinary skill in the art is aware of many common chemical carcinogens and is familiar with databases which contain information regarding the carcinogenicity of a given chemical (e.g., The Carcinogenic Potency Project maintained by the University of California-Berkeley and the National Toxicology Program maintained by the United States Department of Health and Human Services). In addition, one of ordinary skill in the art is aware of methods to assess the carcinogenicity of a given chemical (e.g., the Ames test). Accordingly, the invention also provides methods and compositions to enhance DNA repair activity in an animal, thereby preventing or treating a condition associated with prolonged exposure to a chemical carcinogen. In one embodiment, the chemical carcinogen is tobacco smoke. In another embodiment, the chemical carcinogen is aflatoxin.

The invention also encompasses compositions and methods to enhance DNA repair activity in an animal that has been exposed to chemotherapy or radiation therapy. Although a primary goal of chemotherapy or radiation therapy is to induce DNA damage in cancerous cells thereby leading to growth arrest and or cell death, it may be desirable to concurrently enhance DNA repair in non-cancerous cells in the animal exposed to chemotherapy or radiation therapy. One of ordinary skill is aware of chemotherapeutic chemicals that induce DNA damage. Examples of such chemicals include, without limitation, platinum derivatives (e.g., cisplatin, carboplatin, and oxaliplatin), nitrogen mustards (e.g., mechlorethamine, cyclophosphamide, and chlorambucil), and nitrosoureas (e.g., carmustine, lomustine, and ethylnitrosourea).

By "effective amount" or "therapeutically effective amount," it is meant an amount that relieves (to some extent, as judged by a skilled medical practitioner) one or more symptoms of the disease or condition in an animal. Additionally, by "effective amount" or "therapeutically effective amount," it is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered. The precise amount of the composition required to be therapeutically effective will depend upon numerous factors, e.g., such as the specific activity of the active substance, the delivery device employed, physical characteristics of the substance, purpose for the administration, in addition to many patient specific considerations. The determination of amount of a composition that must be administered to be an effective amount or a therapeutically effective amount is routine in the art and within the skill of an ordinarily skilled clinician.

By "administering" or "administered" it is meant that the substance is delivered to an animal in need thereof. The route of administration may be topical, oral, intranasal, parenteral, enteric, rectal, or ocular. In a preferred embodiment of the invention, the substance is delivered topically.

The invention provides a substance that interferes with the activity of CUL4A. As used herein, the terms "substance," "compound," and "therapeutic agent" refer to a chemical compound, a mixture of chemical compounds, a biological macromolecule, or an extract made from biological materials such as bacteria, plants, fungi, or animal (particularly mammalian) cells or tissues that are suspected of having therapeutic properties. The substance, compound, or therapeutic agent can be purified, substantially purified or partially purified.

In one embodiment, the substance is a small molecule chemical compound. As used herein, the term "small molecule" refers to a non-biological substance or compound having a molecular weight of less than about 1,000 g/mol.

In another embodiment, the substance is a polynucleotide. The terms "polynucleotide" and "nucleic acid" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. Suitable nucleotide analogs are well known in the art and are described in, e.g., U.S. Pat. No. 6,107,094 and references therein.

The term "nucleotide" as used herein refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates and the like). Methods of preparing polynucleotides are within the ordinary skill in the art (Sambrook and Russell, Molecular Cloning: A Laboratory Manual, Cold Spring Harbor Laboratory Press, New York (2001)).

The polynucleotide may any inhibitory nucleic acid molecule, including, without limitation, a small interfering RNA (siRNA), a short hairpin RNA (shRNA), an antisense oligonucleotide, an aptamer, or a ribozyme. In a preferred embodiment, the polynucleotide is an siRNA or an shRNA molecule.

A "small interfering RNA" or "short interfering RNA" or "siRNA" or "short hairpin RNA" or "shRNA" is a double-stranded RNA molecule that is complementary to a target nucleic acid sequence, e.g., Cul4a mRNA, and is capable of mediating target-specific nucleic acid degradation. A double-stranded RNA molecule is formed by the complementary pairing between a first RNA portion and a second RNA portion. The length of each portion generally is less than 30 nucleotides (e.g., 29, 28, 27, 26, 25, 24, 23, 22, 21, 20, 19, 18, 17, 16, 15, 14, 13, 12, 11, or 10 nucleotides). In some embodiments, the length of each portion of the siRNA or shRNA is 19 to 25 nucleotides. In some siRNA molecules, the complementary first and second portions of the RNA molecule are the "stems" of a hairpin structure, thereby generating a shRNA molecule. The two portions can be joined by a linking sequence, which can form the "loop" in the hairpin structure. The linking sequence can vary in length. In some embodiments, the linking sequence can be 5, 6, 7, 8, 9, 10, 11, 12, or 13 nucleotides in length. A representative linking sequence is 5'-TTCAGAAGG-3', but any of a number of sequences can be used to join the first and second portions. The first and second portions are complementary but may not be completely symmetrical, as the hairpin structure may contain 3' or 5' overhanging nucleotides (e.g., a 1, 2, 3, 4, or 5 nucleotide overhang).

There are well-established criteria for designing siRNAs or shRNAs (see, e.g., Elbashir et al., Nature, 411: 494-8 (2001); Amarzguioui et al., Biochem. Biophys. Res. Commun., 316 (4): 1050-8 (2004); Reynolds et al., Nat. Biotech., 22(3): 326-30 (2004); Brummelkamp et al., Science, 296: 550-553 (2002)). The sequence of any candidate siRNA or shRNA is generally checked for the possibility of cross-reactivity with other nucleic acid sequences using a suitable program to align the siRNA or shRNA with the nucleic acid sequences contained in a genomic database such as GenBank or Ensembl. Typically, a number of siRNAs or shRNAs will be generated and screened in order to compare their effectivenesses.

The siRNA or shRNA of the invention can be generated by any method including, without limitation in vitro transcription, recombinant production in a host cell, or synthetic chemical means. In one embodiment, the siRNA or shRNA is generated by in vitro transcription of a DNA oligonucleotide template using a recombinant enzyme, such as T7 RNA polymerase. In another embodiment, the siRNA or shRNA is prepared recombinantly in cultured cells, which may be prokaryotic or eukaryotic. Methods of preparing siRNA and shRNA are well known to one of ordinary skill in the art (see, for example, Elbashir et al., Nature, 411: 494-8 (2001); Brummelkamp et al., Science, 296: 550-553 (2002); and Lee et al., Nat. Biotech., 20: 500-5 (2002)).

An "aptamer" or "nucleic acid ligand" or "nucleic acid antibody" as used herein refers to a non-naturally occurring nucleic acid having a desirable action on a target (e.g., CUL4A). Desirable actions include, but are not limited to, binding of the target, catalytically changing the target, reacting with the target in a way which modifies/alters the target or the functional activity of the target, covalently attaching to the target as in a suicide inhibitor, and facilitating the reaction between the target and another molecule. In a preferred embodiment, the desirable action is specific binding affinity for a complex comprising CUL4A, wherein binding of the aptamer, nucleic acid ligand, or nucleic acid antibody occurs through a mechanism which predominantly depends on Watson/Crick base pairing or triple helix binding.

Aptamers include nucleic acids that are identified from a candidate mixture of nucleic acids, wherein the nucleic acid is a ligand of a given target (e.g., CUL4A), by the method comprising (a) contacting the candidate mixture with the target, wherein nucleic acids having an increased affinity to the target relative to the candidate mixture may be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids whereby nucleic acid ligands of the target compound may be identified. This method of identifying candidate aptamers, known as Systematic Evolution of Ligands by Exponential enrichment (SELEX), is well known in the art (see, e.g., U.S. Pat. Nos. 5,270,163 and 5,475,096).

An "antisense oligonucleotide" refers to an oligonucleotide having a nucleotide sequence complementary to a specific nucleotide sequence (i.e., the "sense" target sequence) and capable of hybridizing with the target sequence (e.g., Cul4a mRNA). An antisense oligonucleotide of the invention may comprise DNA, RNA, or mixtures thereof. An antisense oligonucleotide may have 100% sequence complementarity to the target sequence or near complementarity (e.g., 75% or more, 85% or more, or 95% or more). An antisense oligonucleotide of the invention may function by causing a reduction in target mRNA levels through the action of an endonuclease, by blocking or inhibiting translation of the target mRNA, or by inhibiting transcription of the target gene. An antisense oligonucleotide of the invention may comprise nucleic acids which are modified at the base, sugar, and/or phosphate groups as described above. Methods to prepare an antisense oligonucleotide are well known in the art (see, e.g., Crooke and Bennett, Annu. Rev. Pharmacol. Toxicol., 36: 107-129 (1996), and U.S. Pat. No. 6,107,094).

A "ribozyme" refers to an RNA molecule capable of catalyzing a chemical reaction, such as the repeated cleavage of other separate nucleic acid molecules (i.e., having endonuclease activity) in a nucleotide base sequence-specific manner. Such a ribozyme with endonuclease activity may have complementarity in a substrate binding region to a specified gene target (e.g., Cul4a), and also has an enzymatic activity that specifically cleaves RNA or DNA in that target. That is, the ribozyme with endonuclease activity is able to intramolecularly or intermolecularly cleave RNA or DNA and thereby inactivate a target RNA or DNA molecule. This complementarity functions to allow sufficient hybridization of the ribozyme to the target RNA or DNA to allow the cleavage to occur. The degree of complementarity between a ribozyme of the invention and a target RNA or DNA can be 50% or more, 75% or more, 90% or more, or 95% or more. Preferably, the degree of complementarity is 100%. A ribozyme of the invention may comprise nucleic acids which are modified at the base, sugar, and/or phosphate groups as described above. Methods to prepare ribozymes are well known in the art (see, e.g., U.S. Pat. Nos. 4,987,071 and 6,617,438; Robertson and Joyce, Nature, 344: 467-468 (1990)).

The terms "protein," "polypeptide," and "peptide" refer to a polymer of amino acid residues. The protein, polypeptide, or peptide may be full-length or a fragment. The term "fragment" refers to a shorter portion of a full-length protein ranging in size from four amino acid residues to the entire amino acid sequence minus one amino acid residue. In certain embodiments of the invention, a fragment refers to the entire amino acid sequence of a domain of a protein (e.g., N-terminal α-helical region of CUL4A or the BPB (β-propeller domain of DDB1). Proteins, polypeptides, peptides, and fragments thereof may be prepared by chemical synthesis or by recombinant DNA technology using methods within the ordinary skill in the art (Benoiton, Chemistry of Peptide Synthesis, CRC Press, Boca Raton, Fla. (2006); Sambrook and Russell, Molecular Cloning: A Laboratory Manual, Cold Spring Harbor Laboratory Press, New York (2001)).

In certain embodiments of the invention, the substance that interferes with the activity of CUL4A is a polypeptide or a peptide. In some embodiments, the polypeptide or peptide comprises a linear polymer of amino acids. In other embodiments, the polypeptide or peptide comprises a cyclic polymer of amino acids wherein the amino and carboxyl termini of the polymer chain are linked to each other with a peptide bond. The polypeptide or peptide can be any length. The length of the polypeptide or peptide can be 2 amino acids or more, 6 amino acids or more, 10 amino acids or more, or 20 amino acids or more. Alternatively, or in addition, the length of the polypeptide or peptide can be 200 amino acids or less, 100 amino acids or less, 50 amino acids or less, or 40 amino acids or less. Thus, the polypeptide or peptide can have a length bounded by any two of the above endpoints. For example, the polypeptide or peptide can have a length of 2-200 amino acids, 6-100 amino acids, or 10-40 amino acids. In certain embodiments of the invention, the polypeptide or peptide is obtained from a phage display library. Examples of suitable phage display libraries include, but are not limited to, $CX_{10}C/p8+8$ libraries, $NNS_{20}/p8+8$ libraries, and libraries on a knottin scaffold. Methods of screening phage display libraries are known to one of ordinary skill (see, e.g., Barbas et al., Phage Display: A Laboratory Manual, Cold Spring Harbor Laboratory Press, New York (2001)).

The substance can be a polypeptide analog. The term "analog" as used herein in reference to a polypeptide includes any polypeptide having an amino acid residue sequence substantially identical to a polypeptide sequence recited herein in which one or more residues have been conservatively substituted with a functionally similar residue and which displays the activity of the parent polypeptide sequence as described herein. Examples of conservative substitutions include the substitution of one non-polar residue such as isoleucine, valine, leucine or methionine for another; the substitution of lysine for arginine and vice versa such that a positive charge is maintained; the substitution of glutamic acid for aspartic acid and vice versa such that a negative charge is maintained; the substitution of serine for threonine such that a free —OH is maintained; and the substitution of glutamine for asparagine such that a free —NH2 is maintained.

The substance can be a "chemical derivative" of a polypeptide. The term "chemical derivative" as used herein refers to a subject polypeptide having one or more residues chemically derivatized by reaction of a functional side group. In addition to side group derivations, a chemical derivative can have one or more backbone modifications including α-amino substitutions such as N-methyl, N-ethyl, N-propyl, and the like, and α-carbonyl substitutions such as thioester, thioamide, guanidine, and the like. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups, or formyl groups. Free carboxyl groups may be derivatized to form salts, methyl and ethyl esters, or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the invention also include any polypeptide having one or more additions and/or deletions or residues relative to the sequence of a polypeptide whose sequence is recited herein, so long as the requisite activity is maintained.

The substance can be a homolog of the polynucleotide and polypeptide sequences recited herein. The terms "homolog," "homologue," and "homologous" as used herein refer to a polynucleotide or a polypeptide comprising a sequence at least about 80% homologous to the corresponding polynucleotide or polypeptide sequence, preferably at least about 90% homologous to the corresponding polynucleotide or polypeptide sequence, even more preferably at least about 95% homologous to the corresponding polynucleotide or polypeptide sequence, even more preferably at least about 99% homologous to the corresponding polynucleotide or polypeptide sequence. By "corresponding polynucleotide or polypeptide sequence" it is meant, those sequences which align with the sequence of a corresponding polynucleotide or polypeptide sequence wherein the region of alignment is at least about 10 residues (i.e., nucleotides or amino acids) long, at least about 15 residues long, at least about 20 residues long, at least about 30 residues long, at least about 40 residues long, at least about 50 residues long, or at least about 100 residues long. Various methods of sequence alignment are known in the biotechnology arts (see, e.g., Rosenberg, *BMC Bioinformatics* 6: 278 (2005); Altschul et al., *FEBS J.* 272(20): 5101-5109 (2005)).

The substance can be a peptidomimetic. The term "peptidomimetic" refers to a substance which lacks one or more structural elements of a polypeptide that is capable of mimicking or antagonizing the function of the parent polypeptide or fragment from which its design is based. For example, a peptidomimetic may contain non-naturally occurring amino acids or lack peptide bonds. A parent polypeptide may initially be identified as a binding sequence on a protein of interest or may be a naturally occurring polypeptide. Assays to identify peptidomimetics may include a parent polypepeptide as a positive control for comparison purposes, when screening a library, such as a peptidomimetic library. A peptidomimetic library is a library of compounds that may have biological activity similar to that of a parent polypepeptide. Methods of preparing peptidomimetics are within the ordinary skill in the art (Kazmierski, Peptidomimetics Protocols, Humana Press, New Jersey (1998); Kempf, *Methods Enzymol.*, 241: 334-354 (1994); Hruby, *Biopolymers*, 33: 1073-82 (1993); Wiley et al., *Med. Res. Rev.*, 13: 327-384 (1993); Claeson, *Blood Coagul. Fibrinolysis*, 5: 411-436 (1994)).

The substance can be a polysaccharide or a phospholipid.

The term "interferes with the activity of" refers to the ability of a substance to inhibit the expression and/or activity of a targeted molecule(s). Inhibition of expression can be at the mRNA or protein level and can result from decreased synthesis, increased degradation, or both Inhibition of activity refers to a biochemical or biological function of the targeted molecule(s). The degree of inhibition may be partially complete (e.g., 10% or more, 25% or more, 50% or more, or 75% or more), substantially complete (e.g., 85% or more, 90% or more, or 95% or more), or fully complete (e.g., 98% or more, or 99% or more).

CUL4A is a ubiquitin ligase which functions as a component of a multimeric complex wherein the C-terminus of CUL4A interacts with the RING finger protein Rbx1/ROC1/Hrt1 (hereinafter referred to as Rbx1) to recruit the E2 ubiquitin-conjugating enzyme, and the N-terminus of CUL4A interacts with DDB1. DDB1, in turn, acts as an adaptor, binding to DDB1, CUL4A associated factors (DCAFs), which serve as specific substrate receptors (Angers et al., *Nature*, 443: 590-593 (2006); He et al., *Genes Dev.*, 20: 2949-2954 (2006); Higa et al., *Nat Cell Biol.*, 8: 1277-1283 (2006); Jin et al., *Mol. Cell*, 23: 709-721 (2006); Lee and Zhou, *Mol. Cell*, 26: 775-780 (2007)). Substrates for ubiquitination by CUL4A-containing complexes include c-Jun, DDB2, XPC, and p21 (Li et al., *Cell*, 124: 105-117 (2006); Nishitani et al., *J. Biol. Chem.*, 283: 29045-52 (2008)).

As used herein, the term "interferes with the activity of CUL4A" refers to the ability of a substance to inhibit the expression and/or biochemical or biological function of CUL4A. Examples of biochemical functions of CUL4A include, without limitation, binding to DDB1, binding to Rbx1, and having ubiquitin ligase activity (e.g., ubiquitinating and destabilizing p21, ubiquitinating and destabilizing DDB2, and ubiquitinating and destabilizing XPC). In one embodiment, the substance that interferes with the activity of CUL4A disrupts the binding of CUL4A to damaged DNA binding protein 1 (DDB1). Preferably, the substance disrupts the interaction of the N-terminal α-helical region of CUL4A with the BPB β-propeller domain of DDB1. The substance that disrupts the binding of CUL4A to DDB1 may interact directly with CUL4A and/or DDB1 or act indirectly by binding to another component of a CUL4A-DDB1 containing complex.

In one embodiment, the substance that interferes with the activity of CUL4A competitively inhibits the binding of an endogenous CUL4A to DDB1 in an animal. The competitive inhibitor can be a polypeptide or peptidomimetic which comprises a fragment of CUL4A. Preferably, the fragment of CUL4A comprises the N-terminal region of CUL4A (e.g., SEQ ID NO: 7 or SEQ ID NO: 18) or an analog, homolog, derivative, or fragment thereof that functions similarly to the N-terminal region of CUL4A (e.g., SEQ ID NO: 7 or SEQ ID NO: 18).

Examples of biological functions of CUL4A include, without limitation, the regulation of cell proliferation, cell survival, DNA repair, and genomic integrity (Lee and Zhou. *Mol. Cell,* 26: 775-780 (2007)). In a preferred embodiment, the substance that interferes with the activity of CUL4A causes an increase in DNA repair activity. In a particularly preferred embodiment, the substance that interferes with the activity of CUL4A causes an increase in nucleotide excision repair activity, thereby preventing or treating a condition associated with DNA damage in the animal.

Whether the substance interferes with the expression of CUL4A or a biochemical or biological function of CUL4A, the degree of inhibition may be partially complete (e.g., 10% or more, 25% or more, 50% or more, or 75% or more), substantially complete (e.g., 85% or more, 90% or more, or 95% or more), or fully complete (e.g., 98% or more, or 99% or more).

The invention also provides for compositions comprising (a) the substance that interferes with the activity of CUL4A and (b) a carrier. The carrier typically will be liquid, but also can be solid, or a combination of liquid and solid components. The carrier desirably is physiologically acceptable (e.g., a pharmaceutically, pharmacologically, or cosmetically acceptable) carrier (e.g., excipient or diluent). Any suitable physiologically acceptable carrier can be used within the context of the invention, and such carriers are well known in the art. The choice of carrier will be determined, at least in part, by the location of the target tissue and/or cells, and the particular method used to administer the composition.

The composition can further comprise any other suitable components, especially for enhancing the stability of the composition and/or its end use. Accordingly, there is a wide variety of suitable formulations of the composition of the invention. The following formulations and methods are merely exemplary and are in no way limiting.

Compositions comprising nucleic acid molecules typically require additional components to facilitate or enhance intracellular delivery due to the relatively large size, the susceptibility to degradation by endogenous enzymes, and the negative charge of nucleic acid molecules. Examples of suitable components include, but are not limited to liposomes, cationic polymers, and nanoparticles. Alternatively, the nucleic acid molecule may be conjugated, e.g., at its 5'- or 3'-end, to an arginine-rich peptide, cholesterol, or a fatty acid to facilitate or enhance intracellular delivery. Suitable components and conjugates are known to one of ordinary skill in the art (see, e.g., U.S. Pat. Nos. 6,617,438 and 7,402,574; Whitehead et al., *Nat. Rev. Drug Disc.,* 8: 129-138 (2009)).

Formulations suitable for parenteral administration include aqueous and non aqueous, isotonic sterile injection solutions, which can contain anti oxidants, buffers, bacteriostats, and solutes that render the formulation isotonic with the blood of the intended recipient, and aqueous and non aqueous sterile suspensions that can include suspending agents, solubilizers, thickening agents, stabilizers, and preservatives. The formulations can be presented in unit dose or multi dose sealed containers, such as ampules and vials, and can be stored in a freeze dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described. The formulation for parenteral administration can be formulated for intratumoral administration, intravenous injection, intraperitoneal injection, intraocular injection, subcutaneous injection, and the like.

Compositions suitable for enteric administration are formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient. Pharmaceutical preparations for oral use can be obtained through combining active compounds with solid excipients, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as cross-linked polyvinyl pyrrolidone, agar, alginic acid, or a salt thereof, such as sodium alginate. Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Formulations suitable for anal or rectal administration can be prepared as suppositories by mixing the active substance with a variety of bases such as emulsifying bases or water soluble bases. Formulations suitable for vaginal administration can be presented as pessaries, tampons, creams, gels, pastes, foams, or spray formulas containing, in addition to the active ingredient, such carriers as are known in the art to be appropriate.

Formulations suitable for ocular administration can be prepared as an injectables, drops, sprays, or films, by mixing the active substance with a variety of aqueous and non aqueous, isotonic sterile injection solutions, which can contain antioxidants, buffers, bacteriostats, and solutes that render the formulation isotonic with the eye tissue of the intended recipient, and aqueous and non aqueous sterile suspensions that can include suspending agents, solubilizers, thickening agents, stabilizers, and preservatives.

In one preferred embodiment of the invention, the substance that interferes with the activity of CUL4A, alone or in combination with other suitable components, is made into an aerosol formulation to be administered via inhalation. A substance of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used, e.g., to spray mucosa and may be particularly preferable for preventing or treating cancers of the respiratory system or the oral cavity and pharynx.

In a particularly preferred embodiment, the formulation is a sunscreen composition comprising the substance that interferes with the activity of CUL4A and a cosmetically acceptable carrier. Typically, a sunscreen composition is an oil-in-water or water-in-oil emulsion wherein the oil phase comprises one or more sunscreen compounds, solubilizers, silicone emulsifiers, emollients, and other cosmetically acceptable skin conditioning agents. The aqueous phase is predominantly water, but typically comprises additional ingredients such as humectants (e.g., pentylene glycol and glycerine), preservatives, and thickeners. Additional components such as fragrances, dyes, and extracts may be added to either phase or to the emulsion after it is prepared. Similarly, the substance that interferes with the activity of CUL4A of the invention may be added to the oil phase, the aqueous phase, or the emulsion after it is prepared depending upon the physiochemical characteristics of the substance.

The term "sunscreen compound" refers to a compound capable of screening ultraviolet radiation having a wavelength of 280 nm-320 nm (i.e., UV-B) and/or 320 nm-400 nm (i.e., UV-A). The sunscreen compound may be one or more organic chemicals that absorb UV radiation, one or more inorganic chemicals that reflect, scatter, or absorb UV radiation, or any combination thereof. Examples of suitable sunscreen compounds include, without limitation, sulisobenzone, dioxybenzone, methyl anthranilate, 4-aminobenzoic acid (PABA), amyl dimethyl PABA, octyl dimethyl PABA, glyceryl PABA, 2-ethoxyethyl p-methoxycinnamate, diethamolamine p-methoxycinnamate, ethylhexyl p-methoxycinnamate, digalloyl trioleate, ethyl 4-bis(hydroxypropyl)aminobenzoate, 2-ethylhexyl-2-cyano-3,3-diphenylacrylate, 2-ethylhexyl salicylate, homomethyl salicylate, triethanolamine salicylate, 2-phenylbenzimidazole-5-sulfonic acid, red petrolatum, titanium dioxide, zinc oxide, and combinations thereof.

Suitably, the sunscreen composition takes the form of a lotion, an oil, a gel, a solid stick, a spray, or a foam. Sunscreen compositions and methods of preparation are well known to one of ordinary skill in the art and are described in, e.g., U.S. Pat. Nos. 5,587,150; 5,770,183; and 6,033,649.

The invention also includes a method of preventing or treating a condition associated with DNA damage in an animal, which method comprises administering to an animal in need thereof an effective amount of a sunscreen composition comprising a substance that interferes with the activity of CUL4A and a cosmetically acceptable carrier, thereby preventing or treating a condition associated with DNA damage in the animal. In one embodiment, the sunscreen composition of the invention is administered before exposure to UV radiation. Desirably, the sunscreen composition is administered 10 minutes or more, 20 minutes or more, 30 minutes or more, or 60 or more minutes before exposure to UV radiation to prevent or attenuate DNA damage. In another embodiment, the sunscreen composition is administered during exposure to UV radiation to prevent or attenuate DNA damage or to enhance DNA repair. In yet another embodiment, the sunscreen composition is administered after the animal is exposed to UV radiation. Desirably, the sunscreen composition is applied 30 minutes or less, 1 hour or less, 4 hours or less, 12 hours or less, or 24 hours or less after exposure to UV radiation in order to enhance DNA repair.

The invention also provides a method of co-administering a substance that interferes with the activity of CUL4A with a chemotherapeutic agent to an animal in need thereof. By "co-administering" is meant administering the chemotherapeutic agent and the substance that interferes with the activity of CUL4A sufficiently close in time such that the substance that interferes with the activity of CUL4A can enhance the effectiveness of the chemotherapeutic agent. In this regard, the substance that interferes with the activity of CUL4A can be administered first and the chemotherapeutic agent can be administered second, or vice versa. Alternatively, the substance that interferes with the activity of CUL4A and the chemotherapeutic agent can be administered simultaneously.

Any class of chemotherapeutic agent can be co-administered with the substance that interferes with the activity of CUL4A, including without limitation, an antimicrotubule agent, an antimetabolite, an antimitotic, a DNA damaging agent, a proapoptotic, a differentiation inducing agent, an antibiotic, a hormone, and any combination thereof. Suitable chemotherapeutics include, but are not limited to, tyrosine kinase inhibitors (genistein), biologically active agents (TNF, or tTF), radionuclides ($^{131}$I, $^{90}$Y, $^{111}$In, $^{211}$At, $^{32}$P and other known therapeutic radionuclides), adriamycin, ansamycin antibiotics, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, meplhalan, methotrexate, rapamycin (sirolimus) and derivatives, mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, transplatinum, anti-vascular endothelial growth factor compounds ("anti-VEGFs"), anti-epidermal growth factor receptor compounds ("anti-EGFRs"), 5-fluorouracil, and the like. A dose of one or more chemotherapeutic agents can be administered according to the inventive method. The type and number of chemotherapeutic agents used in the inventive method will depend on the standard chemotherapeutic regimen for a particular tumor type. In other words, while a particular cancer may be treated routinely with a single chemotherapeutic agent, another may be treated routinely with a combination of chemotherapeutic agents. The chemotherapeutic agent is administered in a dose sufficient to treat the cancer (e.g., cancer-treatment effective amount of a chemotherapeutic agent). A clinician skilled in the art can determine the therapeutically effective amount of a composition in order to treat or prevent a particular disease condition, or disorder when it is administered.

The invention also provides a method of identifying a substance that modulates CUL4A ubiquitin ligase activity, which method comprises (a) combining a CUL4A polypeptide, a DDB1 polypeptide, and a test substance, under conditions that favor the formation of a CUL4A-DDB1 complex, (b) measuring the amount of CUL4A-DDB1 complex formed under the conditions of (a), and (c) comparing the amount of CUL4A-DDB1 complex formed as measured in (b) in the presence of a test substance to the amount of CUL4A-DDB1 complex formed as measured in (b) in the absence of a test substance, whereby a difference is indicative of the ability of the test substance to modulate CUL4A ubiquitin ligase activity.

The modulator of CUL4A ubiquitin ligase activity to be identified by the inventive method can be a positive regulator, i.e., a substance that increases the ubiquitin ligase activity of CUL4A. The modulator may increase the ubiquitin ligase activity of CUL4A by about 1.5-fold or more, about 2-fold or more, about 3-fold or more, about 4-fold or more, about 5-fold or more, about 10-fold or more, about 15-fold or more, or about 20-fold or more, compared to ubiquitin ligase activity in the absence of the modulator.

The modulator of CUL4A can be a negative regulator, i.e., a substance that decreases, inhibits, or interferes with CUL4A ubiquitin ligase activity. Accordingly, the invention provides a method of identifying a substance that interferes with the ubiquitin ligase activity of CUL4A, which method comprises (a) combining a CUL4A polypeptide, a DDB1 polypeptide, and a test substance, under conditions that favor the formation of a CUL4A-DDB1 complex, (b) measuring the amount of CUL4A-DDB1 complex formed under the conditions of (a), and (c) comparing the amount of CUL4A-DDB1 complex formed as measured in (b) in the presence of a test substance to the amount of CUL4A-DDB1 complex formed as measured in (b) in the absence of a test substance, whereby a decrease in the amount of CUL4A-DDB1 complex formed in the presence of a test substance is indicative of the ability of the test substance to interfere with CUL4A ubiquitin ligase activity.

Desirably, the substance that interferes with the activity of CUL4A inhibits ubiquitin ligase activity by at least 25% (e.g., 25% or more, 35% or more, or 45% or more) compared to ubiquitin ligase activity in the absence of the interfering substance. Preferably, the substance that interferes with the activity of CUL4A inhibits ubiquitin ligase activity by at least 50% (e.g., 50% or more, 60% or more, or 70% or more) compared to ubiquitin ligase activity in the absence of the interfering substance. Most preferably, the substance that interferes with the activity of CUL4A inhibits ubiquitin ligase activity by at least 75% (e.g., 75% or more, 85% or more, or 95% or more) compared to ubiquitin ligase activity in the absence of the interfering substance.

Methods for screening for substances capable of modulating a protein-protein interaction are well known to one of ordinary skill in the art. For example, the test substance may be screened for the ability to modulate a CUL4A-DDB1 complex using traditional art-recognized assays such as enzyme-linked immunosorbant assays (ELISA), enzyme-linked immunosorbent spot (ELISPOT assays), radioimmunoassay, or BIACORE assays, which allow for the determination of binding affinities in the presence and absence of a test substance. Preferably, the screening occurs in a multiwell plate as part of a high throughput screen. Suitable screening assays are described in more detail in the Examples.

The CUL4A polypeptide can be a full-length CUL4A polypeptide (e.g., SEQ ID NO: 1), or a fragment of a full-length CUL4A polypeptide. The fragment of a full-length CUL4A polypeptide can have a length of 75 amino acids or more, 100 amino acids or more, 125 amino acids or more, or 150 amino acids or more. Alternatively, or in addition, the fragment of a full-length CUL4A polypeptide can have a length of 750 amino acids or less, 600 amino acids or less, 450 amino acids or less, or 300 amino acids or less. Thus, the fragment of a full-length CUL4A polypeptide can have a length bounded by any two of the above endpoints. For example, the fragment of a full-length CUL4A polypeptide can have a length of 75-750 amino acids, 150-450 amino acids, or 125-300 amino acids. Desirably, the fragment of a full-length CUL4A polypeptide comprises the entire N-terminal a-helical region of CUL4A (e.g., SEQ ID NO: 7) and/or retains the ability to bind to a DDB1 polypeptide. Additional exemplary fragments of a full-length CUL4A polypeptide comprising the entire N-terminal a-helical region of CUL4A and which bind to a DDB1 polypeptide include fragments comprising SEQ ID NO: 5 or SEQ ID NO: 6.

Figure 12:
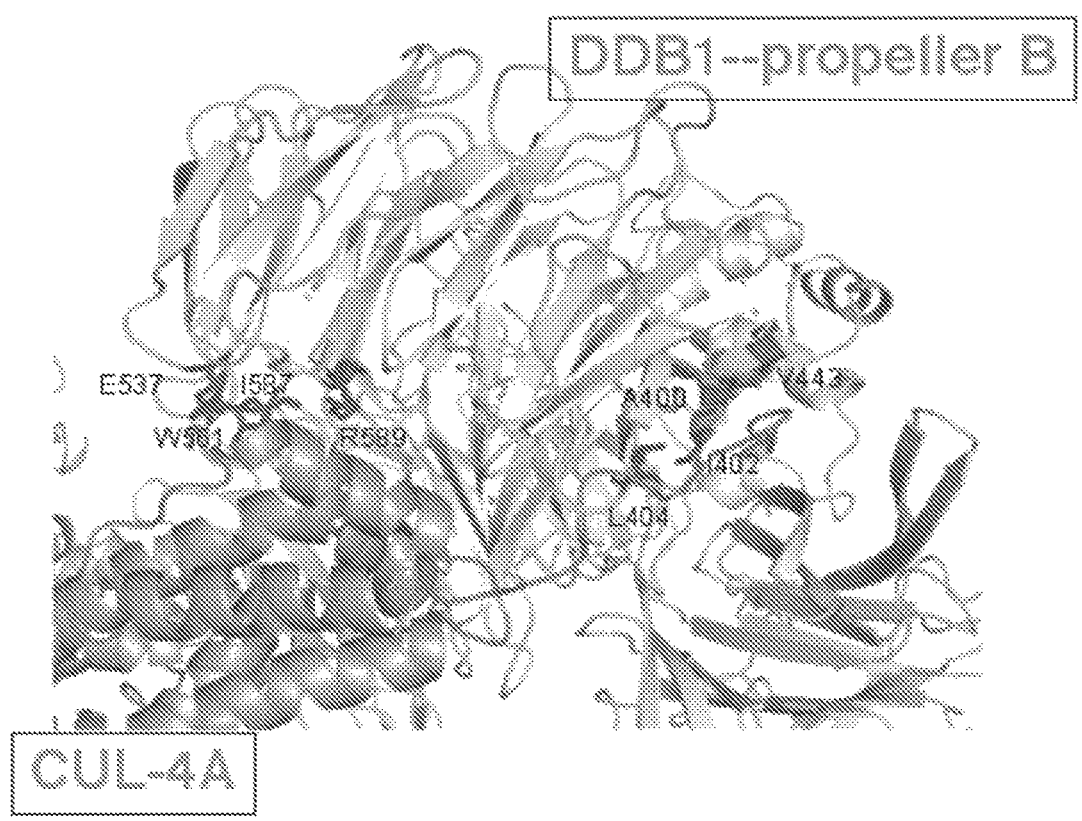
FIG. 12 is a ribbon diagram representing the DDB1-CUL4A interaction interface, wherein the 8 residues on the DDB1-BPB β-propeller region (i.e., A400, 1402, L404, V443, E537, W561, 1587, and R589) that make direct contact with CUL4A are indicated.

The DDB1 polypeptide can be a full-length full-length DDB1 polypeptide (e.g., SEQ ID NO: 3), or a fragment of a full-length DDB1 polypeptide. The fragment of a full-length DDB1 polypeptide can have a length of 150 amino acids or more, 200 amino acids or more, 250 amino acids or more, or 300 amino acids or more. Alternatively, or in addition, the fragment of a full-length DDB1 polypeptide can have a length of 800 amino acids or less, 600 amino acids or less, or 400 amino acids or less. Thus, the fragment of a full-length DDB1 polypeptide can have a length bounded by any two of the above endpoints. For example, the fragment of a full-length DDB1 polypeptide can have a length of 150-800 amino acids, 200-600 amino acids, or 250-400 amino acids. Desirably, the fragment of a full-length DDB1 polypeptide comprises the BPB β-propeller domain of DDB1 (e.g., SEQ ID NO: 8) and/or retains the ability to bind to a CUL4A polypeptide. Preferably, the fragment of a full-length DDB1 polypeptide comprises amino acid residues A400, 1402, L404, V443, E537, W561, 1587, and R589, which have been identified as forming direct contacts with CUL4A (Angers et al., *Nature*, 443: 590-593 (2006); Li et al., *Cell*, 124: 105-117 (2006)) (FIG. 12).

The CUL4A polypeptide and/or the DDB1 polypeptide can be linked to a processing or identification sequence, such as a protein purification tag. Examples of suitable protein purification tags include, but are not limited to GST, FLAG, and polyhistidine. Preferably, the protein purification tag is GST or FLAG. Most preferably, the protein purification tags of the CUL4A polypeptide and the DDB1 polypeptide are different.

In a preferred embodiment of the method of identifying a substance that modulates CUL4A ubiquitin ligase activity, the CUL4A polypeptide and the DDB1 polypeptide are tagged with different molecules, and either the tagged CUL4A polypeptide or the tagged DDB1 polypeptide is immobilized to a laser excitable donor bead, and the other of the CUL4A polypeptide or the DDB1 polypeptide not immobilized to the donor bead is immobilized to an acceptor bead comprising a thioxene derivative capable of generating chemiluminescence in the presence of singlet oxygen. A detailed description of this embodiment is set forth in the Examples.

The test substance that modulates CUL4A ubiquitin ligase activity can be any suitable substance. For example, the test substance that modulates CUL4A ubiquitin ligase activity can be a small molecule (such as obtained from a chemical library) or a peptide (such as displayed from the surface of a phage, e.g., in a phage display library).

The following examples further illustrate the invention but should not be construed as in any way limiting its scope.

Example 1

This example demonstrates the generation of a Cul4 knockout (Cul4$^{-/-}$) mouse and compares its phenotype to a previously disclosed Cul4a knockout mouse.

To generate the floxed Cul4a allele, the 129 genomic library (Invitrogen) was screened with a Cul4a cDNA probe. Five BAC clones were identified, and clone #297L07 was used to generate the final targeting construct. The targeting vector was generated by placing a LoxP site and the pSV-FLP-Cre neomycin resistance cassette 1.1 kb upstream of exon 17 and another LoxP site 300 bps downstream of exon 19. The 5' and 3' homologous arms were 3 kb and 5 kb, respectively, and were generated by EXL long-range PCR (Stratagene) from the BAC clone. Following electroporation and G418 selection, ES clones that underwent homologous recombination were identified by Southern blotting. Homologous recombination at the 5' end was assessed by digesting ES cell genomic DNA with BamHI and hybridizing the Southern blot with a probe immediately upstream of the 5' homologous arm. The wild-type allele yielded an 11 kb band whereas the targeted allele produced a 7.3 kb band due to an extra BamHI site in the pSV-FLP-Cre vector. Homologous recombination at the 3' end was determined by digestion with both SacI and PacI, and hybridization with a probe immediately downstream of the 3' homologous arm. The wild-type allele showed a 9 kb band compared to a 7 kb band in the targeted allele. Two positive clones (#379 and #395) after homologous recombination were used to generate chimeric mice by blastocyst injection.

The deleted Cul4a allele was created by germline-induced deletion of exons 17 to 19 by crossing floxed Cul4a mice with the E2A-Cre transgenic line (Lakso et al., *Proc. Natl. Acad. Sci. U.S.A.*, 93: 5860-5865 (1996)). Transmission of the targeted loci was confirmed by Southern blotting and PCR. All mutant animals were backcrossed to C57BL/6J for 12 generations.

Analysis of protein expression was performed by extracting proteins from tissues of Cul4a$^{-/-}$, Cul4a$^{f/f}$, or wild-type littermates using the Cellytic™ MT Mammalian Tissue Lysis/Extraction Reagent (Sigma-Aldrich, St. Louis, Mo.). Tissue and MEF extracts were immunoblotted with antibodies against CUL4A (C-19, Santa Cruz Biotechnology, Santa Cruz, Calif.) and β-actin (Sigma, St. Louis, Mo.).

Short hairpin (sh) RNAs for gene targeting were as follows: murine sh-Cul4b was 5'-GTAGTAACGAGAGAGAAGACT-3' (SEQ ID NO: 9); murine sh-Pcid2-1 was 5'-GGCAAAG-CACGAGACGTTCTT-3' (SEQ ID NO: 10); murine sh-Pcid2-2 was 5'-GATGAAATGTTTGCAGCTCATT-3' (SEQ ID NO: 11); murine sh-p21 was 5'-GAGAACGGTG-GAACTTTGACTT-3' (SEQ ID NO: 12); scrambled sh-Cul4b was 5'-GTCGCAGCAATAAATACGGCT-3' (SEQ ID NO: 13); and human sh-Cul4a was 5'-GAAGCTGGT-CATCAAGAAC-3' (SEQ ID NO: 14). shRNAs were subcloned into the FUGW lentiviral vector and expressed under the U6 promoter (Sui and Shi, *Methods Mol. Biol.*, 309: 205-218 (2005)). Recombinant lentiviruses were generated for infection of MEFs or HCT116 cells.

The CUL4A(Δ) mutant (deletion of residues 585-727) was generated by two consecutive PCR reactions and cloned into the pcDNA3 vector with following PCR primers: the upstream PCR primer was 5'-GCGATATCCGCGGAC-GAGGGCCCTCG-3' (SEQ ID NO: 15); the 1st downstream primer was 5'-CATATAGTCTCTGTCTATAAG TGACT-CAATCCTTTTTTTCAAATCTCCAGGCTC-CTTAAAGTCCGCCTTCAGC-3' (SEQ ID NO: 16), and the 2nd downstream primer was 5'-GCTCTAGATCATGC-CACGT AGTGGTACTGATTTGGACT-GTCTTTGTCTCGTTCCATATAGTCTCTGTCTATAAG-3' (SEQ ID NO: 17). The CUL4A interaction with Rbx1 was assessed in immunoprecipitates of 293T cells transiently transfected with a MYC-tagged CUL4A or a CUL4A mutant (deletion of residues 585-727) (CUL4A(Δ)), which was generated by PCR and cloned into the pcDNA3-MYC vector, with or without cotransfection of FLAG-tagged Rbx1. Immunoprecipitation was performed with anti-MYC antibodies, and subsequent Western blotting was performed with anti-MYC (Ab-1) and anti-FLAG (M2) antibodies obtained from commercial sources.

To investigate the physiological role of CUL4A in DNA repair and tumorigenesis, conditional Cul4a knockout mice were generated using the Cre/lox strategy. Exons 17-19, which span the essential cullin homology domain and neddylation site, were floxed by homologous recombination in embryonic stem (ES) cells (FIG. 1A). Southern blotting confirmed the presence of the targeted Cul4a locus in floxed heterozygous (f/+) embryonic stem cells (FIG. 1B), and PCR analysis identified the wild-type, floxed, and recombined Cul4a allele in mouse tail DNA (FIG. 1C). Homozygous Cu/4a$^{f/f}$ mice were healthy and phenotypically indistinguishable from their wild-type littermates. Cul4a$^{-/-}$ mice were subsequently generated by interbreeding Cu/4a$^{f/f}$ mice with E2A-Cre transgenic mice (Lakso et al., *Proc. Natl. Acad. Sci. U.S.A.*, 93: 5860-5865 (1996)), and the absence of full-length CUL4A protein was confirmed by Western blotting in multiple tissues and MEFs (FIG. 1D). A C-terminal truncated CUL4A (designated CUL4A(Δ)) was detectable, but at markedly reduced levels (8%) compared to that of wild-type CUL4A, and failed to interact with Rbx1 for recruitment of the E2 ubiquitin-conjugating enzyme (FIG. 1E).

The Cul4a$^{-/-}$ mice described in this Example were viable and displayed no overt developmental abnormalities throughout their life span. This result is in stark contrast with the embryonic lethality of the published Cul4a exon 1 deletion strain (Li et al., *Mol. Cell. Biol.*, 22: 4997-5005 (2002)). However, the exon 1 targeting construct of Li et al. also abolished expression of the Pcid2 gene that resides on the complementary stand adjacent to Cul4a exon 1. Pcid2 encodes a protein with a PCI domain, which is conserved among the essential subunits of the 26S proteasome, COP9 signalosome, and translation initiation factor 3 complexes (Hofmann and Bucher, *Trends Biochem. Sci.*, 23: 204-205 (1998)). The exon 1 targeting allele by Li et al. deleted a 529 base pair region upstream of the first Pcid2 exon, leaving only 4 base pairs upstream of the ATG translation initiation codon (FIG. 2A). Silencing of Pcid2 expression in primary mouse embryonic fibroblasts (MEFs) by lentiviral Pcid2 short hairpin (sh) RNA resulted in a rapid loss of viability (FIG. 2B). In contrast, growth arrest or cell death was not observed in Cul4a$^{-/-}$MEFs (FIG. 3A). Therefore, the embryonic lethality phenotype observed by Li et al. is likely due to the coincidental abrogation of the essential Pcid2 gene that resides on the complementary strand adjacent to Cul4a.

In mammals, the two Cul4 genes (i.e., Cul4a and Cul4b) are broadly co-expressed and assemble structurally similar ubiquitin ligases. Therefore, CUL4B could complement the loss of CUL4A and thus ensure survival of the Cul4a$^{-/-}$ mice. Accordingly, silencing of Cul4b in Cul4a$^{-/-}$ MEFs led to a dramatic reduction of BrdU incorporation and loss of cell viability (FIGS. 3A and 3B), consistent with what previously was observed with Ddb1$^{-/-}$ MEFs (Cang et al., *Cell*, 127: 929-940 (2006)), and in accordance with the fact that both CUL4 proteins must be inactivated to abolish CUL4 ubiquitin ligase activity (Higa et al., *Nat. Cell Biol.*, 5: 1008-1015 (2003); Hu et al., *Nat. Cell Biol.*, 6: 1003-1009 (2004)).

This example demonstrated the generation of a Cul4 knockout (Cul4$^{-/-}$) mouse wherein the Pcid2 locus is not modified.

Example 2

This example demonstrates the enhanced stability of DDB2, p21, and XPC in Cul4a deficient cells.

MEFs were isolated from embryonic day (E) 13.5 wild-type or Cul4a knockout embryos. shRNAs for murine Cul4b and Pcid2 as well as scrambled controls were subcloned into the FUGW lentiviral vector and expressed under the U6 promoter as described in Example 1. Recombinant shCul4b and shPcid2 lentiviruses were generated for infection of primary Cu/4a$^{f/f}$ and Cul4a$^{-/-}$ MEF cells. shRNA-containing FUGW lentivirus were added onto Cu/4a$^{f/f}$ and Cul4a$^{-/-}$ MEFs every 12 hours for 36 hours. The cells were harvested 48 hours post-infection, and Western blotting was performed on MEF extracts using antibodies against CUL4A (C-19, Santa Cruz Biotechnology), CUL-4B, DDB2 (Cell Signaling Technology, Danvers, Mass.), p21 (Santa Cruz Biotechnology), XPC, histone H3, and β-actin (Sigma, St. Louis, Mo.).

The half-life of DDB2 was determined by pulse-chase analysis in Cul4a$^{-/-}$ and Cu/4a$^{f/f}$ MEFs and quantified using a phosphorimager scanner. The half-life of p21 was assayed by cyclohexamide (CHX) chase in Cul4a$^{-/-}$ and Cu/4a$^{f/f}$ MEFs and quantified by measuring immunoblot signals, which were plotted on logarithmic scale as a function of time.

Figure 6:
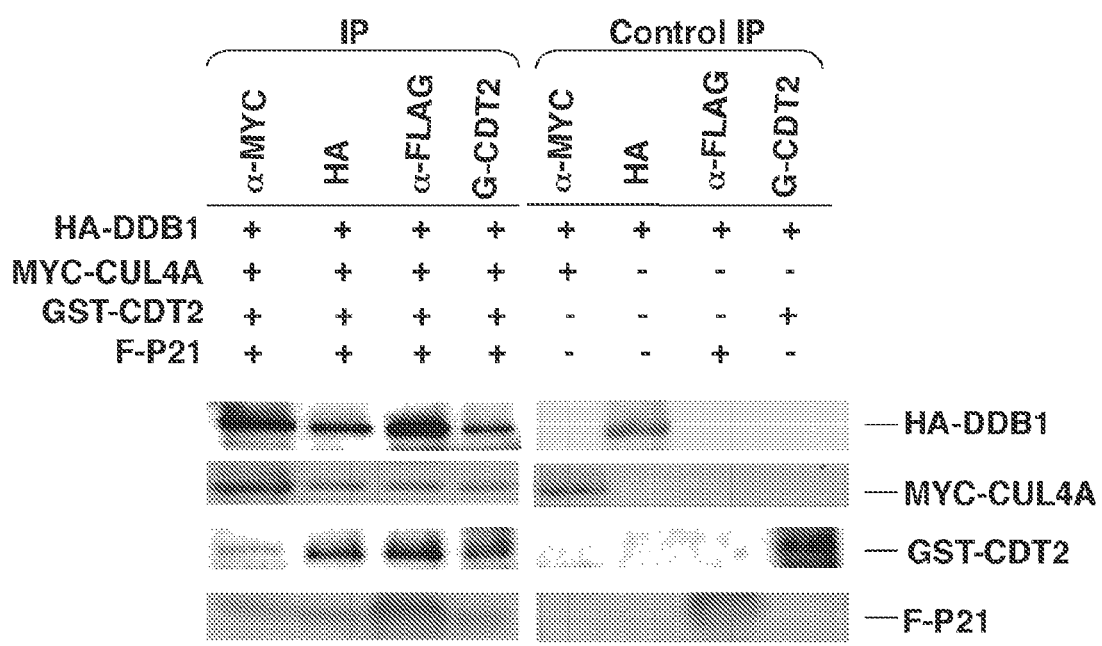
FIG. 6 is a set of Western blots depicting the interactions between p21 and components of the CUL4A-DDB1 ubiquitin ligase complex in immunoprecipitates of 293T cells transfected with the indicated plasmids.

The p21 interaction with components of the CUL4A-DDB1 complex was assessed in immunoprecipitates of 293T cells transiently transfected or not transfected with a MYC-tagged CUL4A, HA-tagged DDB1, GST-tagged CDT2, and FLAG-tagged p21. Immunoprecipitation and subsequent Western blotting was performed with the appropriate antibodies as depicted in FIG. 6.

XPC ubiquitination was determined in HCT116 cells following UV irradiation. HCT116 cells were infected with lentiviral shCul4a or control FUGW for 48 hours, UV irradiated at 10 J/m$^2$ and harvested at 0 hr, 0.5 hr, 1 hr, and 2 hr post-UV. The chromatin-bound extracts were prepared and subjected to immunoblotting.

Figure 3B:
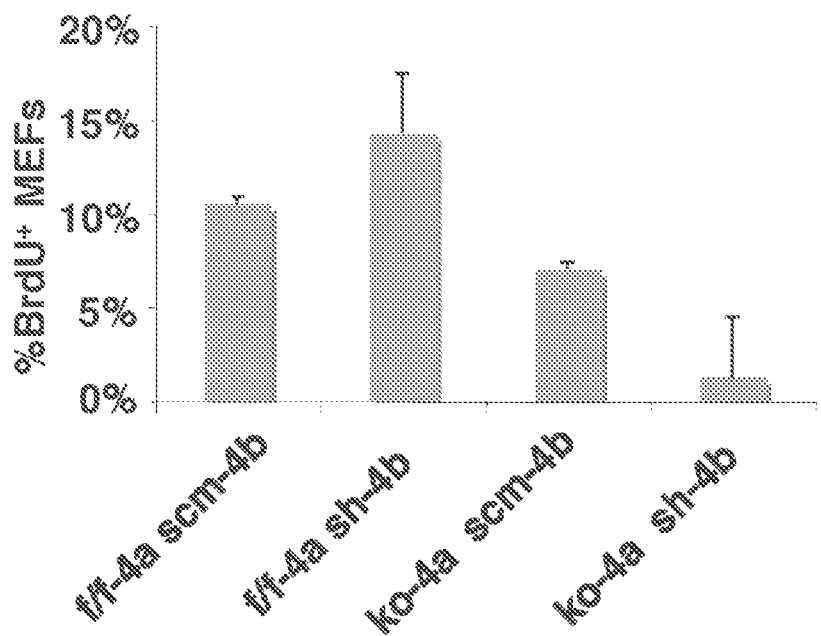
FIG. 3B is a bar graph depicting BrdU incorporation into the MEFs described in FIG. 3A, as determined by counting BrdU$^+$ cells in microscopic fields.
Figure 5A:
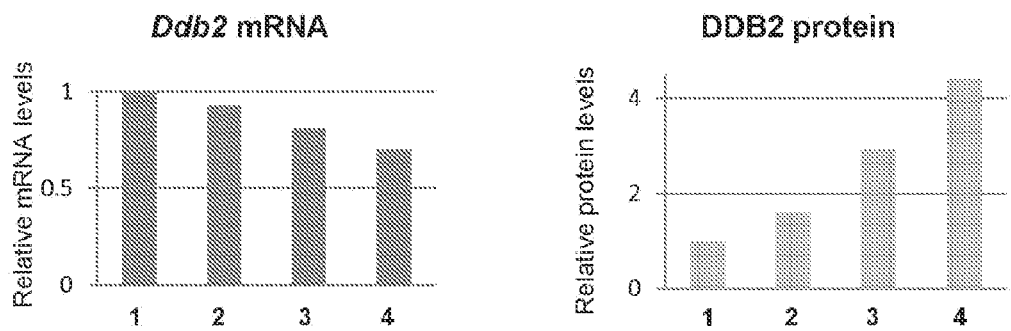
FIGS. 5A-C include bar graphs quantifying mRNA levels of Ddb2 (A), p21 (B), and Xpc (C) as determined by real-time quantitative RT-PCR in Cul4a$^{f/f}$ (1), Cu/4b$^{k/d}$ (2), Cul4a$^{−/−}$ (3), and Cul4a$^{−/−}$; Cul4b$^{k/d}$ (4) MEFs, and bar graphs quantifying the protein levels of DDB2 (A), p21 (B), and XPC (C) determined by the Western blots, wherein the column numbers correspond to the lane numbers in FIG. 4B.
Figure 5B:
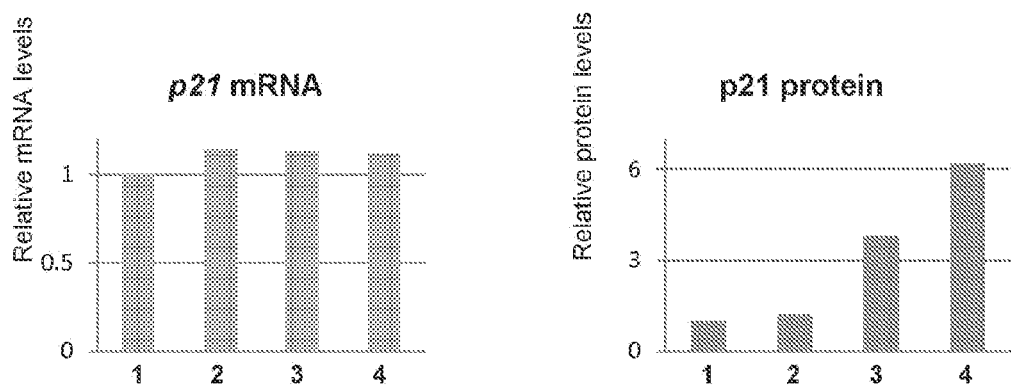

Higher steady-state levels of DDB2 protein were observed in the epidermis of Cul4a$^{-/-}$ mice (FIG. 4A) and Cul4a$^{-/-}$ MEFs (FIG. 4B), and the half-life of DDB2 was prolonged in primary MEFs derived from E13.5 Cul4a$^{-/-}$ embryos as determined by pulse-chase analysis (FIG. 4C). To determine the relative contributions of CUL4A and CUL4B in DDB2 degradation, lentiviral shRNA against mouse Cul4b was generated for infection of early passage (P3) primary Cu/4a$^{f/f}$ and Cul4a$^{-/-}$ MEFs. shCul4b effectively reduced over 93% of mouse CUL4B, yet had only a marginal effect on DDB2 levels (FIG. 4B, FIG. 5A). In contrast, Cul4a knockout or abrogation of both Cul4a and Cul4b resulted in a 3- to 4.5-fold upregulation of DDB2 protein, but not mRNA (FIG. 4B, FIG. 5A). DDB2 mRNA levels remained unaltered or even slightly decreased in response to Cul4a knockout or Cul4b silencing (FIG. 5A).

p21 protein, but not mRNA, also accumulated in Cul4a$^{-/-}$ skin (FIG. 4A, FIG. 5B) and primary MEFs (FIG. 4B) as a result of increased half-life of p21 upon CUL4A deletion (FIG. 4D). Silencing of Cul4b by RNAi had little effect, underscoring the predominant role of CUL4A in controlling the stability of not only DDB2 and XPC but also p21 (FIG. 4B). While simultaneous inactivation of both Cul4a and Cul4b resulted in further accumulation of p21, direct comparison of p21 degradation with that of individual Cul4a or Cul4b inactivation could not be made due to the rapid growth arrest of Cul4a$^{-/-}$ MEFs in which Cul4b was knocked down (FIGS. 3A and 3B). Consistently, p21 was physically present in the CUL4A-DDB1 complex by co-immunoprecipitation (FIG. 6).

Figure 5C:
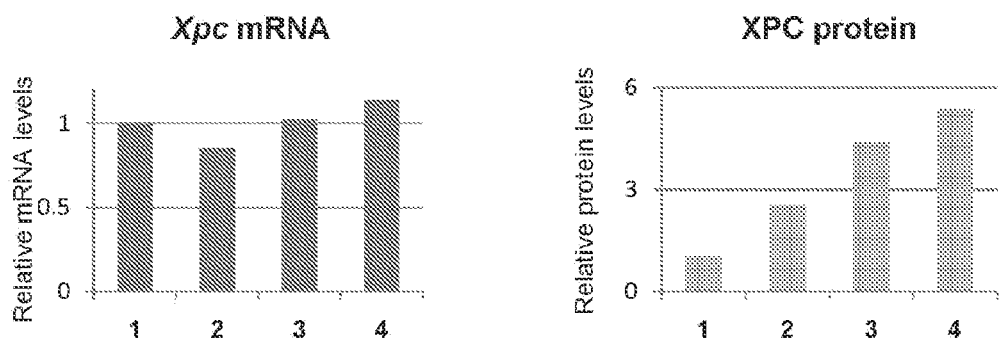

XPC is a rate-limiting factor for the DNA damage recognition step of GGR, and also is a direct ubiquitination target of CUL4A-DDB1-DDB2 E3 ligase (Friedberg et al., DNA Repair and Mutagenesis, 2nd Edition ASM Press, Washington, D.C. (2006); Sugasawa et al., *Cell*, 121: 387-400 (2005)). Interestingly, under normal conditions, the steady-state levels of XPC protein, but not mRNA, increased 4.4-fold upon Cul4a deletion in primary MEF cells, while Cul4b knockdown had a marginal effect on XPC accumulation (FIG. 4B, compare lanes 1-3, FIG. 5C). Therefore, Cul4a$^{-/-}$ MEFs accumulated not only DDB2, but also the rate-limiting XPC DNA damage sensor for damage recognition and GGR.

Upon UV irradiation, the DDB1-DDB2 complex immediately recognizes damaged DNA and helps recruit the XPC-HHR23B complex to DNA damage sites through direct binding to XPC (Fitch et al., *J. Biol. Chem.*, 278: 46906-46910 (2003)). XPC is then ubiquitinated on DNA by the CUL4A-DDB1-DDB2 E3 ligase, and subsequently de-ubiquitinated, rather than undergoing proteasomal-dependent degradation (Sugasawa et al., *Cell*, 121: 387-400 (2005)). The physiological role of XPC ubiquitination on GG-NER has yet to be determined. Therefore, the effect of CUL4A ablation on XPC binding to chromatin and modification by ubiquitin upon UV irradiation was assessed. Since the available XPC antibodies were unable to detect ubiquitinated mouse XPC in MEFs, CUL4A was depleted by lentiviral shRNA in human HCT116 cells. As shown in FIG. 4E, the association of XPC with chromatin increased upon CUL4A silencing by lentiviral shRNA, consistent with higher XPC levels available in the absence of Cul4a (FIG. 4B). Furthermore, CUL4A depletion led to a dramatic inhibition of XPC ubiquitination on chromatin post-UV (FIG. 4E). Collectively, these results demonstrated a specific role of CUL4A in controlling XPC levels under normal conditions and XPC ubiquitination on chromatin in response to UV irradiation. Moreover, CUL4A was primarily responsible for governing the ubiquitination of DDB2 and XPC, while CUL4B played a lesser, if any, role in these processes.

The results of this example reflected the enhanced stability of DDB2, p21, and XPC in Cul4a deficient cells.

Example 3

This example demonstrates enhanced UV-damaged DNA binding (UV-DDB) and global genomic repair (GGR) activities in Cul4a deficient cells.

For the damaged DNA binding assay of UV-DDB activity, 2 µg of whole cell extract was incubated with a $^{32}$P-labeled DNA probe that was UV-irradiated at 5000 J/m$^2$, and binding was assessed by electrophoretic mobility shift assay (Chen et al., *J. Biol. Chem.*, 276: 48175-48182 (2001)).

Figure 7A:
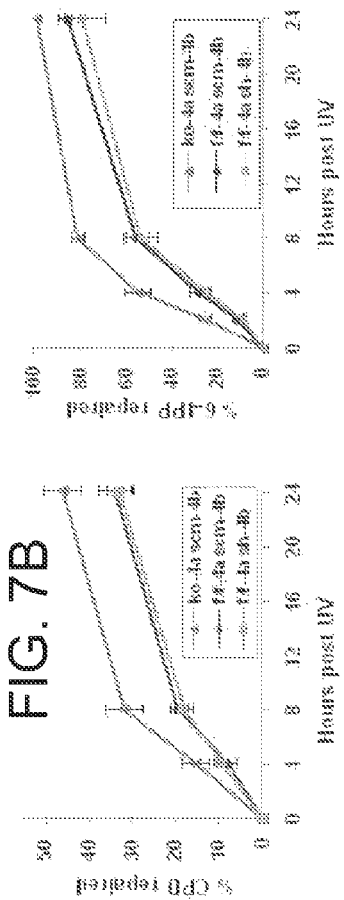
FIG. 7A is an image of an electrophoretic mobility shift assay of UV-DDB activity in control (Cul4a$^{f/f}$) and knockout (Cul4a$^{−/−}$) MEFs. The label "B" indicates the DDB-DNA complex.
Figure 7B:
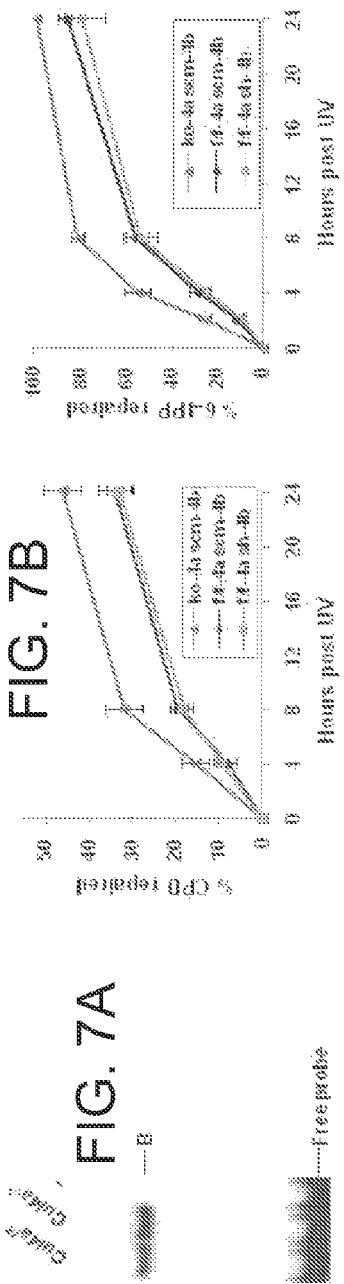
FIG. 7B is a set of line graphs depicting repair of UV-induced cyclobutane pyrimidine dimers (CPDs) and 6-4 photoproducts (6-4PPs) in MEFs treated with the indicated lentivirus.

The GGR ELISA assay of CPD and 6-4PP removal was performed as previously described (Chen et al., 2006) in primary Cul4a$^{-/-}$ (ko-4-a scm-4b), Cu/4b$^{k/d}$ (f/f-4a sh-4b), and control Cu/4a$^{f/f}$ (f/f-4a scm-4-b) MEFs (FIG. 7B, ko, knockout; k/d, knockdown; scm, scramble). Briefly, exponentially growing MEF cells were irradiated with 10 J/m$^2$ UV-C (254 nm) and either harvested immediately (0 hr) or allowed to repair for the duration indicated in FIG. 7B. Genomic DNA was isolated and quantified via liquid scintillation and fluorometric measurements of Hoechst-stained DNA. Denatured genomic DNA was fixed to each well of protamine sulfate-coated 96-well plates and sequentially incubated with monoclonal antibody specific for 6-4PPs (64M-2, 1:5000) or CPDs (1:5000), biotin-F(ab')2 fragment of anti-mouse IgG (H+L) (1:2000, Zymed) and peroxidase-Streptavidin (1:10,000, Zymed) for 30 min at 37° C. The wells were washed with PBS-Tween and 0.1 M citrate-phosphate buffer and incubated with the substrate solution (0.1 M citrate-phosphate buffer, 0.1 mg/mL tetramethylbenzidine [TMB], 0.03% H$_2$O$_2$) at room temperature for 30 min. The enzyme reaction was terminated by adding 50 µl 1M H$_3$PO$_4$ to each well. A450 was determined using a plate reader (Molecular Devices).

Figure 7C:
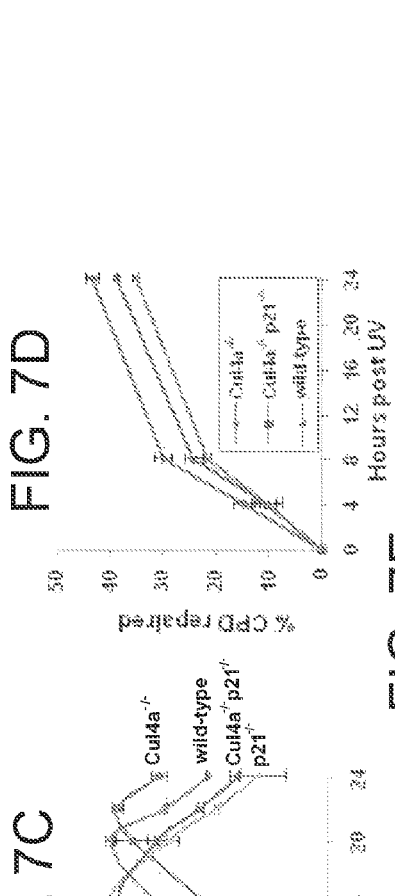
FIG. 7C is a line graph depicting DNA synthesis in synchronized MEFs of the indicated genotypes following UV-irradiation.
Figure 8:
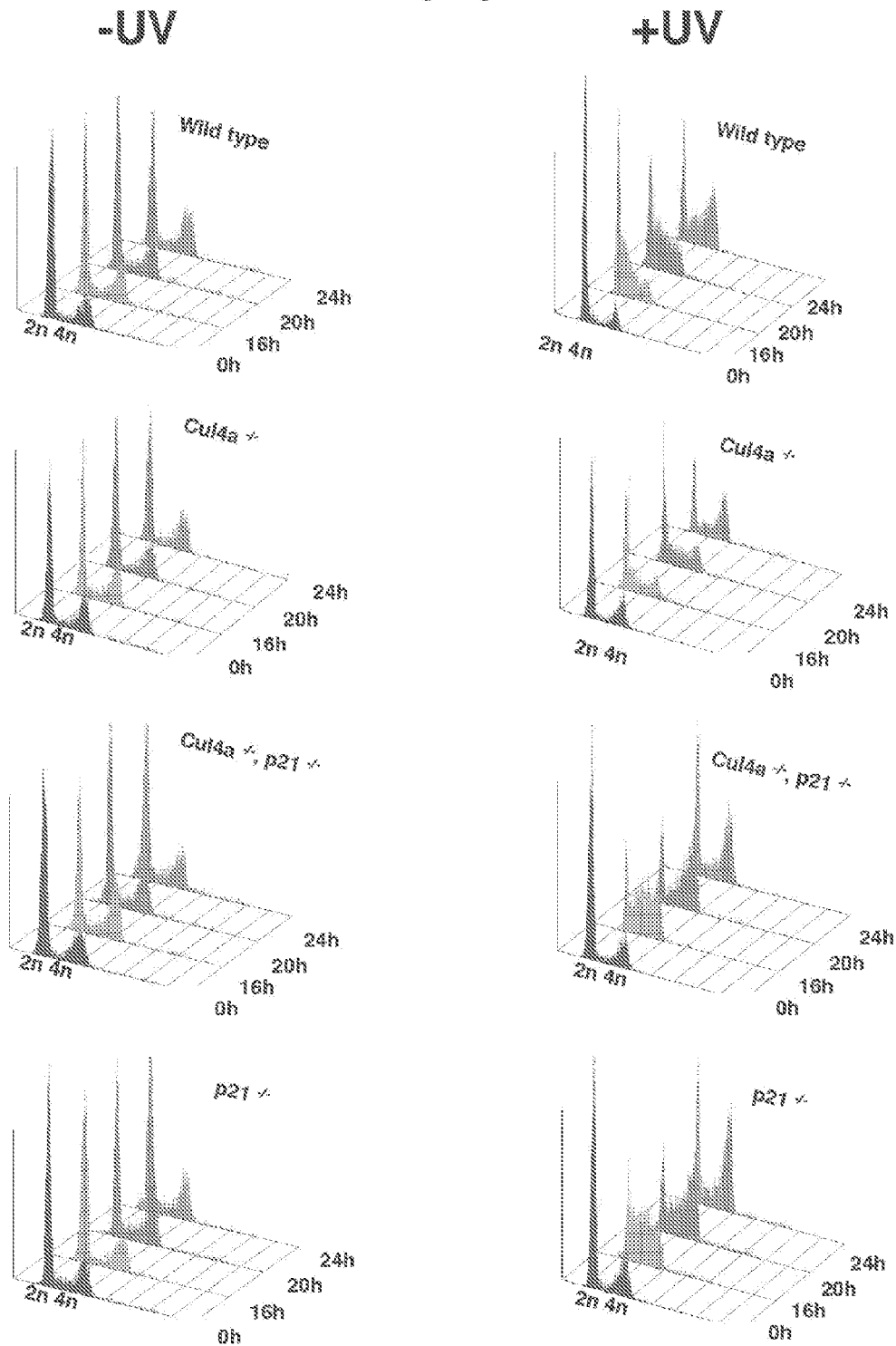
FIG. 8 is a set of histograms reflecting DNA content in MEFs of the indicated genotype irradiated or not with UV as determined by flow cytometry.

Cell cycle progression was assayed by synchronizing primary MEFs in G0/G1 by serum starvation for 72 hours, followed by UV-irradiation (10 J/m$^2$) at 3 h post-release into serum containing medium, and harvesting the MEFs at several indicated time points for analysis by [$^3$H]-thymidine incorporation assay (FIG. 7C) (Gitig and Koff, *Methods Mol. Biol.*, 142: 109-123 (2000)) or by flow cytometry (FIG. 8). For micronuclei measurement, MEFs were irradiated with UV at 10 J/m$^2$, cultured for 48 hours, fixed with 4% paraformaldehyde, and subjected to 4',6-diamidino-2-phenylindole (DAPI) staining.

Recognition of UV-damaged DNA is limited by the cellular pool of available DDB2 (Fitch et al., *DNA Repair (Amst)*, 2: 819-826 (2003); Tang and Chu, *DNA Repair (Amst)*, 1: 601-616 (2002)). Accumulation of DDB2 in Cul4a$^{-/-}$ MEFs led to increased UV-DDB activity compared to Cu/4a$^{f/f}$ MEFs (FIG. 7A; "B" indicates DDB-DNA complex), and an approximately 20% enhancement of GGR activity for both CPDs and 6-4 PPs, the most common lesions repaired by NER, as measured by ELISA-based GGR assay using anti-CPD and anti-6-4PP antibodies (FIG. 7B). In contrast, depletion of Cul4b by shRNA had no discernable effect on GGR efficiency (FIG. 7B). These results demonstrate that CUL4A abrogation permits effective elevation of GGR capacity beyond the threshold attainable in wild-type cells.

To determine whether the post-translational stabilization of p21 in Cul4a$^{-/-}$ MEFs demonstrated in Example 2 enforces the p21-dependent DNA damage checkpoint, the kinetics of S phase entry was measured in G0/G1-synchronized primary Cul4a$^{-/-}$ and wild-type MEFs post-UV by [$^3$H]-thymidine incorporation. Wild-type MEFs began to exit G1 and incorporate [$^3$H]-thymidine at 12 hours post-UV, and the majority entered S phase at 16-20 hours (FIG. 7C). However, Cul4a$^{-/-}$ MEFs were delayed by 4-6 hours in S phase entry post-UV. To validate that p21 is the primary downstream target responsible for delaying S phase entry in Cul4a$^{-/-}$ MEFs, Cul4a$^{-/-}$; p21$^{-/-}$ MEFs were generated by crossing Cul4a$^{-/-}$ and p21$^{-/-}$ mice. Indeed, the deletion of p21 effectively abrogated the prolonged G1 arrest associated with CUL4A loss, and resulted in accelerated S phase entry. 18% of Cul4a$^{-/-}$; p21$^{-/-}$ MEFs progressed into S phase at 8 hours post-UV, similar to what was seen in p21$^{-/-}$ MEFs (FIG. 7C). Flow cytometry analysis further confirmed that Cul4a$^{-/-}$ MEFs were delayed at least 6 hours in S phase progression compared to wild-type MEFs, while deletion of p21 effectively eliminated the G1 block in Cul4a$^{-/-}$ MEFs (FIG. 8). Therefore, stabilization of p21 in Cul4a$^{-/-}$ cells enforced the DNA damage-responsive G1 block to prevent premature S phase entry and to allot additional time for the NER machinery to identify and remove DNA photolesions.

Figure 7D:
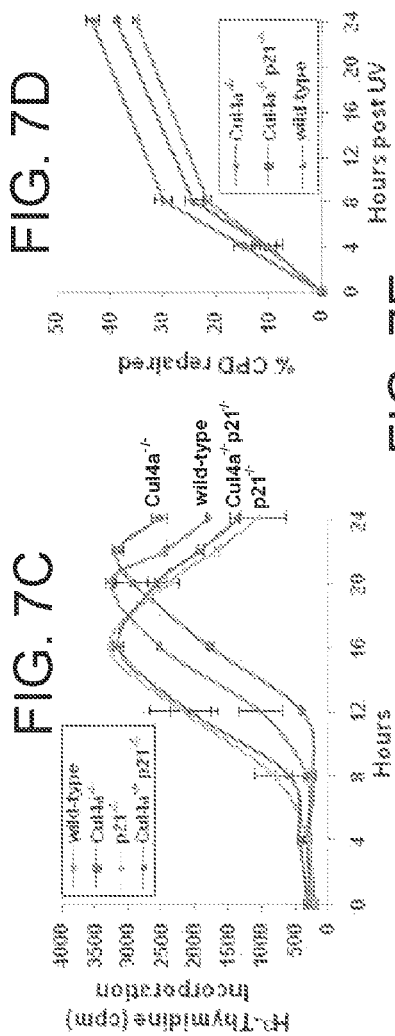
FIG. 7D is a line graph depicting repair of UV-induced CPDs in MEFs of the indicated genotypes.
Figure 7E:
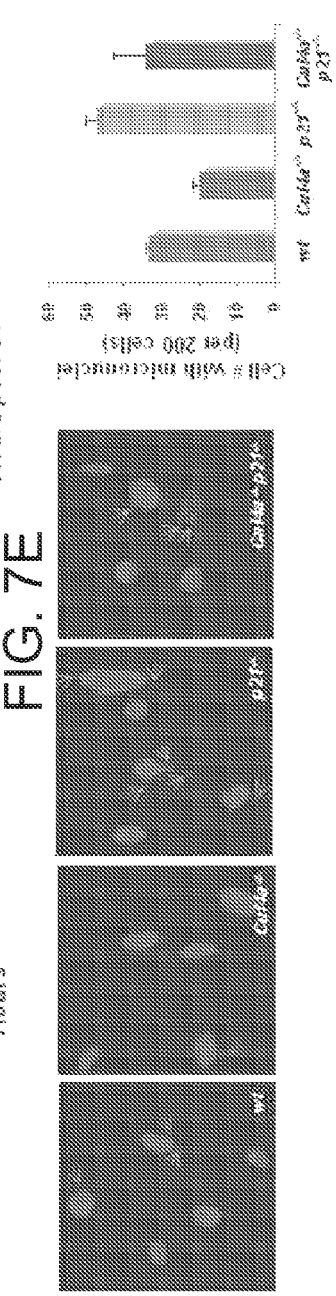
FIG. 7E includes images of micronuclei in MEFs of the indicated genotypes post-UV irradiation and a graph which quantifies the micronuclei.

Deletion of the p21 gene or knockdown of p21 by lentiviral shRNA in Cul4a$^{-/-}$ MEFs led to an 8-11% reduction of NER activity in CPD removal compared to Cul4a$^{-/-}$ MEFs, underscoring the benefit of p21 upregulation in the removal of UV-induced photolesions (FIG. 7D). It is noteworthy that, while the GGR enhancement by p21 was modest in the 24-hour repair assay following a single physiological UV dose (10 J/m$^2$), it would be effectively magnified with repeated UV assault, higher UV doses, or prolonged irradiation. The advantage of the prolonged G1 arrest in Cul4a$^{-/-}$ MEFs is further underscored by their enhanced ability to maintain genome integrity following UV exposure, as Cul4a$^{-/-}$ MEFs had 40% fewer micronuclei than wild-type MEFs induced by UV irradiation (FIG. 7E). Deletion of p21 abolished the Cul4a$^{-/-}$ MEFs' ability to prevent perturbation of chromosomal segregation during mitosis. Therefore, stabilization of p21 in Cul4a$^{-/-}$ cells is largely responsible for the enforced DNA damage-responsive G1 block and delayed cell cycle progression into S phase post-UV.

The results of this example demonstrated that Cul4a deficient cells have enhanced UV-damaged DNA binding (UV-DDB) and global genomic repair (GGR) activities relative to wild-type cells.

Example 4

This example demonstrates that skin-specific Cul4a knockout mice are resistant to UVB-induced skin carcinogenesis.

Cu/4a$^{f/f}$ mice were bred with K14-CreER$^{TAM}$ mice (Vasioukhin, et al., *Proc. Natl. Acad. Sci. U.S.A.*, 96: 8551-8556 (1999)) to generate inducible skin-specific Cul4a knockout mice. Eight- to twelve-week-old littermate mice were used, and their dorsal skins were shaved once a week for the UV irradiation experiment. Prior to UVB irradiation, dorsal skins of Cul4a$^{f/f}$; K14-CreER$^{TAM}$ mice were shaved and topically applied with tamoxifen/DMSO solution to induce the deletion of the Cul4a allele. As a control, wild-type littermates also received the tamoxifen/DMSO treatment (20 mg/day for 5 days). Individual mice were irradiated until either skin tumors appeared or for a maximum of 48 weeks, corresponding to the week at which all wild-type CUL4A mice developed skin tumors. In three independent experiments, a total of thirteen CUL4A knockout mice and nineteen wild-type littermates were irradiated at a beginning dose of 2,500 J/m$^2$ per day and gradually increased to a maximal dose of 3,500 J/m$^2$ per day by using a bank of four UVB lamps (TL20W/01 311NB Philips lamp, National Biological Co.). UVB flux was measured by a UVX digital radiometer (Model UVX-31). The mice were examined at least once a week for their health and tumor development. Mice were sacrificed if profoundly ill or if external tumors exceeded 1.5 cm in diameter. Statistical significance was measured using the log-rank test. For further analyses, skin tumors were fixed in 10% formalin at room temperature overnight, paraffin-embedded, and sectioned at 10 µm thickness. H&E staining was performed by conventional methods. For immunohistochemistry, skin tumor sections were deparaffinized with NEO-CLEAR™ Xylene Substitute (65351-85, EMD Chemicals, NJ) and anti-gen-retrieved with TRILOGY™ (CMX832, Cell Marque, Calif.) with boiling at 95° C. for 10 minutes. After blocking, sections were incubated with primary antibodies melan-A (A103) (sc-20032, Santa Cruz Biotechnology) and p63

(A4A) (sc-8431, Santa Cruz Biotechnology) at 4° C. overnight followed by secondary antibodies and 4',6-diamidino-2-phenylindole (DAPI) for counter staining.

Figure 9E:
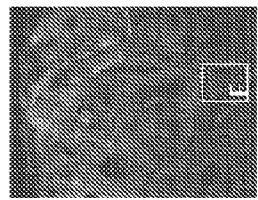
FIGS. 9E and 9F are images of SCC sections immunostained with the basal epidermal marker p63 and DAPI. The morphometry depicted in FIGS. 9C and 9D and the p63 immunostaining pattern depicted in FIGS. 9E and 9F indicate the tumor is a typical SCC.
Figure 9F:
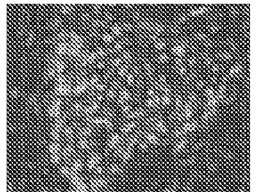
Figure 9A:
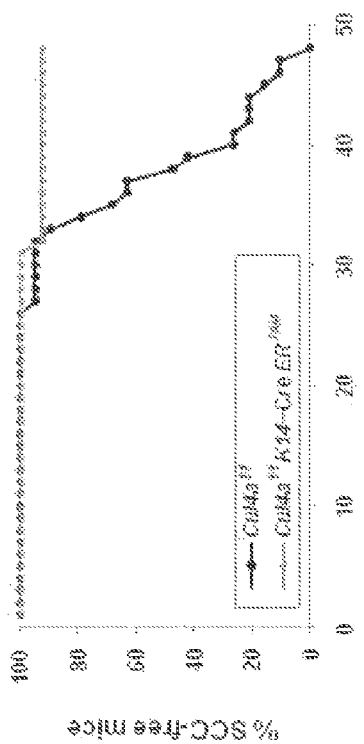
FIG. 9A is a Kaplan-Meier curve of the onset of squamous cell carcinomas (SCC) in control (Cu/4a$^{f/f}$) and skin-specific Cul4a knockout (Cul4a$^{f/f}$; K14-Cre ER$^{TAM}$) mice after chronic UV exposure.
Figure 9C:
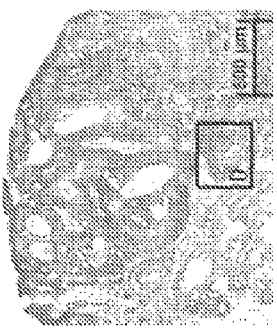
FIGS. 9C and 9D are images of hematoxylin and eosin-stained SCC sections.
Figure 9D:
Figure 9B:
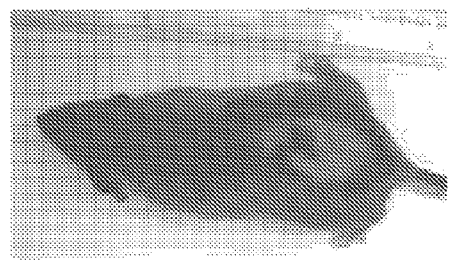
FIG. 9B is an image of a mouse bearing a SCC.

To evaluate the physiological impact of simultaneous upregulation of NER and the G1/S DNA damage checkpoint upon CUL4A abrogation, skin-specific tamoxifen-inducible Cul4a knockout mice were compared with Cu/4a$^{f/f}$ control animals in their susceptibility to UV-induced skin carcinogenesis. Cul4a was first deleted in a shaved area of dorsal skin of the Cul4a$^{f/f}$; K14-CreER$^{TAM}$ mice by topical administration of tamoxifen, and followed by daily UV-B irradiation. The Cu/4a$^{f/f}$ control mice started to develop skin tumors at week 27 of UV-B treatment. By week 48, all Cu/4a$^{f/f}$ mice developed tumors on the shaved dorsal skin area (FIG. 9A). Histological and immunohistochemical analysis confirmed that the tumors in control Cu/4a$^{f/f}$ mice were mostly squamous cell carcinomas (SCC) derived from epidermal origin (FIGS. 9B-F). Strikingly, all but one of the Cul4a$^{f/f}$; K14-CreER$^{TAM}$ mice remained SCC-free (FIG. 9A). Non-SCC tumors (e.g., spindle cell neoplasm) also developed, and, as expected, a similar incidence was observed in both Cu/4a$^{f/f}$ and Cul4a$^{f/f}$; K14-CreER$^{TAM}$ groups since K14-CreER$^{TAM}$ is not expressed in these cell types. The dramatic difference in the onset of SCCs versus non-SCC tumors suggests the specific association of tumor resistance with the loss of CUL4A. Of note, Cul4a$^{f/f}$ and Cul4a$^{f/f}$; K14-CreER$^{TAM}$ skin displayed similar apoptotic indices, thereby indicating that resistance to SCC is unlikely due to increased susceptibility to cell death in skin-specific Cul4a knockout animals.

Figure 10A:
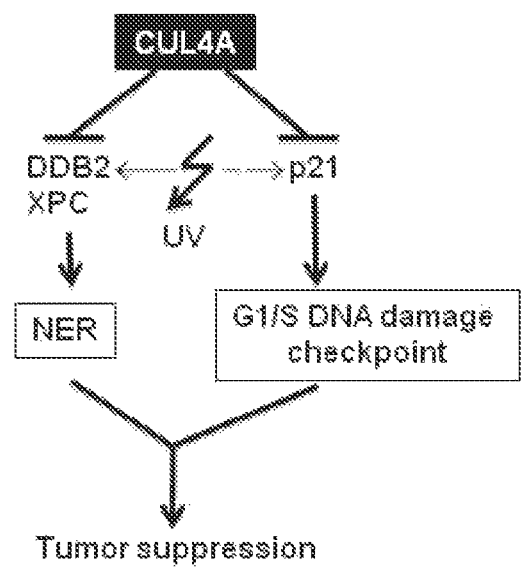
FIGS. 10A and 10B are diagrams which describe a possible role of CUL4A in establishing a threshold for DNA repair and tumor suppression. CUL4A coordinately suppresses the NER and the G1/S DNA damage checkpoint pathways through targeted degradation of DDB2 and p21, respectively. CUL4A deletion in cells elevates NER capacity and G1/S DNA damage checkpoint response beyond the threshold attainable in wild-type cells.
Figure 10B:
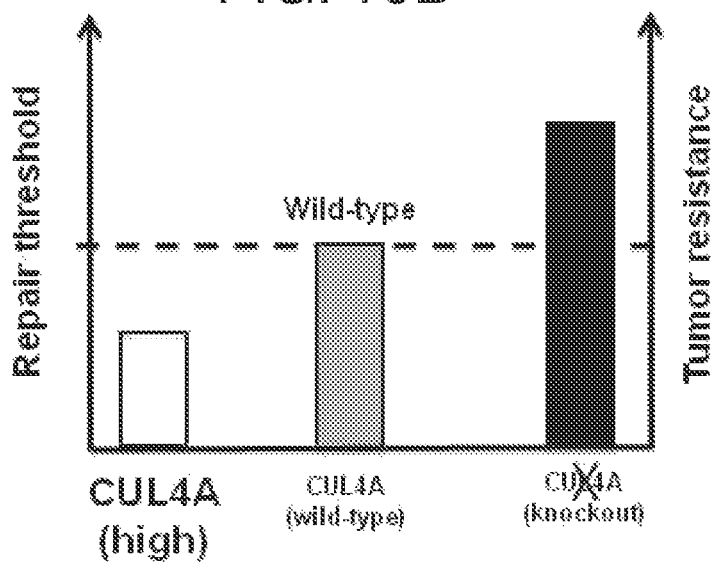

Without desiring to be bound by any particular theory, a hypothetical model depicting the role of CUL4A in the regulation of NER and tumorigenesis based upon the results described in Examples 1-4 is presented in FIG. 10. CUL4A coordinately suppresses the NER and the G1/S DNA damage checkpoint pathways through targeted degradation of DDB2 and p21, respectively. Thus, CUL4A deletion in cells elevates NER capacity and G1/S DNA damage checkpoint response beyond the threshold attainable in wild-type cells. The elevation of NER capacity and G1/S DNA damage checkpoint response contribute to the enhanced resistance to tumor development in Cul4a knockout mice relative to control mice.

The results of this example reflect that the abrogation of CUL4A confers enhanced protection against skin carcinogenesis in response to UV irradiation.

Example 5

This example demonstrates that a dominant negative (DN) CUL4 enhances NER in vitro.

HCT116 cells were infected with a control adenovirus or an adenovirus comprising a gene encoding a DN-CUL4 (SEQ ID NO: 18). Cells were then irradiated with 10 J/m$^2$ of UV-C. Genomic DNA was collected at 0 hr, 4 hr, 8 hr, and 24 hr and probed for CPD lesions as described in Example 3. The rate of NER activity was then calculated as the rate of CPD repair as a function of time.

Figure 11:
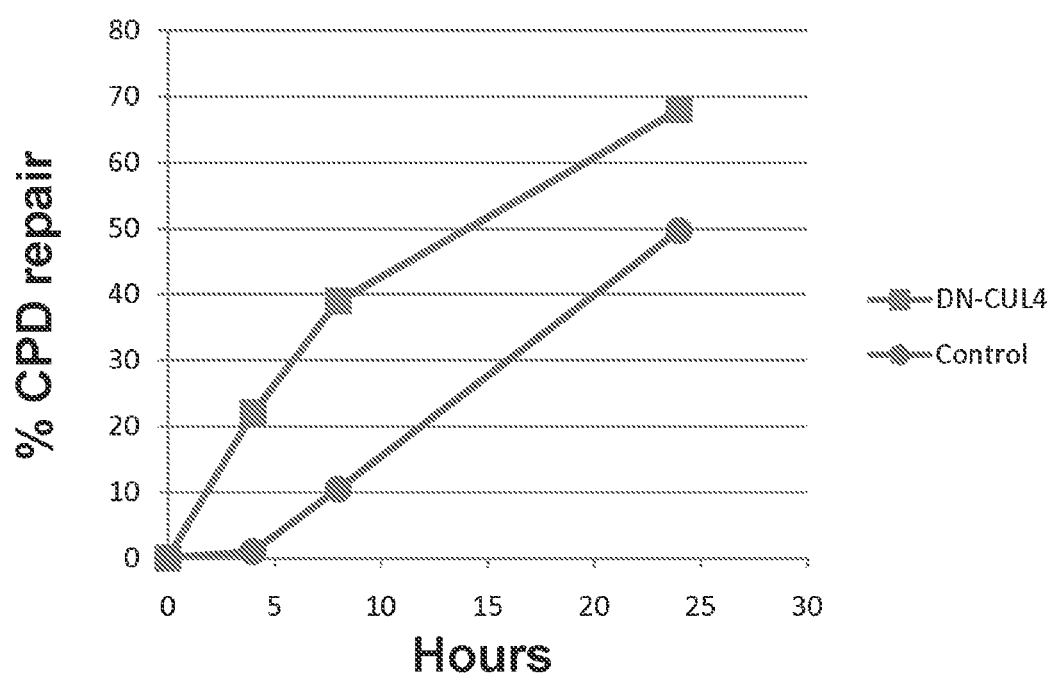
FIG. 11 is a line graph depicting repair of UV-induced CPDs in HCT116 cells infected with a control adenovirus or an adenovirus encoding a dominant negative (DN) CUL4 fragment.

CPD repair in UV-irradiated HCT116 cells occurred earlier and was more complete in cells expressing a DN-CUL4 as compared to control cells (FIG. 11).

The results of this example confirmed that a dominant negative (DN) CUL4 enhances NER in vitro.

Example 6

This prophetic example describes a high-throughput screening (HTS) assay for identifying a substance that modulates (e.g., inhibits) CUL4A binding to DDB1.

X-ray crystallographic studies have revealed the molecular details of the DDB1-CUL4A association (Angers et al., *Nature,* 443: 590-593 (2006); Li et al., *Cell,* 124: 105-117 (2006)). Eight residues within the DDB1-BPB β-propeller region (A400, 1402, L404, V443, E537, W561, I587, and R589) were identified to form direct contacts with CUL4A (FIG. 12). Both DDB1 and CUL4A contain multiple modular domains for protein-protein interactions that mediate assembly of other E3 components and additional regulators. To direct the selection of inhibitors at the CUL4A-DDB1 binding interface, a binding assay will be established with the minimum domains of each binding partner. Moreover, to enhance hit selection and optimize assay parameters, the initial screen will focus on the binding site between the top surface of DDB1 BPB (hereinafter, "DDB1(BPB)") (SEQ ID NO: 8) and the N-terminal α-helical region excluding the extreme N-terminal region of CUL4A (hereinafter, "CUL4A (NTD-N)") (SEQ ID NO: 7). It should be noted that the cullin machinery assembles E3 complex components in a highly precise and orderly manner such that the substrate will be oriented directly toward the E2 conjugating enzyme to accept ubiquitin. Although the extreme N-terminus of CUL4A forms a second binding site for DDB1(BPB), it is expected that disruption of binding between the top surface of DDB1(BPB) and the α-helical domain of CUL4A likely will misorient the recruited substrate, as evidenced by the W561A mutation of DDB1(BPB) which abrogates binding and effectively abolishes E3 activity despite the intact second binding site.

Figure 13:
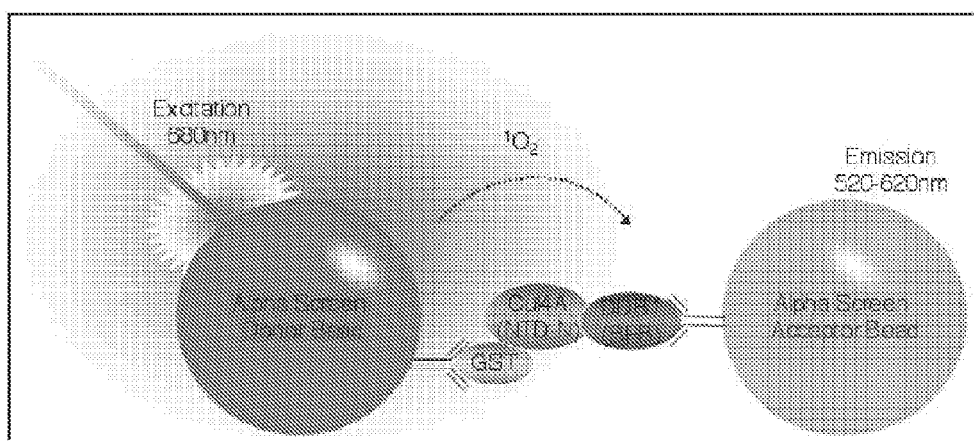
FIG. 13 is a schematic diagram of the screen (ALPHASCREEN™ Platform, adapted from PerkinElmer) to identify substances capable of modulating the interaction between CUL4A and DDB1.

The design of a bead-based non-radioactive Amplified Luminescent Proximity Homogeneous Assay is shown in FIG. 13, which can be adapted to provide a readout for the CUL4A(NTD-N)-DDB1(BPB) interaction. This assay typically involves donor and acceptor beads designed to associate with respective binding partners. Upon laser excitation, a photosensitizer in the "donor" bead converts ambient oxygen to a more excited singlet state. The singlet state oxygen molecules diffuse across to react with a thioxene derivative in the "acceptor" bead generating chemiluminescence at 370 nm. Because the light emitted is actually higher energy (lower wavelength), it further activities fluorophores contained in the same bead. The fluorophores subsequently emit light at 520-620 nm. This cascade of chemical reactions only occurs when donor and acceptor beads are brought in close proximity (~200 nm) initiated by the interaction between the binding partners. If the interaction between the two partners is weak or disrupted by inhibitors, singlet oxygen generated by a donor bead decays rapidly to the ground state because they are less likely to encounter an acceptor beads.

To apply the ALPHASCREEN™ system (PerkinElmer), donor beads coupled with anti-GST antibody are used to capture GST-CUL4A(NTD-N), and acceptor beads that bind the FLAG tag are used to immobilize FLAG-DDB1(BPB). The proximity of donor to acceptor beads will be induced upon binding of CUL4A(NTD-N) to DDB1(BPB), resulting in the generation of luminescent signal at 520 nm upon excitation at 680 nm, as recorded by an ENVISION™ Multilabel Plate Reader (PerkinElmer). The ALPHASCREEN™ binding assay between GST-CUL4A(NTD-N) and FLAG-DDB1 (BPB) is performed in 384-well microplates in triplicate, and compounds eliciting greater than 50% inhibition in signal strength are defined as "hits."

The parameters measured in the CUL4A(NTD-N)-DDB1 (BPB) binding assay include binding affinity, binding specificity, and vehicle (i.e., DMSO) sensitivity.

The binding affinity between CUL4A(NTD-N) and DDB1 (BPB) will be determined by mixing a constant amount of GST-CUL4A(NTD-N) (50 nM as a starting point) with increasing concentrations of FLAG-DDB1(BPB) complex (2-200 nM) and incubating at room temperature for 2 hours. The final reaction volume will be 25 µL, containing 5 µL of each protein and 5 µL ALPHASCREEN™ buffer. After mixing, the plate will be incubated at room temperature, shaking for 1 hour followed by addition of 5 µL each of ALPHASCREEN™ GST-binding donor and FLAG-binding acceptor beads (20 ng/mL). The mixture will equilibrated at room temperature for 1 hour prior to reading. Each data point will be performed in triplicate. The binding data will be analyzed by GraphPad Prism software, and an apparent $K_d$ will be determined.

To demonstrate the specificity of CUL4A(NTD-N)-DDB1 (BPB) binding, competition assays will be performed with untagged CUL4A(NTD-N) and DDB1(BPB). When increasing concentrations of untagged CUL4A(NTD-N) or DDB1 (BPB) suppress binding between GST-CUL4A(NTD-N) and FLAG-DDB1(BPB), the $IC_{50}$ can be determined. The negative control is the FLAG-DDB1(BPB-W561A) mutant, which is incapable of binding CUL4A (Li et al., Cell, 124: 105-17 (2006)).

An effective HTS assay requires that protein targets retain full biological activity in significant concentrations of DMSO, the solvent used to dissolve small molecule libraries. To test the DMSO sensitivity of GST-CUL4A(NTD-N) and FLAG-DDB1(BPB) in the ALPHASCREEN™ format, increasing concentrations (0-20%) of DMSO will be added to the binding mixture to determine the highest concentration that still retains efficient interaction.

This binding assay between affinity-purified recombinant CUL4A(NTD-N) and DDB1(BPB) for the ALPHASCREEN™ format emphasizes the major protein-protein interface for interrogation. This approach may reduce the possibility of finding compounds that affect allosteric binding sites elsewhere on full-length CUL4A or DDB1 that may alter the tertiary structure, resulting in effective disengagement of DDB1-CUL4A association. Therefore, an alternative approach employs full-length CUL4A (e.g., SEQ ID NO: 1) and DDB1 (e.g., SEQ ID NO: 3) as binding partners in the ALPHASCREEN™ assay format using full-length DDB1 with an N-terminal FLAG-tag and full-length CUL4A (made by co-expressing CUL4A with Rbx1 using a bicistronic pCool vector derived from pGEX-4T-1 to improve the expression and folding/solubility of CUL4A (Li et al., Cell, 124: 105-17 (2006)). In yet another approach, a fragment of CUL4A (e.g., SEQ ID NO: 5 or SEQ ID NO: 6) and DDB1 or DDB1(BPB) are used as binding partners in the ALPHASCREEN™ assay. This assay can identify additional hits that alter the precise assembly of DDB1-CUL4A required for E3 ligase activity.

Example 7

This prophetic example describes quantitative HTS assays to identify small molecules that disrupt DDB1-CUL4A interaction and ubiquitin ligase activity.

Because a single point mutation in DDB1(BPB-W561A) is sufficient to disrupt DDB1-CUL4A binding (Li et al., Cell, 124: 105-17 (2006)), it is possible that small molecules targeting the key point of the DDB1-CUL4A interface or on a secondary site that induces allosteric changes in conformation can effectively collapse the DDB1-CUL4A interaction module and abrogate ubiquitin ligase function.

A large-scale high-throughput screen of library compounds will be performed to identify compounds that disrupt the DDB1(BPB)-CUL4A(NTD-N) interaction using the assay described in Example 6. Each component of the binding reaction is titrated such that the final concentration of each is near the top of the linear response range. The optimal order of addition of binding partners can be determined as follows. First, GST-CUL4A(NTD-N) is incubated with the compounds, and FLAG-DDB1(BPB) is subsequently added prior to recording the result. The screen is performed on a Biomek FX liquid handling workstation equipped with quadrant pipetting and plate stacker units (Beckman). The DDB1 (BPB)-CUL4A(NTD-N) ALPHASCREEN™ assay is performed in a 384-well microplate format with 352 unique compounds in each plate. Column 1 and column 24 contain positive (GST-CUL4A(NTD-N) and FLAG-DDB1(BPB)) and negative (GST-CUL4A(NTD-N) and FLAG-DDB1 (BPB-W561A)) controls. The compounds are diluted in the optimal DMSO concentration determined as described in Example 6 above to maximize the signal, and dispensed into the plate wells in 1 µL aliquots. This gives a final compound concentration of 10 mM in the 10 µL binding reaction, which is added at the same time as the GST-CUL4A(NTD-N) and FLAG-DDB1(BPB) at the optimal concentration and order-of-addition for this binding assay. Donor and acceptor beads are added and incubated for 1 hour, and the ALPHASCREEN™ signal is read on an ENVISION™ multiplate reader (PerkinElmer). Each plate must have a Z' score of 0.5 or greater with both positive and negative control wells (Zhang et al., J. Biomol. Screen, 4: 67-73 (1999)). The Z'-factor (for assay quality) is be calculated automatically during data analysis using the ActivityBase software package (IDBS software, Emeryville, Calif.) for each plate. Compounds causing a 50% reduction in luminescent signal in two independent trials are classified as hits and subject to subsequent validation in secondary screens.

Multiple secondary screens and specificity assays to eliminate false positives and nonspecific inhibitors will be performed. Compounds determined to be "non-specific" as documented by the Sloan Kettering HTS core database that were previously shown to hit multiple targets in multiple assays are eliminated. Measuring $IC_{50}$ of the hits using a series of 2-fold compound dilutions in HTS format with the hit compounds enables pursuit of only those compounds that exhibit dose-dependent inhibition. Hits are organized into groups of structurally related compounds to identify common scaffolds and to examine the structure-activity relationship (SAR) of these hits and "non-hits" (i.e., no inhibition) with related structures from the chemical library database. The SAR analysis serves as a filter for hit confirmation, and defines the core structural features of these inhibitors. The reversibility of inhibition is determined by dialysis of the mixture of the protein complex with the test compound. This removes the inhibitor and restores the signal to control levels if inhibition is reversible. The authenticity of inhibition of the hit compounds is further tested by a conventional DDB1 in vitro ubiquitination assay. Additionally, pull-down assays in the presence and absence of the hit compounds will be performed as an independent assay to verify perturbation of the DDB1(BPB)-CUL4A(NTD-N) interaction. The hit compound(s) fulfilling all the criteria laid out will be further pursued. Any compounds that irreversibly inhibit DDB1 (BPB)-CUL4A(NTD-N) association, that are specific can be pursued further, since the two longest used antibacterial and anti-cancer drugs are in this class (penicillin and 5-FU).

Compounds from the secondary screen with potent $IC_{50}$ values will be chosen to test whether they perturb DDB1-CUL4A ubiquitin ligase activity and NER activities in vivo. Prior to testing in vivo activities of hit compounds, cell permeability of candidates will be determined using parallel artificial membrane permeability assay (PAMPA), which uses a lipid-filled membrane to determine the passive, transcellular permeability properties of potential drug compounds (Kansy et al., *J. Med. Chem.,* 41: 1007-10 (1998)). The PAMPA assay (Millipore) is relatively simple, inexpensive, and straightforward, yet produces comparable results to traditional cell-based assays like those using Caco-2 cells (Kansy et al., *J. Med. Chem.,* 41: 1007-10 (1998)). Compounds with good cell permeability will be subsequently tested in cell lines. Potent leads that display poor membrane permeability can be modified to be more lipophilic to improve membrane permeability, while taking care to avoid compromising solubility.

The primary Cul4A$^{fl/fl}$ and DDB1$^{fl/fl}$ MEF cells (Cang et al., *Cell,* 127: 929-40 (2006)) and human HCT116 colon cancer cells are established model cell lines to test the effects of inhibitors on DDB2 degradation and to measure the effects on NER activity. Cells will be treated with test compounds or vehicle for 4 hours, and then harvested and lysed for immunoblotting using antibodies against DDB2, DDB1, CUL4A, and 13-actin (control). Compounds that selectively cause an increase in DDB2 expression are further evaluated for their ability to repair UV-induced CPDs and 6,4-PPs using the ELISA based assay described in Example 3 above. As a control for compound specificity, the primary Cul4A$^{fl/fl}$ and DDB1$^{fl/fl}$ MEF cells will be infected with recombinant adenovirus expressing Cre recombinase to delete endogenous Cul4a or DDB1 prior to addition of the hit compounds to determine if the inhibitory effects are indeed dependent on DDB1-CUL4A ubiquitin ligase. A recombinant lentivirus carrying shRNAs for human CUL4A or DDB1 can also be used to assess the specificity of compounds in human HCT116 cells.

Lead small molecule inhibitors identified according to the methods described in this Example can be co-crystallized with CUL4A or DDB1 in order to determine the molecular basis of inhibition and tested in the UV-skin cancer mouse model system described above to evaluate their efficacy in protecting against skin carcinogenesis, and to further develop these synthetic inhibitors as anti-cancer agents for prevention and treatment of human malignancies.

Example 8

This prophetic example demonstrates another embodiment of the inventive method of identifying a substance that modulates (e.g., inhibits) CUL4A ubiquitin ligase activity that is suitable for the identification of peptide inhibitors.

Figure 14:
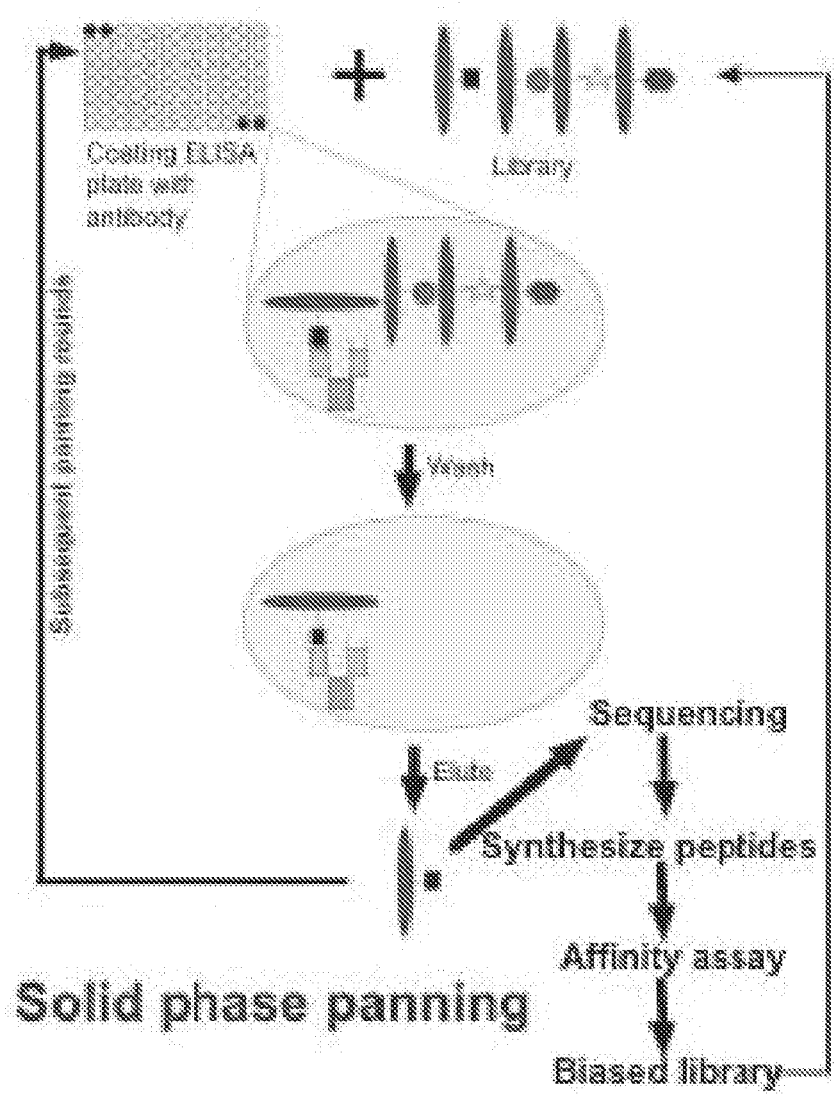
FIG. 14 is a schematic diagram of the phage display library screen to identify peptide modulators of the interaction between CUL4A and DDB1.

Peptide-based inhibitors that interact with either DDB1 (BPB) or CUL4A(NTD-N) can be identified by screening phage display libraries using the protocol described in FIG. 14. To summarize briefly, FLAG-DDB1(BPB) or GST-CUL4A(NTD-N) is immobilized onto FLAG or GST antibody-coated 96-well ELISA plates, and incubated with 10 μL of phage library in each well. Following extensive wash, the bound phage are eluted by either trypsinization or low pH glycine elution buffer, and infected in *E. coli* for amplification, sequencing, and second and third round panning which enrich for high-affinity peptides. Selected peptides are synthesized using a peptide synthesizer (Protein Technologies, Inc.), purified by HPLC and evaluated in the CUL4A(NTD-N)-DDB1(BPB) ALPHASCREEN™ assay as described in Example 6 and Example 7 for their efficacy in blocking the binding interface, and inhibiting in vitro DDB1 ubiquitination. Peptides that demonstrate at least 50% inhibition of binding or E3 ligase activity are evaluated in vivo in Cul4A$^{fl/fl}$ and DDB1$^{fl/fl}$ MEF cells or human HCT116 cells for inhibition of DDB2 ubiquitination and degradation, and for enhancing NER activity against UV-induced CPDs or 6,4-PPs on DNA. To improve membrane permeability the synthetic peptides can be linked with the HIV-TAT membrane transduction signal sequence (Nagahara et al., *Nat. Med.,* 4: 1449-52 (1998)). The stability of the identified peptide inhibitors against cellular peptidases can be improved by applying the retro-inverso peptide technology to synthesize the optimized peptides using D-amino acids assembled in the reverse order as that of the parent peptide. Such retro-inverso peptides present their side chains in orientations similar to the original structure, yet are resistant to peptidase cleavage in vivo (Angers et al., *Nature,* 443: 590-3 (2006); Van Regenmortel and Muller, *Curr. Opin. Biotechnol.,* 9: 377-82 (1998)).

Exemplary phage display peptide libraries include, without limitation, $CX_{10}C/p8+8$ libraries, $NNS_{20}/p8+8$ libraries, and libraries on a knottin scaffold, which are described in Table 1.

TABLE 1

| Name | $CX_{10}C$-1 | $CX_{10}C$-2 | $NNS_{20}$-1 | $NNS_{20}$-2 | Knottin-1 | Knottin-2 |
|---|---|---|---|---|---|---|
| Vector | pC89s | pC89s | pC89s | pC89s | pC89s | pC89s |
| Type | p8 + 8 | p8 + 8 | p8 + 8 | p8 + 8 | p8 + 8 | p8 + 8 |
| Display form | Cyclic | Cyclic | Linear | Linear | Structured | Structured |
| Copies/virion | ~200 | ~200 | ~200 | ~200 | ~200 | ~200 |
| Diversity | $5.4 \times 10^8$ | $1.9 \times 10^9$ | $8.8 \times 10^8$ | $7.04 \times 10^8$ | $1 \times 10^8$ | $0.5 \times 10^9$ |
| Titer (cfu/ml) | $1.35 \times 10^{13}$ | $4.05 \times 10^{13}$ | $1 \times 10^{14}$ | $1 \times 10^{14}$ | $3.4 \times 10^{12}$ | $1 \times 10^{12}$ |

The two $CX_{10}C/p8+8$ phage display peptide libraries contain $2.44 \times 10^9$ cysteine constrained, 10-amino acid long sequences. The two $NNS_{20}/p8+8$ libraries contain $1.58 \times 10^9$ linear 20-amino acid long sequences. In addition to peptides existing in cyclic or in linear form, it is also desirable to have peptides displayed on a defined protein scaffold. Accordingly, phage display libraries on a knottin scaffold can also be screened. Knottins are functionally-diverse, but structurally related proteins, typically less than 40 residues in length. All knottins share a common scaffold comprising a small triple stranded antiparallel β-sheet and disulphide bond framework.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of preventing or treating a condition associated with DNA damage in an animal, which method comprises administering to an animal in need thereof an effective amount of a substance that interferes with the activity of CUL4A, thereby preventing or treating a condition associated with DNA damage in the animal.

2. The method of claim 1, wherein the substance that interferes with the activity of CUL4A causes an increase in DNA repair activity.

3. The method of claim 2, wherein the increase in DNA repair activity is an increase nucleotide excision repair activity.

4. The method of claim 1, wherein the condition associated with DNA damage is selected from the group consisting of aging, prolonged exposure to ultraviolet radiation, exposure to a chemical carcinogen, cancer, Xeroderma pigmentosum, Cockayne syndrome, and Ataxia-telangiectasia.

5. The method of claim 4, wherein the condition associated with DNA damage is cancer, and the cancer is selected from the group consisting of skin cancer, lung cancer, throat cancer, and liver cancer.

6. The method of claim 1, wherein the substance that interferes with the activity of CUL4A is selected from the group consisting of polypeptides, peptidomimetics and polynucleotides.

7. The method of claim 6, wherein the substance that interferes with the activity of CUL4A is a polynucleotide, and the polynucleotide is selected from the group consisting of small interfering RNA (siRNA), short hairpin RNA (shRNA), antisense oligonucleotides, aptamers, and ribozymes.

8. The method of claim 1, wherein the substance that interferes with the activity of CUL4A inhibits the expression of CUL4A.

9. The method of claim 1, wherein the substance that interferes with the activity of CUL4A disrupts the binding of CUL4A to damaged DNA binding protein 1 (DDB1).

10. The method of claim 9, wherein the substance that interferes with the activity of CUL4A competitively inhibits the binding of an endogenous CUL4A to DDB1.

11. The method of claim 9, wherein the substance that interferes with the activity of CUL4A is a polypeptide or peptidomimetic.

12. The method of claim 11, wherein the polypeptide or peptidomimetic comprises a fragment of CUL4A.

13. The method of claim 1, wherein the substance that interferes with the activity of CUL4A is administered topically, orally, intranasally, parenterally, enterically, rectally, or ocularly.

14. The method of claim 1, wherein the substance that interferes with the activity of CUL4A is administered in a composition comprising the inhibitor of CUL4A and a carrier.

15. The method of claim 14, wherein the composition is a sunscreen composition.

16. The method of claim 15, wherein the sunscreen composition comprises:
(a) the substance that interferes with the activity of CUL4A,
(b) a photoprotective amount of a sunscreen compound selected from the group consisting of sulisobenzone, dioxybenzone, methyl anthranilate, 4-aminobenzoic acid (PABA), amyl dimethyl PABA, octyl dimethyl PABA, glyceryl PABA, 2-ethoxyethyl p-methoxycinnamate, diethamolamine p-methoxycinnamate, ethylhexyl p-methoxycinnamate, digalloyl trioleate, ethyl 4-bis(hydroxypropyl)aminobenzoate, 2-ethylhexyl-2-cyano-3,3-diphenylacrylate, 2-ethylhexyl salicylate, homomethyl salicylate, triethanolamine salicylate, 2-phenylbenzimidazole-5-sulfonic acid, red petrolatum, titanium dioxide, zinc oxide, and combinations thereof, and
(c) a cosmetically acceptable carrier.

17. The method of claim 1, further comprising administering a chemotherapeutic agent to the animal.

18. The method of claim 1, wherein the animal is a human.

19. A composition comprising a substance that interferes with the activity of CUL4A in an animal and a cosmetically acceptable carrier which further comprises a photoprotective amount of a sunscreen compound selected from the group consisting of sulisobenzone, dioxybenzone, methyl anthranilate, 4-aminobenzoic acid(PABA), amyl dimethyl PABA, octyl dimethyl PABA, glyceryl PABA, 2-ethoxyethyl p-methoxycinnamate, diethamolamine p-methoxycinnamate, ethylhexyl p-methoxycinnamate, digalloyl trioleate, ethyl 4-bis(hydroxypropyl)aminobenzoate, 2-ethylhexyl-2-cyano-3,3-diphenylacrylate, 2-ethylhexyl salicylate, homomethyl salicylate, triethanolamine salicylate, 2-phenylbenzimidazole-5-sulfonic acid, red petrolatum, titanium dioxide, zinc oxide, and combinations thereof.

20. The composition of claim 19, wherein the substance is selected from the group consisting of polypeptides, peptidomimetics and polynucleotides.

21. The composition of claim 19, wherein the substance is a polynucleotide, and the polynucleotide is selected from the group consisting of small interfering RNA (siRNA), short hairpin RNA (shRNA), antisense oligonucleotides, aptamers, and ribozymes.

22. The composition of claim 19, wherein the substance that interferes with the activity of CUL4A competitively inhibits the binding of an endogenous CUL4A to damaged DNA binding protein (DDB 1) in an animal.

23. The composition of claim 19, wherein the substance that interferes with the activity of CUL4A is a polypeptide or peptidomimetic which comprises a fragment of CUL4A.

* * * * *

```
                        SEQUENCE LISTING

<160> NUMBER OF SEQ ID NOS: 18

<210> SEQ ID NO 1
<211> LENGTH: 759
<212> TYPE: PRT
<213> ORGANISM: Homo sapiens
<220> FEATURE:
<223> OTHER INFORMATION: CUL4A

<400> SEQUENCE: 1

Met Ala Asp Glu Ala Pro Arg Lys Gly Ser Phe Ser Ala Leu Val Gly
1               5                   10                  15

Arg Thr Asn Gly Leu Thr Lys Pro Ala Ala Leu Ala Ala Ala Pro Ala
            20                  25                  30

Lys Pro Gly Gly Ala Gly Gly Ser Lys Lys Leu Val Ile Lys Asn Phe
        35                  40                  45

Arg Asp Arg Pro Arg Leu Pro Asp Asn Tyr Thr Gln Asp Thr Trp Arg
    50                  55                  60

Lys Leu His Glu Ala Val Arg Ala Val Gln Ser Ser Thr Ser Ile Arg
65                  70                  75                  80

Tyr Asn Leu Glu Glu Leu Tyr Gln Ala Val Glu Asn Leu Cys Ser His
                85                  90                  95

Lys Val Ser Pro Met Leu Tyr Lys Gln Leu Arg Gln Ala Cys Glu Asp
            100                 105                 110

His Val Gln Ala Gln Ile Leu Pro Phe Arg Glu Asp Ser Leu Asp Ser
        115                 120                 125

Val Leu Phe Leu Lys Lys Ile Asn Thr Cys Trp Gln Asp His Cys Arg
130                 135                 140

Gln Met Ile Met Ile Arg Ser Ile Phe Leu Phe Leu Asp Arg Thr Tyr
145                 150                 155                 160

Val Leu Gln Asn Ser Thr Leu Pro Ser Ile Trp Asp Met Gly Leu Glu
                165                 170                 175

Leu Phe Arg Thr His Ile Ile Ser Asp Lys Met Val Gln Ser Lys Thr
            180                 185                 190

Ile Asp Gly Ile Leu Leu Leu Ile Glu Arg Glu Arg Ser Gly Glu Ala
        195                 200                 205

Val Asp Arg Ser Leu Leu Arg Ser Leu Leu Gly Met Leu Ser Asp Leu
    210                 215                 220

Gln Val Tyr Lys Asp Ser Phe Glu Leu Lys Phe Leu Glu Glu Thr Asn
225                 230                 235                 240

Cys Leu Tyr Ala Ala Glu Gly Gln Arg Leu Met Gln Glu Arg Glu Val
                245                 250                 255

Pro Glu Tyr Leu Asn His Val Ser Lys Arg Leu Glu Glu Glu Gly Asp
```

-continued

```
                    260                 265                 270
Arg Val Ile Thr Tyr Leu Asp His Ser Thr Gln Lys Pro Leu Ile Ala
                275                 280                 285
Cys Val Glu Lys Gln Leu Leu Gly Glu His Leu Thr Ala Ile Leu Gln
                290                 295                 300
Lys Gly Leu Asp His Leu Leu Asp Glu Asn Arg Val Pro Asp Leu Ala
305                 310                 315                 320
Gln Met Tyr Gln Leu Phe Ser Arg Val Arg Gly Gln Gln Ala Leu
                325                 330                 335
Leu Gln His Trp Ser Glu Tyr Ile Lys Thr Phe Gly Thr Ala Ile Val
                340                 345                 350
Ile Asn Pro Glu Lys Asp Lys Asp Met Val Gln Asp Leu Leu Asp Phe
                355                 360                 365
Lys Asp Lys Val Asp His Val Ile Glu Val Cys Phe Gln Lys Asn Glu
                370                 375                 380
Arg Phe Val Asn Leu Met Lys Glu Ser Phe Glu Thr Phe Ile Asn Lys
385                 390                 395                 400
Arg Pro Asn Lys Pro Ala Glu Leu Ile Ala Lys His Val Asp Ser Lys
                405                 410                 415
Leu Arg Ala Gly Asn Lys Glu Ala Thr Asp Glu Glu Leu Glu Arg Thr
                420                 425                 430
Leu Asp Lys Ile Met Ile Leu Phe Arg Phe Ile His Gly Lys Asp Val
                435                 440                 445
Phe Glu Ala Phe Tyr Lys Lys Asp Leu Ala Lys Arg Leu Leu Val Gly
                450                 455                 460
Lys Ser Ala Ser Val Asp Ala Glu Lys Ser Met Leu Ser Lys Leu Lys
465                 470                 475                 480
His Glu Cys Gly Ala Ala Phe Thr Ser Lys Leu Glu Gly Met Phe Lys
                485                 490                 495
Asp Met Glu Leu Ser Lys Asp Ile Met Val His Phe Lys Gln His Met
                500                 505                 510
Gln Asn Gln Ser Asp Ser Gly Pro Ile Asp Leu Thr Val Asn Ile Leu
                515                 520                 525
Thr Met Gly Tyr Trp Pro Thr Tyr Thr Pro Met Glu Val His Leu Thr
                530                 535                 540
Pro Glu Met Ile Lys Leu Gln Glu Val Phe Lys Ala Phe Tyr Leu Gly
545                 550                 555                 560
Lys His Ser Gly Arg Lys Leu Gln Trp Gln Thr Thr Leu Gly His Ala
                565                 570                 575
Val Leu Lys Ala Glu Phe Lys Glu Gly Lys Lys Glu Phe Gln Val Ser
                580                 585                 590
Leu Phe Gln Thr Leu Val Leu Met Phe Asn Glu Gly Asp Gly Phe
                595                 600                 605
Ser Phe Glu Glu Ile Lys Met Ala Thr Gly Ile Glu Asp Ser Glu Leu
                610                 615                 620
Arg Arg Thr Leu Gln Ser Leu Ala Cys Gly Lys Ala Arg Val Leu Ile
625                 630                 635                 640
Lys Ser Pro Lys Gly Lys Glu Val Glu Asp Gly Asp Lys Phe Ile Phe
                645                 650                 655
Asn Gly Glu Phe Lys His Lys Leu Phe Arg Ile Lys Ile Asn Gln Ile
                660                 665                 670
Gln Met Lys Glu Thr Val Glu Glu Gln Val Ser Thr Thr Glu Arg Val
                675                 680                 685
```

-continued

```
Phe Gln Asp Arg Gln Tyr Gln Ile Asp Ala Ala Ile Val Arg Ile Met
        690                 695                 700
Lys Met Arg Lys Thr Leu Gly His Asn Leu Leu Val Ser Glu Leu Tyr
705                 710                 715                 720
Asn Gln Leu Lys Phe Pro Val Lys Pro Gly Asp Leu Lys Lys Arg Ile
                725                 730                 735
Glu Ser Leu Ile Asp Arg Asp Tyr Met Glu Arg Asp Lys Asp Asn Pro
            740                 745                 750
Asn Gln Tyr His Tyr Val Ala
        755
```

<210> SEQ ID NO 2
<211> LENGTH: 3797
<212> TYPE: DNA
<213> ORGANISM: Homo sapiens
<220> FEATURE:
<223> OTHER INFORMATION: Cul4a

<400> SEQUENCE: 2

| | | | | | |
|---|---|---|---|---|---|
| ccggcccagc | catggcggac | gaggccccgc | ggaagggcag | cttctcggcg | ctcgtgggcc | 60 |
| gcaccaacgg | cctcaccaag | cccgcggccc | tggccgccgc | gcccgccaag | ccgggggggcg | 120 |
| cgggcggctc | caagaagctg | gtcatcaaga | acttccgaga | cagacctcgg | ctgcccgaca | 180 |
| actacacgca | ggacacgtgg | cggaagctgc | acgaggcggt | gcgggccgtg | cagagcagca | 240 |
| cctccatcag | gtacaacctc | gaggagctct | accaggctgt | ggaaaatctc | tgttctcaca | 300 |
| aagtctcccc | aatgctctac | aagcaactgc | gtcaggcctg | tgaagaccac | gtccaggcac | 360 |
| agatccttcc | gtttagagaa | gactcactag | atagtgtttt | atttttaaag | aagattaaca | 420 |
| cgtgctggca | ggaccactgc | agacaaatga | tcatgatcag | aagcatcttc | ctgttcttgg | 480 |
| accgcaccta | tgtgctgcag | aactccacgc | tgccctccat | ctgggatatg | ggattagaac | 540 |
| tgtttagaac | ccatattatt | agtgataaaa | tggttcagag | taaaaccatt | gatggaatcc | 600 |
| tactgctgat | cgagcgcgag | aggagcggcg | aggccgtgga | ccggagcctg | ttgcggagcc | 660 |
| tcctgggcat | gctgtctgac | ctgcaggtgt | ataaagattc | atttgaactg | aaattttgg | 720 |
| aagagactaa | ttgcttatat | gctgccgaag | gccaaaggtt | aatgcaggaa | agagaggttc | 780 |
| cagaatatct | taaccatgta | agtaaacgct | tagaggaaga | gggagacaga | gtaatcactt | 840 |
| acttggacca | cagcacacag | aaaccactga | ttgcttgtgt | ggagaaacag | ctattaggag | 900 |
| aacatttaac | agcaattctg | cagaaagggc | tcgaccactt | actggatgag | acagagtgc | 960 |
| cggacctcgc | acagatgtac | cagctgttca | gccgggtgag | gggcgggcag | caggcgctgc | 1020 |
| tgcagcactg | gagcgagtac | atcaagactt | ttggaacagc | gatcgtaatc | aatcctgaga | 1080 |
| aagacaaaga | catggtccaa | gacctgttgg | acttcaagga | caaggtggac | cacgtgatcg | 1140 |
| aggtctgctt | ccagaagaat | gagcggttcg | tcaacctgat | gaaggagtcc | tttgagacgt | 1200 |
| tcatcaacaa | gagacccaac | aagcctgcag | aactgatcgc | aaagcatgtg | gattcaaagt | 1260 |
| taagagcagg | caacaaagaa | gccacagacg | aggagctgga | gcggacgttg | acaagatca | 1320 |
| tgatcctgtt | caggtttatc | cacggtaaag | atgtctttga | agcattttat | aaaaaagatt | 1380 |
| tggcaaaaag | actccttgtt | gggaaaagtg | cctcagtcga | tgctgaaaag | tctatgttgt | 1440 |
| caaagctcaa | gcatgagtgc | ggtgcagcct | tcaccagcaa | gctggaaggc | atgttcaagg | 1500 |
| acatggagct | ttcgaaggac | atcatggttc | atttcaagca | gcatatgcag | aatcagagtg | 1560 |
| actcaggccc | tatagcctc | acagtgaaca | tactcacaat | gggctactgg | ccaacataca | 1620 |
| cgcccatgga | agtgcactta | accccagaaa | tgattaaact | tcaggaagta | tttaaggcat | 1680 |

```
tttatcttgg aaagcacagt ggtcgaaaac ttcagtggca aactactttg ggacatgctg   1740
ttttaaaagc ggagtttaaa gaagggaaga aggaattcca ggtgtccctc ttccagacac   1800
tggtgctcct catgttcaac gagggagatg gcttcagctt tgaggagata aaaatggcca   1860
cggggataga ggatagtgaa ttgcgcagaa cgctgcagtc cctggcctgt ggcaaagcac   1920
gtgtgctgat taaagtccc aaggaaagg aagtggaaga tggagacaag ttcatttta    1980 atggagagtt caagcacaag ttgtttagaa taaagatcaa tcaaattcag atgaaggaaa   2040
ctgttgagga acaggttagc accactgaga gagtgtttca ggatagacaa tatcagattg   2100
atgctgctat cgtcagaata atgaagatga aaagactct tggtcataat cttctagttt    2160
ctgaattata taatcagctg aaatttccag taaagcctgg agatttgaaa agagaattg    2220 aatctctgat agacagagac tatatggaga gagacaaaga caatccgaat cagtaccact   2280
acgtggcctg acgcatctgc agacggttcc ccttcatgaa acactagaat gtaccctcag   2340
agcaggaagc acacctgtgc catttctggg actctgattg atccagctgt ggacattgga   2400
aggcgaagga agggaggtgg ctcctgggtc atctttcaca aggctcaaga cttcaacctg   2460
cagatgtatc ttttttccctc cagttttcc tctagttctt ttaggcattt aaattgtttc    2520
tgttactctg tgcaaaataa ctttgagatt ggacaagaag atgttactaa agagaagttc   2580
cttaaaaagg tcttgttctt gtgtcaaaaa gctgcaagtt tggtttgttc tcgtgtgtga   2640
tcatgagtgc acaatgaaga agaccctaga tgctgcattt tttagctctg aagattcctt   2700
aggtatccct gaagacagct cgctcagatg atcagcattt agagtgaaaa caagggccct   2760
tcatgggtga acattagaaa gagccagggt tcaaagctgg cgaatggatg acgcacccta   2820
gccactggcc cctctctgtt tcatgtattt ccaaaagttg taaactttga tggctgattt   2880
ttcgtaagtc aggttctaa gtgagctccc tgaggtgcca aggccatggt gtccgccctg   2940
ctgcgtctgt tcgtcagctg agttccttgt gaatctctgt tttagggttt ggggctagtg   3000
tgtttgtgtt tccattctaa gattgagtct ggcagtccct gttttttgc attggggtaa   3060 ctgctctttg attttttta attgcagtat tgtgtgatt gcaataataa agtttggttt    3120 ggttttaca gtcatgcgca gggacgatcc ttgttctctg ctgtaaactg taaaaagttt    3180
atggagactt aaagtcttga tgttgtgaag cagaggttat tttgtggaaa gattaaaagg   3240
attttgttgg tacctggttt tgtgttgtgt atatatacat gaggttgaac agtgaaagga   3300
aagttcagta gtgatgttag aagggtaact atgacaaaga tacttttgag ataacattta   3360
aaagtacttt atattttaca taatagcatg tttcattttg attaaaagct accaaaggaa   3420
ttttgatcat ggcataagtg tttaaagcaa tattttctgg aatataccaa gtttatataa   3480
tttgattttg tgctaaatta ttaagagtct ctttttgaaa catgcgggtt tgaaatatga   3540
caccttgtgg gtttccatat taaaatcctc actctttaat tgtcatttct atctttgaaa   3600
attttcattt atgagttcca tgatatgtgg tctaagaaag accaaacaga tttctatttt   3660
ttttttctta taagttcgtt gtgtctagag attgttaata ttgtaattta atgtagactt   3720
actttgaata aaattagttt aattggcctt aaaattacat taataaaact ttgtgatatg   3780
caaatgaaaa aaaaaaa                                                  3797
```

<210> SEQ ID NO 3
<211> LENGTH: 1140
<212> TYPE: PRT
<213> ORGANISM: Homo sapiens
<220> FEATURE:
<223> OTHER INFORMATION: DDB1 (p127)

<400> SEQUENCE: 3

```
Met Ser Tyr Asn Tyr Val Val Thr Ala Gln Lys Pro Thr Ala Val Asn
1               5                   10                  15

Gly Cys Val Thr Gly His Phe Thr Ser Ala Glu Asp Leu Asn Leu Leu
            20                  25                  30

Ile Ala Lys Asn Thr Arg Leu Glu Ile Tyr Val Val Thr Ala Glu Gly
        35                  40                  45

Leu Arg Pro Val Lys Glu Val Gly Met Tyr Gly Lys Ile Ala Val Met
    50                  55                  60

Glu Leu Phe Arg Pro Lys Gly Glu Ser Lys Asp Leu Leu Phe Ile Leu
65                  70                  75                  80

Thr Ala Lys Tyr Asn Ala Cys Ile Leu Glu Tyr Lys Gln Ser Gly Glu
                85                  90                  95

Ser Ile Asp Ile Ile Thr Arg Ala His Gly Asn Val Gln Asp Arg Ile
            100                 105                 110

Gly Arg Pro Ser Glu Thr Gly Ile Ile Gly Ile Ile Asp Pro Glu Cys
        115                 120                 125

Arg Met Ile Gly Leu Arg Leu Tyr Asp Gly Leu Phe Lys Val Ile Pro
130                 135                 140

Leu Asp Arg Asp Asn Lys Glu Leu Lys Ala Phe Asn Ile Arg Leu Glu
145                 150                 155                 160

Glu Leu His Val Ile Asp Val Lys Phe Leu Tyr Gly Cys Gln Ala Pro
                165                 170                 175

Thr Ile Cys Phe Val Tyr Gln Asp Pro Gln Gly Arg His Val Lys Thr
            180                 185                 190

Tyr Glu Val Ser Leu Arg Glu Lys Glu Phe Asn Lys Gly Pro Trp Lys
        195                 200                 205

Gln Glu Asn Val Glu Ala Glu Ala Ser Met Val Ile Ala Val Pro Glu
210                 215                 220

Pro Phe Gly Gly Ala Ile Ile Ile Gly Gln Glu Ser Ile Thr Tyr His
225                 230                 235                 240

Asn Gly Asp Lys Tyr Leu Ala Ile Ala Pro Pro Ile Ile Lys Gln Ser
                245                 250                 255

Thr Ile Val Cys His Asn Arg Val Asp Pro Asn Gly Ser Arg Tyr Leu
            260                 265                 270

Leu Gly Asp Met Glu Gly Arg Leu Phe Met Leu Leu Leu Glu Lys Glu
        275                 280                 285

Glu Gln Met Asp Gly Thr Val Thr Leu Lys Asp Leu Arg Val Glu Leu
290                 295                 300

Leu Gly Glu Thr Ser Ile Ala Glu Cys Leu Thr Tyr Leu Asp Asn Gly
305                 310                 315                 320

Val Val Phe Val Gly Ser Arg Leu Gly Asp Ser Gln Leu Val Lys Leu
                325                 330                 335

Asn Val Asp Ser Asn Glu Gln Gly Ser Tyr Val Val Ala Met Glu Thr
            340                 345                 350

Phe Thr Asn Leu Gly Pro Ile Val Asp Met Cys Val Val Asp Leu Glu
        355                 360                 365

Arg Gln Gly Gln Gly Gln Leu Val Thr Cys Ser Gly Ala Phe Lys Glu
370                 375                 380

Gly Ser Leu Arg Ile Ile Arg Asn Gly Ile Gly Ile His Glu His Ala
385                 390                 395                 400

Ser Ile Asp Leu Pro Gly Ile Lys Gly Leu Trp Pro Leu Arg Ser Asp
                405                 410                 415
```

-continued

```
Pro Asn Arg Glu Thr Asp Asp Thr Leu Val Leu Ser Phe Val Gly Gln
            420                 425                 430
Thr Arg Val Leu Met Leu Asn Gly Glu Val Glu Glu Thr Glu Leu
        435                 440                 445
Met Gly Phe Val Asp Asp Gln Gln Thr Phe Phe Cys Gly Asn Val Ala
450                 455                 460
His Gln Gln Leu Ile Gln Ile Thr Ser Ala Ser Val Arg Leu Val Ser
465                 470                 475                 480
Gln Glu Pro Lys Ala Leu Val Ser Glu Trp Lys Glu Pro Gln Ala Lys
                485                 490                 495
Asn Ile Ser Val Ala Ser Cys Asn Ser Ser Gln Val Val Ala Val
            500                 505                 510
Gly Arg Ala Leu Tyr Tyr Leu Gln Ile His Pro Gln Glu Leu Arg Gln
                515                 520                 525
Ile Ser His Thr Glu Met Glu His Glu Val Ala Cys Leu Asp Ile Thr
            530                 535                 540
Pro Leu Gly Asp Ser Asn Gly Leu Ser Pro Leu Cys Ala Ile Gly Leu
545                 550                 555                 560
Trp Thr Asp Ile Ser Ala Arg Ile Leu Lys Leu Pro Ser Phe Glu Leu
                565                 570                 575
Leu His Lys Glu Met Leu Gly Gly Glu Ile Ile Pro Arg Ser Ile Leu
            580                 585                 590
Met Thr Thr Phe Glu Ser Ser His Tyr Leu Leu Cys Ala Leu Gly Asp
                595                 600                 605
Gly Ala Leu Phe Tyr Phe Gly Leu Asn Ile Glu Thr Gly Leu Leu Ser
            610                 615                 620
Asp Arg Lys Lys Val Thr Leu Gly Thr Gln Pro Thr Val Leu Arg Thr
625                 630                 635                 640
Phe Arg Ser Leu Ser Thr Thr Asn Val Phe Ala Cys Ser Asp Arg Pro
                645                 650                 655
Thr Val Ile Tyr Ser Ser Asn His Lys Leu Val Phe Ser Asn Val Asn
            660                 665                 670
Leu Lys Glu Val Asn Tyr Met Cys Pro Leu Asn Ser Asp Gly Tyr Pro
        675                 680                 685
Asp Ser Leu Ala Leu Ala Asn Asn Ser Thr Leu Thr Ile Gly Thr Ile
690                 695                 700
Asp Glu Ile Gln Lys Leu His Ile Arg Thr Val Pro Leu Tyr Glu Ser
705                 710                 715                 720
Pro Arg Lys Ile Cys Tyr Gln Glu Val Ser Gln Cys Phe Gly Val Leu
                725                 730                 735
Ser Ser Arg Ile Glu Val Gln Asp Thr Ser Gly Gly Thr Thr Ala Leu
            740                 745                 750
Arg Pro Ser Ala Ser Thr Gln Ala Leu Ser Ser Ser Val Ser Ser Ser
        755                 760                 765
Lys Leu Phe Ser Ser Ser Thr Ala Pro His Glu Thr Ser Phe Gly Glu
    770                 775                 780
Glu Val Glu Val His Asn Leu Leu Ile Ile Asp Gln His Thr Phe Glu
785                 790                 795                 800
Val Leu His Ala His Gln Phe Leu Gln Asn Glu Tyr Ala Leu Ser Leu
                805                 810                 815
Val Ser Cys Lys Leu Gly Lys Asp Pro Asn Thr Tyr Phe Ile Val Gly
            820                 825                 830
Thr Ala Met Val Tyr Pro Glu Glu Ala Glu Pro Lys Gln Gly Arg Ile
```

```
                    835                 840                 845
Val Val Phe Gln Tyr Ser Asp Gly Lys Leu Gln Thr Val Ala Glu Lys
850                 855                 860

Glu Val Lys Gly Ala Val Tyr Ser Met Val Glu Phe Asn Gly Lys Leu
865                 870                 875                 880

Leu Ala Ser Ile Asn Ser Thr Val Arg Leu Tyr Glu Trp Thr Thr Glu
                885                 890                 895

Lys Glu Leu Arg Thr Glu Cys Asn His Tyr Asn Asn Ile Met Ala Leu
                900                 905                 910

Tyr Leu Lys Thr Lys Gly Asp Phe Ile Leu Val Gly Asp Leu Met Arg
                915                 920                 925

Ser Val Leu Leu Leu Ala Tyr Lys Pro Met Glu Gly Asn Phe Glu Glu
930                 935                 940

Ile Ala Arg Asp Phe Asn Pro Asn Trp Met Ser Ala Val Glu Ile Leu
945                 950                 955                 960

Asp Asp Asp Asn Phe Leu Gly Ala Glu Asn Ala Phe Asn Leu Phe Val
                965                 970                 975

Cys Gln Lys Asp Ser Ala Ala Thr Thr Asp Glu Glu Arg Gln His Leu
                980                 985                 990

Gln Glu Val Gly Leu Phe His Leu Gly Glu Phe Val Asn Val Phe Cys
                995                 1000                1005

His Gly Ser Leu Val Met Gln Asn Leu Gly Glu Thr Ser Thr Pro
                1010                1015                1020

Thr Gln Gly Ser Val Leu Phe Gly Thr Val Asn Gly Met Ile Gly
                1025                1030                1035

Leu Val Thr Ser Leu Ser Glu Ser Trp Tyr Asn Leu Leu Leu Asp
                1040                1045                1050

Met Gln Asn Arg Leu Asn Lys Val Ile Lys Ser Val Gly Lys Ile
                1055                1060                1065

Glu His Ser Phe Trp Arg Ser Phe His Thr Glu Arg Lys Thr Glu
                1070                1075                1080

Pro Ala Thr Gly Phe Ile Asp Gly Asp Leu Ile Glu Ser Phe Leu
                1085                1090                1095

Asp Ile Ser Arg Pro Lys Met Gln Glu Val Val Ala Asn Leu Gln
                1100                1105                1110

Tyr Asp Asp Gly Ser Gly Met Lys Arg Glu Ala Thr Ala Asp Asp
                1115                1120                1125

Leu Ile Lys Val Val Glu Glu Leu Thr Arg Ile His
                1130                1135                1140

<210> SEQ ID NO 4
<211> LENGTH: 4355
<212> TYPE: DNA
<213> ORGANISM: Homo sapiens
<220> FEATURE:
<223> OTHER INFORMATION: Ddb1

<400> SEQUENCE: 4
gcctccttcg gttggcggcc tcgggcttcg ggagtcctcc aagaggccag gtgaggccgt      60
cccgtgatgc cccgcgcccc ggccgctctg gcctgcaacg tgtctctggg gcggaggcag     120
cggcagtgga gttcgctgcg cgctgttggg ggccacctgt cttttcgctt gtgtccctct     180
ttctagtgtc gcgctcgagt cccgacgggc cgctccaagc ctcgacatgt cgtacaacta     240
cgtggtaacg gccagaagc ccaccgcccgt gaacggctgc gtgaccggac actttacttc     300
ggccgaagac ttaaacctgt tgattgccaa aaacacgaga ttagagatct atgtggtcac     360
```

```
cgccgagggg cttcggcccg tcaaagaggt gggcatgtat gggaagattg cggtcatgga    420
gcttttcagg cccaaggggg agagcaagga cctgctgttt atcttgacag cgaagtacaa    480
tgcctgcatc ctggagtata acagagtgg cgagagcatt gacatcatta cgcgagccca    540
tggcaatgtc caggaccgca ttggccgccc ctcagagacc ggcattattg gcatcattga    600
ccctgagtgc cggatgattg gcctgcgtct ctatgatggc cttttcaagg ttattccact    660
agatcgcgat aataaagaac tcaaggcctt caacatccgc ctggaggagc tgcatgtcat    720
tgatgtcaag ttcctatatg gttgccaagc acctactatt tgctttgtct accaggaccc    780 tcagggcgg cacgtaaaaa cctatgaggt gtctctccga gaaaaggaat tcaataaggg    840
cccttggaaa caggaaaatg tcgaagctga agcttccatg gtgatcgcag tcccagagcc    900
ctttgggggg gccatcatca ttggacagga gtcaatcacc tatcacaatg gtgacaaata    960
cctggctatt gcccctccta tcatcaagca aagcacgatt gtgtgccaca atcgagtgga   1020
ccctaatggc tcaagatacc tgctgggaga catggaaggc cggctcttca tgctgctttt   1080
ggagaaggag gaacagatgg atggcaccgt cactctcaag gatctccgtg tagaactcct   1140
tggagagacc tctattgctg agtgcttgac ataccttgat aatggtgttg tgtttgtcgg   1200
gtctcgcctg ggtgactccc agcttgtgaa gctcaacgtt gacagtaatg aacaaggctc   1260
ctatgtagtg gccatggaaa cctttaccaa cttaggaccc attgtcgata tgtgcgtggt   1320
ggacctggag aggcaggggc aggggcagct ggtcacttgc tctgggggctt caaggaagg   1380 ttctttgcgg atcatccgga atggaattgg aatccacgag catgccagca ttgacttacc   1440
aggcatcaaa ggattatggc cactgcggtc tgaccctaat cgtgagactg atgacacttt   1500
ggtgctctct tttgtgggcc agacaagagt tctcatgtta aatggagagg aggtagaaga   1560
aaccgaactg atgggtttcg tggatgatca gcagactttc ttctgtggca acgtggctca   1620
tcagcagctt atccagatca cttcagcatc ggtgaggttg gtctctcaag aacccaaagc   1680
tctggtcagt gaatggaagg agcctcaggc caagaacatc agtgtggcct cctgcaatag   1740
cagccaggtg gtggtggctg taggcagggc cctctactat ctgcagatcc atcctcagga   1800
gctccggcag atcagccaca cagagatgga acatgaagtg gcttgcttgg acatcacccc   1860
attaggagac agcaatggac tgtcccctct ttgtgccatt ggcctctgga cggacatctc   1920
ggctcgtatc ttgaagttgc cctcttttga actactgcac aaggagatgc tgggtggaga   1980
gatcattcct cgctccatcc tgatgaccac ctttgagagt agccattacc tcctttgtgc   2040
cttgggagat ggagcgcttt tctactttgg gctcaacatt gagacaggtc tgttgagcga   2100
ccgtaagaag gtgactttgg gcacccagcc caccgtattg aggactttc gttctctttc   2160 taccaccaac gtctttgctt gttctgaccg ccccactgtc atctatagca gcaaccacaa   2220
attggtcttc tcaaatgtca acctcaagga agtgaactac atgtgtcccc tcaattcaga   2280
tggctatcct gacagcctgg cgctggccaa caatagcacc ctcaccattg gcaccatcga   2340
tgagatccag aagctgcaca ttcgcacagt tcccctctat gagtctccaa ggaagatctg   2400
ctaccaggaa gtgtcccagt gtttcggggt cctctccagc cgcattgaag tccaagacac   2460
gagtgggggc acgacagcct tgaggcccag cgctagcacc caggctctgt ccagcagtgt   2520
aagctccagc aagctgttct ccagcagcac tgctcctcat gagacctcct ttggagaaga   2580
ggtggaggtg cacaacctac ttatcattga ccaacacacc tttgaagtgc ttcatgccca   2640
ccagtttctg cagaatgaat atgccctcag tctggtttcc tgcaagctgg gcaaagaccc   2700
caacacttac ttcattgtgg gcacagcaat ggtgtatcct gaagaggcag agcccaagca   2760
```

-continued

```
gggtcgcatt gtggtctttc agtattcgga tggaaaacta cagactgtgg ctgaaaagga    2820
agtgaaaggg gccgtgtact ctatggtgga atttaacggg aagctgttag ccagcatcaa    2880
tagcacggtg cggctctatg agtggacaac agagaaggag ctgcgcactg agtgcaacca    2940
ctacaacaac atcatggccc tctacctgaa gaccaagggc gacttcatcc tggtgggcga    3000
ccttatgcgc tcagtgctgc tgcttgccta caagcccatg gaaggaaact ttgaagagat    3060
tgctcgagac tttaatccca actggatgag tgctgtggaa atcttggatg atgacaattt    3120
tctgggggct gaaaatgcct ttaacttgtt tgtgtgtcaa aaggatagcg ctgccaccac    3180
tgacgaggag cggcagcacc tccaggaggt tggtcttttc cacctgggcg agtttgtcaa    3240
tgtcttttgc cacggctctc tggtaatgca gaatctgggt gagacttcca cccccacaca    3300
aggctcggtg ctcttcggca cggtcaacgg catgataggg ctggtgacct cactgtcaga    3360
gagctggtac aacctcctgc tggacatgca gaatcgactc aataaagtca tcaaaagtgt    3420
ggggaagatc gagcactcct tctggagatc ctttcacacc gagcggaaga cagaaccagc    3480
cacaggtttc atcgacggtg acttgattga gagtttcctg gatattagcc gccccaagat    3540
gcaggaggtg gtggcaaacc tacagtatga cgatggcagc ggtatgaagc gagaggccac    3600
tgcagacgac ctcatcaagg ttgtggagga gctaactcgg atccattagc caagggcagg    3660
gggccccttt gctgaccctc cccaaaggct ttgccctgct gccctccccc tcctctccac    3720
catcgtcttc ttggccatgg gaggcctttc cctaagccag ctgccccccag agccacagtt    3780 cccctatgtg gaagtggggc gggcttcata gagacttggg aatgagctga aggtgaaaca    3840
ttttctccct ggattttttac cagtctcaca tgattccagc catcaccttaa gaccaccaag    3900 ccttgattgg tgttgccagt tgtcctcctt ccggggaagg attttgcagt tctttggctg    3960
aaaggaagct gtgcgtgtgt gtgtgtgtat gtgtgtgtgt gtatgtgtat ctcacactca    4020
tgcattgtcc tctttttatt tagattggca gtgtagggga ttgtgggtag tggggaagag    4080
ggttaggagg gtttcattgt ctgtgaagtg agaccttcct tttacttttc ttctattgcc    4140
tctgagagca tcaggcctag aggcctgact gccaagccat gggtagcctg ggtgtaaaac    4200
ctggagatgg tggatgatcc ccacgccaca gcccttttgt ctctgcaaac tgccttcttc    4260
ggaaagaaga aggtgggagg atgtgaattg ttagtttctg agtttttacca aataaagtag    4320 aatataagaa gaaaggtaaa aaaaaaaaaa aaaaa    4355
```

<210> SEQ ID NO 5
<211> LENGTH: 723
<212> TYPE: PRT
<213> ORGANISM: Homo sapiens
<220> FEATURE:
<223> OTHER INFORMATION: CUL4A fragment (A37-A759)

<400> SEQUENCE: 5

```
Ala Gly Gly Ser Lys Lys Leu Val Ile Lys Asn Phe Arg Asp Arg Pro
1               5                   10                  15

Arg Leu Pro Asp Asn Tyr Thr Gln Asp Thr Trp Arg Lys Leu His Glu
            20                  25                  30

Ala Val Arg Ala Val Gln Ser Ser Thr Ser Ile Arg Tyr Asn Leu Glu
        35                  40                  45

Glu Leu Tyr Gln Ala Val Glu Asn Leu Cys Ser His Lys Val Ser Pro
    50                  55                  60

Met Leu Tyr Lys Gln Leu Arg Gln Ala Cys Glu Asp His Val Gln Ala
65                  70                  75                  80
```

-continued

```
Gln Ile Leu Pro Phe Arg Glu Asp Ser Leu Asp Ser Val Leu Phe Leu
                 85                  90                  95
Lys Lys Ile Asn Thr Cys Trp Gln Asp His Cys Arg Gln Met Ile Met
            100                 105                 110
Ile Arg Ser Ile Phe Leu Phe Leu Asp Arg Thr Tyr Val Leu Gln Asn
        115                 120                 125
Ser Thr Leu Pro Ser Ile Trp Asp Met Gly Leu Glu Leu Phe Arg Thr
    130                 135                 140
His Ile Ile Ser Asp Lys Met Val Gln Ser Lys Thr Ile Asp Gly Ile
145                 150                 155                 160
Leu Leu Leu Ile Glu Arg Glu Arg Ser Gly Glu Ala Val Asp Arg Ser
                165                 170                 175
Leu Leu Arg Ser Leu Leu Gly Met Leu Ser Asp Leu Gln Val Tyr Lys
            180                 185                 190
Asp Ser Phe Glu Leu Lys Phe Leu Glu Glu Thr Asn Cys Leu Tyr Ala
        195                 200                 205
Ala Glu Gly Gln Arg Leu Met Gln Glu Arg Glu Val Pro Glu Tyr Leu
    210                 215                 220
Asn His Val Ser Lys Arg Leu Glu Glu Glu Gly Asp Arg Val Ile Thr
225                 230                 235                 240
Tyr Leu Asp His Ser Thr Gln Lys Pro Leu Ile Ala Cys Val Glu Lys
                245                 250                 255
Gln Leu Leu Gly Glu His Leu Thr Ala Ile Leu Gln Lys Gly Leu Asp
            260                 265                 270
His Leu Leu Asp Glu Asn Arg Val Pro Asp Leu Ala Gln Met Tyr Gln
        275                 280                 285
Leu Phe Ser Arg Val Arg Gly Gly Gln Gln Ala Leu Leu Gln His Trp
    290                 295                 300
Ser Glu Tyr Ile Lys Thr Phe Gly Thr Ala Ile Val Ile Asn Pro Glu
305                 310                 315                 320
Lys Asp Lys Asp Met Val Gln Asp Leu Leu Asp Phe Lys Asp Lys Val
                325                 330                 335
Asp His Val Ile Glu Val Cys Phe Gln Lys Asn Glu Arg Phe Val Asn
            340                 345                 350
Leu Met Lys Glu Ser Phe Glu Thr Phe Ile Asn Lys Arg Pro Asn Lys
        355                 360                 365
Pro Ala Glu Leu Ile Ala Lys His Val Asp Ser Lys Leu Arg Ala Gly
    370                 375                 380
Asn Lys Glu Ala Thr Asp Glu Glu Leu Glu Arg Thr Leu Asp Lys Ile
385                 390                 395                 400
Met Ile Leu Phe Arg Phe Ile His Gly Lys Asp Val Phe Glu Ala Phe
                405                 410                 415
Tyr Lys Lys Asp Leu Ala Lys Arg Leu Leu Val Gly Lys Ser Ala Ser
            420                 425                 430
Val Asp Ala Glu Lys Ser Met Leu Ser Lys Leu Lys His Glu Cys Gly
        435                 440                 445
Ala Ala Phe Thr Ser Lys Leu Glu Gly Met Phe Lys Asp Met Glu Leu
    450                 455                 460
Ser Lys Asp Ile Met Val His Phe Lys Gln His Met Gln Asn Gln Ser
465                 470                 475                 480
Asp Ser Gly Pro Ile Asp Leu Thr Val Asn Ile Leu Thr Met Gly Tyr
                485                 490                 495
Trp Pro Thr Tyr Thr Pro Met Glu Val His Leu Thr Pro Glu Met Ile
            500                 505                 510
```

-continued

Lys Leu Gln Glu Val Phe Lys Ala Phe Tyr Leu Gly Lys His Ser Gly
            515                 520                 525

Arg Lys Leu Gln Trp Gln Thr Thr Leu Gly His Ala Val Leu Lys Ala
530                 535                 540

Glu Phe Lys Glu Gly Lys Lys Glu Phe Gln Val Ser Leu Phe Gln Thr
545                 550                 555                 560

Leu Val Leu Leu Met Phe Asn Glu Gly Asp Gly Phe Ser Phe Glu Glu
                565                 570                 575

Ile Lys Met Ala Thr Gly Ile Glu Asp Ser Glu Leu Arg Arg Thr Leu
            580                 585                 590

Gln Ser Leu Ala Cys Gly Lys Ala Arg Val Leu Ile Lys Ser Pro Lys
        595                 600                 605

Gly Lys Glu Val Glu Asp Gly Asp Lys Phe Ile Phe Asn Gly Glu Phe
    610                 615                 620

Lys His Lys Leu Phe Arg Ile Lys Ile Asn Gln Ile Gln Met Lys Glu
625                 630                 635                 640

Thr Val Glu Glu Gln Val Ser Thr Thr Glu Arg Val Phe Gln Asp Arg
                645                 650                 655

Gln Tyr Gln Ile Asp Ala Ala Ile Val Arg Ile Met Lys Met Arg Lys
            660                 665                 670

Thr Leu Gly His Asn Leu Leu Val Ser Glu Leu Tyr Asn Gln Leu Lys
        675                 680                 685

Phe Pro Val Lys Pro Gly Asp Leu Lys Lys Arg Ile Glu Ser Leu Ile
    690                 695                 700

Asp Arg Asp Tyr Met Glu Arg Asp Lys Asp Asn Pro Asn Gln Tyr His
705                 710                 715                 720

Tyr Val Ala

<210> SEQ ID NO 6
<211> LENGTH: 365
<212> TYPE: PRT
<213> ORGANISM: Homo sapiens
<220> FEATURE:
<223> OTHER INFORMATION: CUL4A fragment (A37-R401)

<400> SEQUENCE: 6

Ala Gly Gly Ser Lys Lys Leu Val Ile Lys Asn Phe Arg Asp Arg Pro
1               5                   10                  15

Arg Leu Pro Asp Asn Tyr Thr Gln Asp Thr Trp Arg Lys Leu His Glu
            20                  25                  30

Ala Val Arg Ala Val Gln Ser Ser Thr Ser Ile Arg Tyr Asn Leu Glu
        35                  40                  45

Glu Leu Tyr Gln Ala Val Glu Asn Leu Cys Ser His Lys Val Ser Pro
    50                  55                  60

Met Leu Tyr Lys Gln Leu Arg Gln Ala Cys Glu Asp His Val Gln Ala
65                  70                  75                  80

Gln Ile Leu Pro Phe Arg Glu Asp Ser Leu Asp Ser Val Leu Phe Leu
                85                  90                  95

Lys Lys Ile Asn Thr Cys Trp Gln Asp His Cys Arg Gln Met Ile Met
            100                 105                 110

Ile Arg Ser Ile Phe Leu Phe Leu Asp Arg Thr Tyr Val Leu Gln Asn
        115                 120                 125

Ser Thr Leu Pro Ser Ile Trp Asp Met Gly Leu Glu Leu Phe Arg Thr
    130                 135                 140

His Ile Ile Ser Asp Lys Met Val Gln Ser Lys Thr Ile Asp Gly Ile

```
            145                 150                 155                 160
Leu Leu Leu Ile Glu Arg Glu Arg Ser Gly Glu Ala Val Asp Arg Ser
                    165                 170                 175
Leu Leu Arg Ser Leu Leu Gly Met Leu Ser Asp Leu Gln Val Tyr Lys
                180                 185                 190
Asp Ser Phe Glu Leu Lys Phe Leu Glu Glu Thr Asn Cys Leu Tyr Ala
            195                 200                 205
Ala Glu Gly Gln Arg Leu Met Gln Glu Arg Val Pro Glu Tyr Leu
        210                 215                 220
Asn His Val Ser Lys Arg Leu Glu Glu Glu Gly Asp Arg Val Ile Thr
225                 230                 235                 240
Tyr Leu Asp His Ser Thr Gln Lys Pro Leu Ile Ala Cys Val Glu Lys
                245                 250                 255
Gln Leu Leu Gly Glu His Leu Thr Ala Ile Leu Gln Lys Gly Leu Asp
                260                 265                 270
His Leu Leu Asp Glu Asn Arg Val Pro Asp Leu Ala Gln Met Tyr Gln
            275                 280                 285
Leu Phe Ser Arg Val Arg Gly Gly Gln Gln Ala Leu Leu Gln His Trp
        290                 295                 300
Ser Glu Tyr Ile Lys Thr Phe Gly Thr Ala Ile Val Ile Asn Pro Glu
305                 310                 315                 320
Lys Asp Lys Asp Met Val Gln Asp Leu Leu Asp Phe Lys Asp Lys Val
                325                 330                 335
Asp His Val Ile Glu Val Cys Phe Gln Lys Asn Glu Arg Phe Val Asn
            340                 345                 350
Leu Met Lys Glu Ser Phe Glu Thr Phe Ile Asn Lys Arg
        355                 360                 365

<210> SEQ ID NO 7
<211> LENGTH: 144
<212> TYPE: PRT
<213> ORGANISM: Homo sapiens
<220> FEATURE:
<223> OTHER INFORMATION: CUL4A N-term (K41-S184)

<400> SEQUENCE: 7

Lys Lys Leu Val Ile Lys Asn Phe Arg Asp Arg Pro Arg Leu Pro Asp
1               5                   10                  15
Asn Tyr Thr Gln Asp Thr Trp Arg Lys Leu His Glu Ala Val Arg Ala
            20                  25                  30
Val Gln Ser Ser Thr Ser Ile Arg Tyr Asn Leu Glu Glu Leu Tyr Gln
        35                  40                  45
Ala Val Glu Asn Leu Cys Ser His Lys Val Ser Pro Met Leu Tyr Lys
    50                  55                  60
Gln Leu Arg Gln Ala Cys Glu Asp His Val Gln Ala Gln Ile Leu Pro
65                  70                  75                  80
Phe Arg Glu Asp Ser Leu Asp Ser Val Leu Phe Leu Lys Lys Ile Asn
                85                  90                  95
Thr Cys Trp Gln Asp His Cys Arg Gln Met Ile Met Ile Arg Ser Ile
            100                 105                 110
Phe Leu Phe Leu Asp Arg Thr Tyr Val Leu Gln Asn Ser Thr Leu Pro
        115                 120                 125
Ser Ile Trp Asp Met Gly Leu Glu Leu Phe Arg Thr His Ile Ile Ser
    130                 135                 140

<210> SEQ ID NO 8
```

```
<211> LENGTH: 319
<212> TYPE: PRT
<213> ORGANISM: Homo sapiens
<220> FEATURE:
<223> OTHER INFORMATION: BPB domain of DDB1

<400> SEQUENCE: 8
```

Arg Asn Gly Ile Gly Ile His Glu His Ala Ser Ile Asp Leu Pro Gly
1               5                   10                  15

Ile Lys Gly Leu Trp Pro Leu Arg Ser Asp Pro Asn Arg Glu Thr Asp
            20                  25                  30

Asp Thr Leu Val Leu Ser Phe Val Gly Gln Thr Arg Val Leu Met Leu
        35                  40                  45

Asn Gly Glu Glu Val Glu Thr Glu Leu Met Gly Phe Val Asp Asp
50                  55                  60

Gln Gln Thr Phe Phe Cys Gly Asn Val Ala His Gln Leu Ile Gln
65                  70                  75                  80

Ile Thr Ser Ala Ser Val Arg Leu Val Ser Gln Glu Pro Lys Ala Leu
                85                  90                  95

Val Ser Glu Trp Lys Glu Pro Gln Ala Lys Asn Ile Ser Val Ala Ser
            100                 105                 110

Cys Asn Ser Ser Gln Val Val Ala Val Gly Arg Ala Leu Tyr Tyr
        115                 120                 125

Leu Gln Ile His Pro Gln Glu Leu Arg Gln Ile Ser His Thr Glu Met
130                 135                 140

Glu His Glu Val Ala Cys Leu Asp Ile Thr Pro Leu Gly Asp Ser Asn
145                 150                 155                 160

Gly Leu Ser Pro Leu Cys Ala Ile Gly Leu Trp Thr Asp Ile Ser Ala
                165                 170                 175

Arg Ile Leu Lys Leu Pro Ser Phe Glu Leu Leu His Lys Glu Met Leu
            180                 185                 190

Gly Gly Glu Ile Ile Pro Arg Ser Ile Leu Met Thr Thr Phe Glu Ser
        195                 200                 205

Ser His Tyr Leu Leu Cys Ala Leu Gly Asp Gly Ala Leu Phe Tyr Phe
210                 215                 220

Gly Leu Asn Ile Glu Thr Gly Leu Leu Ser Asp Arg Lys Lys Val Thr
225                 230                 235                 240

Leu Gly Thr Gln Pro Thr Val Leu Arg Thr Phe Arg Ser Leu Ser Thr
                245                 250                 255

Thr Asn Val Phe Ala Cys Ser Asp Arg Pro Thr Val Ile Tyr Ser Ser
            260                 265                 270

Asn His Lys Leu Val Phe Ser Asn Val Asn Leu Lys Glu Val Asn Tyr
        275                 280                 285

Met Cys Pro Leu Asn Ser Asp Gly Tyr Pro Asp Ser Leu Ala Leu Ala
290                 295                 300

Asn Asn Ser Thr Leu Thr Ile Gly Thr Ile Asp Glu Ile Gln Lys
305                 310                 315

```
<210> SEQ ID NO 9
<211> LENGTH: 21
<212> TYPE: DNA
<213> ORGANISM: Mus musculus
<220> FEATURE:
<223> OTHER INFORMATION: Cul4b shRNA

<400> SEQUENCE: 9
```
gtagtaacga gagagaagac t                                         21

```
<210> SEQ ID NO 10
<211> LENGTH: 21
<212> TYPE: DNA
<213> ORGANISM: Mus musculus
<220> FEATURE:
<223> OTHER INFORMATION: Pcid2 shRNA-1

<400> SEQUENCE: 10
ggcaaagcac gagacgttct t                                                    21

<210> SEQ ID NO 11
<211> LENGTH: 22
<212> TYPE: DNA
<213> ORGANISM: Mus musculus
<220> FEATURE:
<223> OTHER INFORMATION: Pcid2 shRNA-2

<400> SEQUENCE: 11
gatgaaatgt ttgcagctca tt                                                   22

<210> SEQ ID NO 12
<211> LENGTH: 22
<212> TYPE: DNA
<213> ORGANISM: Mus musculus
<220> FEATURE:
<223> OTHER INFORMATION: p21 shRNA

<400> SEQUENCE: 12
gagaacggtg gaactttgac tt                                                   22

<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Scrambled Cul4b shRNA

<400> SEQUENCE: 13
gtcgcagcaa taaatacggc t                                                    21

<210> SEQ ID NO 14
<211> LENGTH: 19
<212> TYPE: DNA
<213> ORGANISM: Homo sapiens
<220> FEATURE:
<223> OTHER INFORMATION: Cul4a shRNA

<400> SEQUENCE: 14
gaagctggtc atcaagaac                                                       19

<210> SEQ ID NO 15
<211> LENGTH: 26
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Cul4a truncated up

<400> SEQUENCE: 15
gcgatatccg cggacgaggg ccctcg                                               26

<210> SEQ ID NO 16
<211> LENGTH: 73
<212> TYPE: DNA
```

<213> ORGANISM: Artificial sequence
<220> FEATURE:
<223> OTHER INFORMATION: Synthetic oligonucleotide
<220> FEATURE:
<223> OTHER INFORMATION: Cul4a truncated 1st down

<400> SEQUENCE: 16
catatagtct ctgtctataa gtgactcaat cctttttttc aaatctccag gctccttaaa    60
gtccgccttc agc                                                       73

<210> SEQ ID NO 17
<211> LENGTH: 74
<212> TYPE: DNA
<213> ORGANISM: Artificial sequence
<220> FEATURE:
<223> OTHER INFORMATION: Synthetic oligonucleotide
<220> FEATURE:
<223> OTHER INFORMATION: Cul4a truncated 2nd down

<400> SEQUENCE: 17
gctctagatc atgccacgta gtggtactga tttggactgt ctttgtctcg ttccatatag    60
tctctgtcta taag                                                      74

<210> SEQ ID NO 18
<211> LENGTH: 295
<212> TYPE: PRT
<213> ORGANISM: Homo sapiens
<220> FEATURE:
<223> OTHER INFORMATION: DN-CUL4A (M1-L295)

<400> SEQUENCE: 18

Met Ala Asp Glu Ala Pro Arg Lys Gly Ser Phe Ser Ala Leu Val Gly
1               5                   10                  15

Arg Thr Asn Gly Leu Thr Lys Pro Ala Ala Leu Ala Ala Ala Pro Ala
            20                  25                  30

Lys Pro Gly Gly Ala Gly Gly Ser Lys Lys Leu Val Ile Lys Asn Phe
        35                  40                  45

Arg Asp Arg Pro Arg Leu Pro Asp Asn Tyr Thr Gln Asp Thr Trp Arg
    50                  55                  60

Lys Leu His Glu Ala Val Arg Ala Val Gln Ser Ser Thr Ser Ile Arg
65                  70                  75                  80

Tyr Asn Leu Glu Glu Leu Tyr Gln Ala Val Glu Asn Leu Cys Ser His
                85                  90                  95

Lys Val Ser Pro Met Leu Tyr Lys Gln Leu Arg Gln Ala Cys Glu Asp
            100                 105                 110

His Val Gln Ala Gln Ile Leu Pro Phe Arg Glu Asp Ser Leu Asp Ser
        115                 120                 125

Val Leu Phe Leu Lys Lys Ile Asn Thr Cys Trp Gln Asp His Cys Arg
    130                 135                 140

Gln Met Ile Met Ile Arg Ser Ile Phe Leu Phe Leu Asp Arg Thr Tyr
145                 150                 155                 160

Val Leu Gln Asn Ser Thr Leu Pro Ser Ile Trp Asp Met Gly Leu Glu
                165                 170                 175

Leu Phe Arg Thr His Ile Ile Ser Asp Lys Met Val Gln Ser Lys Thr
            180                 185                 190

Ile Asp Gly Ile Leu Leu Leu Ile Glu Arg Glu Arg Ser Gly Glu Ala
        195                 200                 205

Val Asp Arg Ser Leu Leu Arg Ser Leu Leu Gly Met Leu Ser Asp Leu
    210                 215                 220

-continued

```
Gln Val Tyr Lys Asp Ser Phe Glu Leu Lys Phe Leu Glu Glu Thr Asn
225                 230                 235                 240

Cys Leu Tyr Ala Ala Glu Gly Gln Arg Leu Met Gln Glu Arg Glu Val
                245                 250                 255

Pro Glu Tyr Leu Asn His Val Ser Lys Arg Leu Glu Glu Glu Gly Asp
                260                 265                 270

Arg Val Ile Thr Tyr Leu Asp His Ser Thr Gln Lys Pro Leu Ile Ala
            275                 280                 285

Cys Val Glu Lys Gln Leu Leu
            290             295
```